US007273878B2

(12) United States Patent

Abe et al.

(10) Patent No.: US 7,273,878 B2

(45) Date of Patent: Sep. 25, 2007

(54) DIFLUOROALKENE DERIVATIVE, PEST CONTROL AGENT CONTAINING THE SAME, AND INTERMEDIATE THEREFOR

(75) Inventors: Tetsuya Abe, Shizuoka (JP); Ryuji Tamai, Shizuoka (JP); Minoru Ito, Shizuoka (JP); Masatoshi Tamaru, Shizuoka (JP); Hiroyuki Yano, Shizuoka (JP); Satoru Takahashi, Shizuoka (JP); Norimichi Muramatsu, Shizuoka (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 56 days.

(21) Appl. No.: 10/491,128

(22) PCT Filed: Sep. 30, 2002

(86) PCT No.: PCT/JP02/10142

§ 371 (c)(1),
(2), (4) Date: Mar. 29, 2004

(87) PCT Pub. No.: WO03/029211

PCT Pub. Date: Apr. 10, 2003

(65) Prior Publication Data

US 2004/0248872 A1 Dec. 9, 2004

(30) Foreign Application Priority Data

Sep. 28, 2001 (JP) ............................ 2001-299687
May 17, 2002 (JP) ............................ 2002-142329

(51) Int. Cl.

| | |
|---|---|
| ***C07D 213/79*** | (2006.01) |
| ***C07D 213/80*** | (2006.01) |
| ***C07D 213/803*** | (2006.01) |
| ***A01N 43/40*** | (2006.01) |

(52) U.S. Cl. ...................................... 514/350; 546/267

(58) Field of Classification Search ................ 546/267; 514/350

See application file for complete search history.

(56) References Cited

FOREIGN PATENT DOCUMENTS

| | | | |
|---|---|---|---|
| EP | 0432861 | | 6/1991 |
| JP | 04-154740 | A1 | 5/1992 |
| JP | 2000038379 | A2 * | 2/2000 |
| JP | 2000198769 | A2 * | 7/2000 |
| WO | WO-97/08130 | | 3/1997 |

OTHER PUBLICATIONS

English Translation of JP-2000198769.*
English Translation of JP-2000038379.*
International Search Report (English Translation).
European Search Report Dated: Nov. 10, 2004.
International Search Report (English Translation) Nov. 19, 2002.

* cited by examiner

*Primary Examiner*—Venkataraman Balasubramanian
(74) *Attorney, Agent, or Firm*—Rader, Fishman & Grauer PLLC

(57) ABSTRACT

A difluoroalkene derivative which is sufficiently effective in controlling various pests even when used in a small dose and is highly safe for crops, natural enemies to the pests, and animals; and an intermediate for the derivative. The difluoroalkene derivative is represented by the general formula: [I] wherein $L^1$ and $L^2$ are the same or different and each represents oxygen or sulfur; n is an integer of 2 to 8; and Q represents a 5- to 12-membered heterocyclic group having any desired heteroatom selected among nitrogen, oxygen, and sulfur

[1]

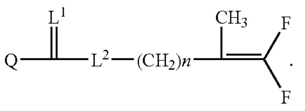

5 Claims, No Drawings

DIFLUOROALKENE DERIVATIVE, PEST CONTROL AGENT CONTAINING THE SAME, AND INTERMEDIATE THEREFOR

TECHNICAL FIELD

The present invention relates to a novel difluoroalkene derivative and a pest control agent containing the same as an effective ingredient.

BACKGROUND ART

It has been already reported that a difluoroalkene derivative has an activity as a pest control agent. For example, JP-A-2000-38379 discloses a linear difluoroalkene derivative esterificated with pyridine carboxylic acids. JP-A-2000-86636 discloses a linear difluoroalkene derivative esterificated with pyrazole carboxylic acids. JP-A-2000-186073 discloses a linear difluoroalkene derivative esterificated with thiophene-2-carboxylic acid, furan-2-carboxylic acid, 1,4-pyrimidine-2-carboxylic acid or quinoline-4-carboxylic acid. JP-A-2000-198769 discloses a linear difluoroalkene derivative thioesterificated or dithioesterificated with benzoic acid or pyridine carboxylic acids. U.S. Pat. No. 5,081,287 discloses a linear difluoroalkene derivative esterificated with an alkanecarboxylic acid, an alkanecarboxylic acid, an aromatic carboxylic acid or the like. WO97/08130 discloses a linear difluoroalkene derivative esterificated with substituted benzoic acids (see JP-A-11-510474).

All of these difluoroalkene derivatives have a 1,1-difluoroethylene ($—C{=}CF_2$) type of difluoroalkene end group.

Also in DPO No. 4122506 discloses a 2-methyl- or 2-ethyl-1,1-difluoroethylene type of difluoroalkene derivative esterificated with various carboxylic acids, wherein a heterocyclic carboxylic acid may be used as a carboxylic acid but no specific example is shown. In EP-A-432861 (see JP-A-4-154740) discloses a 2-methyl-, 2-ethyl- or 2-phenyl-1,1-difluoroethylene type of difluoroalkene derivative esterificated with various carboxylic acids, wherein heterocyclic carboxylic acids such as pyridine, triazole or chromene may be preferably used as a carboxylic acid, but no specific compound is exemplified.

Desirably, a pest control agent used for useful crops shows a sufficient pest control effect with small dose against various pests which have resistance to conventional pest control agents for agricultural or gardening use, and is highly safe for crops, natural enemies to the pests and mammals. From these viewpoints, conventional difluoroalkene derivatives are not necessarily satisfactory, and thus development of apest control agent having a sufficient pest control effect and high safety has been demanded.

DISCLOSURE OF THE INVENTION

In these circumstances, the present inventors have found, after extensive study to solve the above-described problems, that among difluoroalkene derivatives esterificated with heterocyclic carboxylic acids, branched 1,1-difluoropropylene type of difluoroalkene derivatives having a methyl group at terminal difluoroethylene moiety show superior pest control effect against various pests which have resistance to conventional pest control agents for agriculture or gardening, and that they have high safety for natural enemies to the pests and mammals, and completed the present invention based on these findings.

Among branched 1,1-difluoropropylene type of difluoroalkene derivatives having a methyl group at terminal difluoroethylene moiety, difluoroalkene derivatives shown by the following general formula [1] have not described in any literature and are thus novel compounds.

Namely, the present invention consists is described as follows.

(1) A difluoroalkene derivative having the general formula [1] or a pharmacologically acceptable salt thereof:

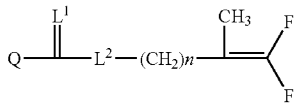

[1]

wherein $L^1$ and $L^2$ are the same or different and each represents an oxygen atom or a sulfur atom;

n represents an integer of 2 to 8;

Q represents a 5- to 12-membered heterocyclic group having any hetero atom selected from a nitrogen atom, an oxygen atom and a sulfur atom, and when a hetero atom of these heterocyclic groups is a nitrogen atom, Q may be in the form of oxidized N-oxide; Q may be substituted with same or different 1 to 4 substituents group X;

X represents a hydroxyl group, a halogen atom, an alkyl group with 1 to 12 carbon atoms which may be mono-substituted with any group selected from substituents group α, an alkoxy group with 1 to 12 carbon atoms which may be mono-substituted with any group selected from substituents group α, an alkylthio group with 1 to 12 carbon atoms which may be mono-substituted with any group selected from substituents group α, an alkylsulfinyl group with 1 to 12 carbon atoms which may be mono-substituted with any group selected from substituents group α, an alkylsulfonyl group with 1 to 12 carbon atoms which may be mono-substituted with any group selected from substituents group α, an acyl group with 1 to 6 carbon atoms which may be mono-substituted with any group selected from substituents group α, an alkoxycarbonyl group with 2 to 6 carbon atoms which may be mono-substituted with any group selected from substituents group α, an acylamino group with 1 to 6 carbon atoms which may be mono-substituted with any group selected from substituents group α (a nitrogen atom of said group may be substituted with an alkyl group with 1 to 6 carbon atoms), an alkylsulfonylamino group with 1 to 6 carbon atoms which may be mono-substituted with any group selected from substituents group α (a nitrogen atom of said group may be substituted with an alkyl group with 1 to 6 carbon atoms), a haloalkyl group with 1 to 4 carbon atoms, an alkoxyalkyl group with 2 to 6 carbon atoms, an alkenyl group with 2 to 6 carbon atoms, a haloalkenyl group with 2 to 7 carbon atoms, an alkynyl group with 2 to 6 carbon atoms which may be mono-substituted with any group selected from substituents group α, a cycloalkyl group with 3 to 6 carbon atoms, a cycloalkylalkyl group with 4 to 7 carbon atoms (said group may be substituted with a halogen atom or an alkyl group), a haloalkoxy group with 1 to 6 carbon atoms, an alkoxyalkyloxy group with 2 to 6 carbon atoms, an alkenyloxy group with 3 to 8 carbon atoms, a haloalkenyloxy group with 3 to 8 carbon atoms, an alkynyloxy group with 3 to 6 carbon atoms, a cycloalkyloxy group with 3 to 7 carbon atoms, a cycloalkylalkyloxy group with 4 to 7 carbon atoms (said group may be substituted with a halogen atom or an alkyl group), an acyloxy group with 1 to 6 carbon atoms, a haloalkylcarbonyl group with 2 to 5 carbon atoms, a cyano group, a carbamoyl group (a nitrogen atom of said group may be substituted with the same or different alkyl group having 1 to 4 carbon atoms), a phenyl group which may be substituted with any 1 to 4 groups selected from substituents group β, a phenoxy group which may be substituted with any 1 to 4 groups selected from substituents group β, a phenylthio group which may be substituted with any 1 to 4 groups selected from substituents group β, a phenylsulfinyl group which may be substituted with any 1 to 4 groups selected from substituents group β, a phenylsulfonyl group which may be substituted with any 1 to 4 groups selected from substituents group β, a phenylamino group which may be substituted with any 1 to 4 groups selected from substituents group β, a nitrogen atom of said group may be substituted with an alkyl group having 1 to 4 carbon atoms, an alkenyl group having 2 to 4 carbon atoms, an alkynyl group having 3 to 4 carbon atoms, an acyl group having 1 to 4 carbon atoms, an alkoxycarbonyl group having 2 to 4 carbon atoms, a carbamoyl group (a nitrogen atom of said group may be substituted with the same or different alkyl group having 1 to 4 carbon atoms), or an alkylsulfonyl group having 1 to 4 carbon atoms), a pyridyl group which may be substituted with any 1 to 4 groups selected from substituents group β, a thienyl group which may be substituted with any 1 to 3 groups selected from substituents group β, a pyrazolyl group which may be substituted with any 1 to 3 groups selected from substituents group β, a pyridyloxy group which may be substituted with any 1 to 4 groups selected from substituents group β, a phenylcarbamoyl group which may be substituted with any 1 to 4 groups selected from substituents group β (a nitrogen atom of said group may be substituted with an alkyl group having 1 to 4 carbon atoms), a benzoyl group which may be substituted with any 1 to 4 groups selected from substituents group β, a benzoylamino group which may be substituted with any 1 to 4 groups selected from substituents group β (a nitrogen atom of said group may be substituted with an alkyl group having 1 to 4 carbon atoms), a phenylsulfonylamino group which may be substituted with any 1 to 4 groups selected from substituents group β (a nitrogen atom of said group may be substituted with an alkyl group having 1 to 4 carbon atoms), a phthalimide group which may be substituted with any 1 to 4 groups selected from substituents group β, a nitro group, an amino group, an alkylamino group with 1 to 12 carbon atoms which may be mono-substituted with any group selected from substituents group α (a nitrogen atom of said group may be substituted with an alkyl group having 1 to 6 carbon atoms which may be mono-substituted with any group selected from substituents group α, an alkenyl group having 2 to 4 carbon atoms, an alkynyl group having 3 to 4 carbon atoms or a hydroxyl group), an cycloalkylamino group with 3 to 6 carbon atoms (a nitrogen atom of said group may be substituted with an alkyl group having 1 to 6 carbon atoms, an alkenyl group having 2 to 4 carbon atoms, an alkynyl group having 3 to 4 carbon atoms, an acyl group having 1 to 4 carbon atoms, an alkoxycarbonyl group having 2 to 4 carbon atoms or an alkylsulfonyl group having 1 to 4 carbon atoms), an alkoxyamino group with 1 to 12 carbon atoms which may be mono-substituted with any group selected from substituents group α (a nitrogen atom of said group may be substituted with an alkyl group having 1 to 10 carbon atoms which may be mono-substituted with any group selected from substituents group α, an alkenyl group having 2 to 4 carbon atoms, an alkynyl group having 3 to 4 carbon atoms, an acyl group having 1 to 4 carbon atoms, an alkoxycarbonyl group having 2 to 4 carbon atoms or an alkylsulfonyl group having 1 to 4 carbon atoms), a pyrrolidinyl group, a piperidinyl group, a haloalkylcarbonylamino group having 2 to 5 carbon atoms (a nitrogen atom of said group may be substituted with an alkyl group having 1 to 6 carbon atoms) or a haloalkylsulfonylamino group having 1 to 4 carbon atoms (a nitrogen atom of said group may be substituted with an alkyl group having 1 to 6 carbon atoms);

a substituents group X may form a 5- to 8-membered ring which may be substituted with 1 to 4 halogen atoms, by bonding two adjacent alkyl groups, alkoxy groups, an alkyl group and an alkoxy group, an alkyl group and an alkylthio group, an alkyl group and an alkylsulfonyl group, an alkyl group and a monoalkylamino group or an alkyl group and a dialkylamino group;

[Substitutents Group α]

Substituents group α include a phenyl group which may be substituted with any 1 to 4 groups selected from substituents group β, a phenoxy group which may be substituted with any 1 to 4 groups selected from substituents group β, a benzyloxy group which may be substituted with any 1 to 4 groups selected from substituents group β, a pyridyl group which may be substituted with any 1 to 4 groups selected from substituents group β, a pyridyloxy group which may be substituted with any 1 to 4 groups selected from substituents group β, a benzoyloxy group which may be substituted with any 1 to 4 groups selected from substituents group β, a benzoylamino group which may be substituted with any 1 to 4 groups selected from substituents group β, a nitrogen atom of said group may be substituted with an alkyl group having 1 to 4 carbon atoms, a phenylsulfonylamino group which may be substituted with any 1 to 4 groups selected from substituents group β, a nitrogen atom of said group may be substituted with an alkyl group having 1 to 4 carbon atoms, a phenylcarbamoyl group which may be substituted with any 1 to 4 groups selected from substituents group β (a nitrogen atom of said group may be substituted with an alkyl group having 1 to 4 carbon atoms) and a benzyloxycarbonyl group which may be substituted with any 1 to 4 groups selected from substituents group β or a cyano group;

[Substituents Group β]

Substituents group β include a hydroxyl group, a halogen atom, an alkyl group with 1 to 6 carbon atoms, a haloalkyl group with 1 to 4 carbon atoms, an alkoxy group with 1 to 6 carbon atoms, a haloalkoxy group with 1 to 4 carbon atoms, a methylenedioxy group, an alkylthio group with 1 to 6 carbon atoms, an alkylsulfinyl group with 1 to 6 carbon atoms, an alkylsulfonyl group with 1 to 6 carbon atoms, a cyano group, a carbamoyl group (a nitrogen atom of said group may be substituted with an alkyl group having 1 to 4 carbon atoms), a nitro group, an amino group, a phenyl group which may be substituted with any 1 to 4 groups selected from substituents group γ, a phenoxy group which may be substituted with any 1 to 4 groups selected from substituents group γ, a benzyloxy group which may be substituted with any 1 to 4 groups selected from substituents group γ, a pyridyl group which may be substituted with any 1 to 4 groups selected from substituents group γ, a pyridyloxy group which may be substituted with any 1 to 4 groups selected from substituents group γ, a benzoylamino group which may be substituted with any 1 to 4 groups selected from substituents group γ (a nitrogen atom of said group may be substituted with an alkyl group having 1 to 4 carbon atoms), a phenylsulfonylamino group which may be substituted with any 1 to 4 groups selected from substituents group γ (a nitrogen atom of said group may be substituted with an alkyl group having 1 to 4 carbon atoms), a phenylcarbamoyl group which may be substituted with any 1 to 4 groups selected from substituents group γ (a nitrogen atom of said group may be substituted with an alkyl group having 1 to 4 carbon atoms), an alkylamino group with 1 to 4 carbon atoms, a dialkylamino group with 1 to 4 carbon atoms (a dialkyl group of said group may be the same or different), an acylamino group with 1 to 6 carbon atoms (a nitrogen atom of said group may be substituted with an alkyl group having 1 to 4 carbon atoms or an acyl group having 1 to 4 carbon atoms), a haloalkylcarbonylamino group with 1 to 5 carbon atoms (a nitrogen atom of said group may be substituted with an alkyl group having 1 to 4 carbon atoms), an alkylsulfonylamino group with 1 to 6 carbon atoms (a nitrogen atom of said group may be substituted with an alkyl group having 1 to 4 carbon atoms) or a haloalkylsulfonylamino group with 1 to 4 carbon atoms (a nitrogen atom of said group may be substituted with an alkyl group having 1 to 4 carbon atoms);

[Substituents Group γ]

Substituents group γ include a hydroxyl group, a halogen atom, an alkyl group with 1 to 6 carbon atoms, an haloalkyl group with 1 to 4 carbon atoms, an alkoxy group with 1 to 6 carbon atoms, a haloalkoxy group with 1 to 4 carbon atoms, a methylenedioxy group, a cyano group, a nitro group, an amino group, an acylamino group with 1 to 6 carbon atoms (a nitrogen atom of said group may be substituted with an alkyl group having 1 to 4 carbon atoms), a haloalkylcarbonylamino group with 1 to 5 carbon atoms (a nitrogen atom of said group may be substituted with an alkyl group having 1 to 4 carbon atoms), an alkylsulfonylamino group with 1 to 6 carbon atoms (a nitrogen atom of said group may be substituted with an alkyl group having 1 to 4 carbon atoms) or a haloalkylsulfonylamino group with 1 to 4 carbon atoms (a nitrogen atom of said group may be substituted with an alkyl group having 1 to 4 carbon atoms).

(2) The difluoroalkene derivative or the pharmacologically acceptable salt thereof in accordance with the above invention (1), wherein Q represents a hetero ring shown by $Q^1$ to $Q^{37}$:

$Q^1$

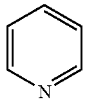

$Q^2$

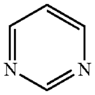

$Q^3$

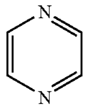

$Q^4$

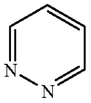

-continued $Q^5$

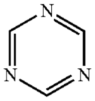

$Q^6$

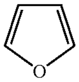

$Q^7$

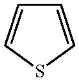

$Q^8$

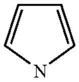

$Q^9$

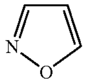

$Q^{10}$

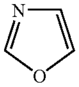

$Q^{11}$

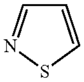

$Q^{12}$

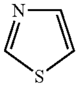

$Q^{13}$

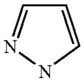

$Q^{14}$

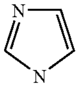

$Q^{15}$

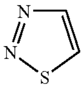

$Q^{16}$

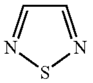

$Q^{17}$

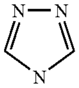

$Q^{18}$

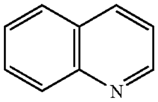

$Q^{19}$

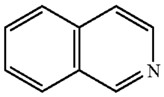

-continued
Q[20]
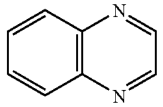
Q[21]
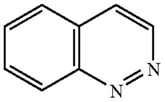
Q[22]
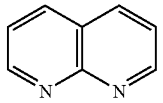
Q[23]
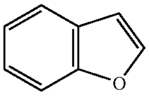
Q[24]
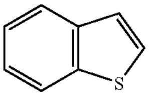
Q[25]
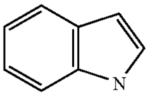
Q[26]
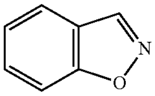
Q[27]
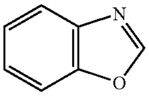
Q[28]
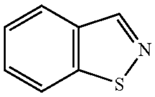
Q[29]
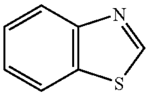
Q[30]
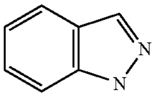
Q[31]
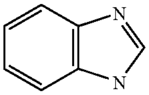
Q[32]
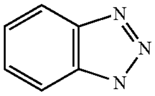
Q[33]
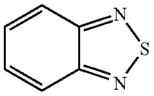
-continued
Q[34]
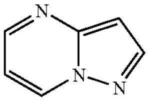
Q[35]
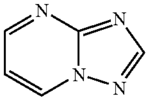
Q[36]
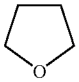
Q[37]
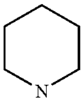
(3) The difluoroalkene derivative or the pharmacologically acceptable salt thereof in accordance with the above invention (1), wherein $L^1$ and $L^2$ each is an oxygen atom; n is an integer of 2 to 4; and Q is $Q^1$ to $Q^{37}$:
Q[1]
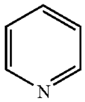
Q[2]
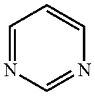
Q[3]
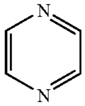
Q[4]
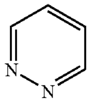
Q[5]
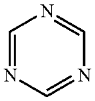
Q[6]
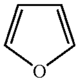
Q[7]
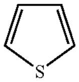
Q[8]
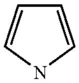

-continued
$Q^9$
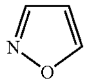
$Q^{10}$
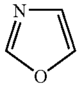
$Q^{11}$
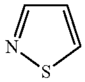
$Q^{12}$
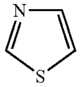
$Q^{13}$
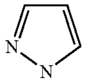
$Q^{14}$
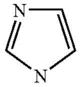
$Q^{15}$
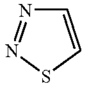
$Q^{16}$
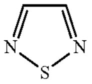
$Q^{17}$
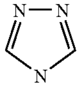
$Q^{18}$
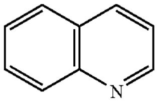
$Q^{19}$
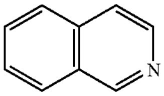
$Q^{20}$
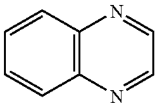
$Q^{21}$
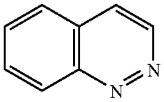
$Q^{22}$
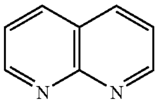
$Q^{23}$
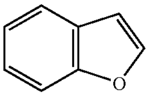
-continued
$Q^{24}$
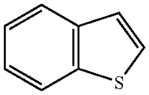
$Q^{25}$
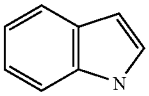
$Q^{26}$
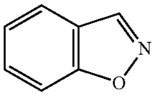
$Q^{27}$
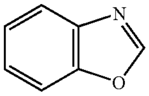
$Q^{28}$
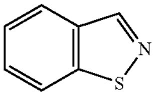
$Q^{29}$
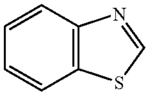
$Q^{30}$
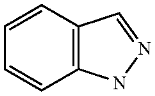
$Q^{31}$
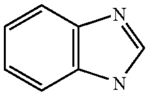
$Q^{32}$
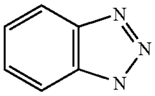
$Q^{33}$
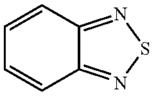
$Q^{34}$
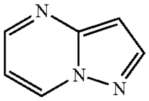
$Q^{35}$
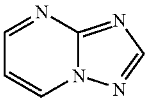
$Q^{36}$
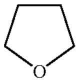
$Q^{37}$
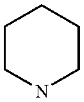

(4) The difluoroalkene derivative or the pharmacologically acceptable salt thereof in accordance with the above invention (1), wherein $L^1$ and $L^2$ each is an oxygen atom; n is an integer of 2 to 4; and Q is $Q^1$, $Q^2$, $Q^{12}$, $Q^{13}$ or $Q^{24}$:

$Q^1$

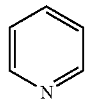

$Q^2$

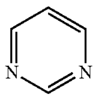

$Q^{12}$

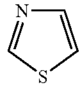

$Q^{13}$

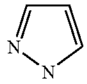

$Q^{24}$

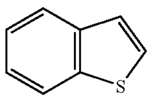

(5) The difluoroalkene derivative or the pharmacologically acceptable salt thereof in accordance with the above invention (1), wherein $L^1$ and $L^2$ each is an oxygen atom; n is an integer of 2 to 4; and Q is $Q^1$, $Q^2$, $Q^{12}$, $Q^{13}$ or $Q^{24}$:

$Q^1$

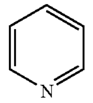

$Q^2$

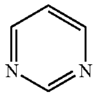

$Q^{12}$

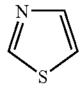

$Q^{13}$

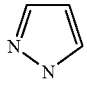

$Q^{24}$

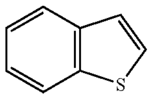

wherein Q may be substituted with 1 to 3 the same or different substituents group X;

X is a halogen atom, an alkyl group having 1 to 6 carbon atoms, an alkoxy group having 1 to 6 carbon atoms, an alkylthio group having 1 to 6 carbon atoms, a haloalkoxy group having 1 to 6 carbon atoms, an alkenyloxy group having 3 to 6 carbon atoms, a haloalkenyloxy group having 3 to 6 carbon atoms, an alkynyloxy group having 3 to 6 carbon atoms, a cycloalkyl group having 3 to 6 carbon atoms, a cycloalkyloxy group having 3 to 7 carbon atoms, a phenyl group (said group may be substituted with a haloalkyl group having 1 to 4 carbon atoms), a benzyl group, a phenoxy group, a phenylthio group, a phenylamino group (a nitrogen atom of said group may be substituted with an alkyl group having 1 to 4 carbon atoms or an alkynyl group having 3 to 4 carbon atoms), an alkylamino group having 1 to 6 carbon atoms (a nitrogen atom of said group may be substituted with an alkyl group having 1 to 6 carbon atoms or an alkynyl group having 3 to 4 carbon atoms, an acyl group having 1 to 5 carbon atoms or a haloalkylcarbonyl group having 2 to 5 carbon atoms), a cycloalkylamino group having 3 to 6 carbon atoms (a nitrogen atom of said group may be substituted with an alkyl group having 1 to 6 carbon atoms), an alkoxyamino group having 1 to 6 carbon atoms (a nitrogen atom of said group may be substituted with an alkyl group having 1 to 6 carbon atoms), a benzylamino group (a nitrogen atom of said group may be substituted with an alkyl group having 1 to 6 carbon atoms), a pyrrolidinyl group and a piperidinyl group.

(6) The difluoroalkene derivative or the pharmacologically acceptable salt thereof in accordance with the above invention (1), wherein $L^1$ and $L^2$ each is an oxygen atom; n is an integer of 2 to 4; and Q is $Q^1$:

$Q^1$

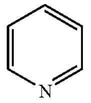

wherein Q may be substituted with 1 to 3 the same or different substituents group X;

X is an alkyl group having 1 to 6 carbon atoms, an alkoxy group having 1 to 6 carbon atoms, an alkylthio group having 1 to 6 carbon atoms, an alkenyloxy group having 3 to 6 carbon atoms, a haloalkenyloxy group having 3 to 6 carbon atoms, an alkynyloxy group having 3 to 6 carbon atoms, a cycloalkyloxy group having 3 to 7 carbon atoms, a phenyl group, a phenoxy group, a phenylthio group and a phenylamino group (a nitrogen atom of said group may be substituted with an alkyl group having 1 to 4 carbon atoms).

(7) The difluoroalkene derivative or the pharmacologically acceptable salt thereof in accordance with the above invention (1), wherein $L^1$ and $L^2$ each is an oxygen atom; n is an integer of 2 to 4; and Q is $Q^2$:

$Q^2$

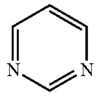

wherein Q may be substituted with 1 to 3 the same or different substituents group X;

X is an alkyl group having 1 to 6 carbon atoms, an alkoxy group having 1 to 6 carbon atoms, a haloalkoxy group having 1 to 6 carbon atoms, a phenyl group (said group may be substituted with a haloalkyl group having 1 to 4 carbon atoms), a phenoxy group, a phenylthio group, a phenylamino group (a nitrogen atom of said group may be substituted with an alkyl group having 1 to 4 carbon atoms or an alkynyl group having 3 to 4 carbon atoms), an alkylamino group having 1 to 6 carbon atoms (a nitrogen atom of said group may be substituted with an alkyl group having 1 to 6 carbon atoms, an alkynyl group having 3 to 4 carbon atoms, an acyl group having 1 to 5 carbon atoms or a haloalkylcarbonyl group having 2 to 5 carbon atoms), a cycloalkylamino group having 3 to 6 carbon atoms (a nitrogen atom of said group may be substituted with an alkyl group having 1 to 6 carbon atoms), an alkoxyamino group having 1 to 6 carbon atoms (a nitrogen atom of said group may be substituted with an alkyl group having 1 to 6 carbon atoms), a benzylamino group (a nitrogen atom of said group may be substituted with an alkyl group having 1 to 6 carbon atoms), a pyrrolidinyl group or a piperidinyl group.

(8) The difluoroalkene derivative or the pharmacologically acceptable salt thereof in accordance with the above invention (1), wherein $L^1$ and $L^2$ each is an oxygen atom; n is an integer of 2 to 4; and Q is $Q^{12}$:

$Q^{12}$

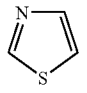

wherein Q may be substituted with 1 to 2 the same or different substituents group X;

X is an alkyl group having 1 to 6 carbon atoms, a cycloalkyl group having 3 to 6 carbon atoms, a phenyl group, a phenylamino group (a nitrogen atom of said group may be substituted with an alkyl group having 1 to 4 carbon atoms) or a benzyl group.

(9) The difluoroalkene derivative or the pharmacologically acceptable salt thereof in accordance with the above invention (1), wherein $L^1$ and $L^2$ each is an oxygen atom; n is an integer of 2 to 4; and Q is $Q^{13}$:

$Q^{13}$

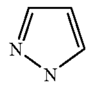

wherein Q may be substituted with 1 to 3 the same or different substituents group X;

X is a halogen atom, an alkyl group having 1 to 6 carbon atoms or a phenyl group.

(10) The difluoroalkene derivative or the pharmacologically acceptable salt thereof in accordance with the above invention (1), wherein $L^1$ and $L^2$ each is an oxygen atom; n is an integer of 2 to 4; and Q is $Q^{24}$:

$Q^{24}$

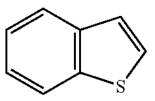

wherein Q may be substituted with 1 to 3 the same or different substituents group X;

X is a halogen atom, an alkyl group having 1 to 6 carbon atoms or an alkoxy group having 1 to 6 carbon atoms.

(11) A difluoroalkenylsulfonate derivative shown by the following formula [2], as a useful manufacturing intermediate for the difluoroalkene derivative in accordance with the above inventions (1) to (10):

[2]

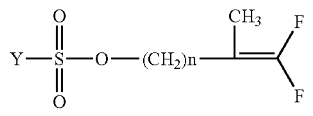

wherein n is an integer of 2 to 8; and Y represents a lower alkyl group or a phenyl group which may be substituted.

(12) A difluoroalkenate ester derivative shown by the following formula [3] as a useful manufacturing intermediate for the difluoroalkene derivative in accordance with the above inventions (1) to (11):

[3]

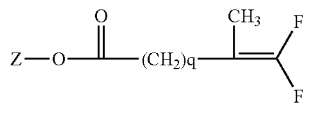

wherein q represents an integer of 3 to 7; and Z represents a methyl group or an ethyl group.

(13) A difluoroalkenyldithiocarbamate derivative shown by the following formula [4], as a useful manufacturing intermediate for a difluoroalkene derivative in accordance with the above inventions (1) and (2):

[4]

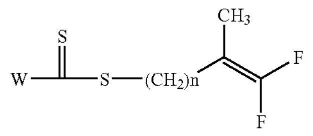

wherein n represents an integer of 2 to 8; and W represents a dimethylamino group or a diethyl amino group.

(14) A carboxylic acid derivative or a salt thereof shown by the following formula [A], as a useful manufacturing intermediate for the difluoroalkene derivative in accordance with the above inventions (1) to (6):

[A]

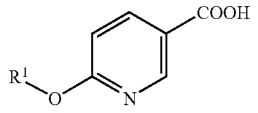

wherein $R^1$ represents an alkynyl group having 3 to 6 carbon atoms or a cycloalkyl group having 3 to 7 carbon atoms.

(15) A carboxylic acid derivative shown by the following formula [B] or [C] or a salt thereof, as a useful manufacturing intermediate for the difluoroalkene derivative in accordance with the above inventions (1) to (5) and (7):

[B]

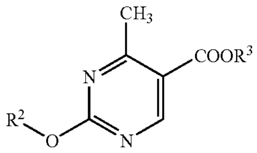

[C]

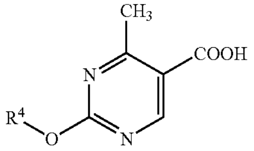

wherein $R^2$ represents an alkyl group having 2 to 12 carbon atoms [said group may be substituted with a phenyl group (said group may be substituted with the same or different 1 to 4 groups selected from a group consisting of a halogen atom, an alkyl group having 1 to 6 carbon atoms, a haloalkyl group having 1 to 4 carbon atoms or an alkoxy group having 1 to 6 carbon atoms), a phenoxy group (said group may be substituted with the same or different 1 to 4 groups selected from a group consisting of a halogen atom, an alkyl group having 1 to 6 carbon atoms, a haloalkyl group having 1 to 4 carbon atoms or an alkoxy group having 1 to 6 carbon atoms) or a cyano group], a haloalkyl group having 1 to 4 carbon atoms, an alkoxyalkyl group having 2 to 6 carbon atoms, an alkenyl group having 3 to 6 carbon atoms, a haloalkenyl group having 3 to 6 carbon atoms, an alkynyl group having 3 to 6 carbon atoms, a cycloalkyl group having 3 to 7 carbon atoms, a cycloalkylalkyl group having 4 to 7 carbon atoms (said group may be substituted with a halogen atom or an alkyl group), a phenyl group (said group may be substituted with the same or different 1 to 4 groups selected from a group consisting of a halogen atom, an alkyl group having 1 to 6 carbon atoms, a haloalkyl group having 1 to 4 carbon atoms or an alkoxy group having 1 to 6 carbon atoms), a benzyl group (said group may be substituted with the same or different 1 to 4 groups selected from a group consisting of a halogen atom, an alkyl group having 1 to 6 carbon atoms, a haloalkyl group having 1 to 4 carbon atoms or an alkoxy group having 1 to 6 carbon atoms) or a pyridyl group (said group may be substituted with the same or different 1 to 4 groups selected from a group consisting of a halogen atom or an alkyl group having 1 to 6 carbon atoms, a haloalkyl group having 1 to 4 carbon atoms or an alkoxy group having 1 to 6 carbon atoms);

$R^3$ represents an alkyl group having 1 to 6 carbon atoms or a benzyl group; and $R^4$ represents an alkyl group having 1 to 12 carbon atoms [said group may be substituted with a phenyl group (said group may be substituted with the same or different 1 to 4 groups selected from a group consisting of a halogen atom, an alkyl group having 1 to 6 carbon atoms, a haloalkyl group having 1 to 4 carbon atoms or an alkoxy group having 1 to 6 carbon atoms), a phenoxy group (said group may be substituted with the same or different 1 to 4 groups selected from a group consisting of a halogen atom, an alkyl group having 1 to 6 carbon atoms, a haloalkyl group having 1 to 4 carbon atoms or an alkoxy group having 1 to 6 carbon atoms) or a cyano group], a haloalkyl group having 1 to 4 carbon atoms, an alkoxyalkyl group having 2 to 6 carbon atoms, an alkenyl group having 3 to 6 carbon atoms, a haloalkenyl group having 3 to 6 carbon atoms, an alkynyl group having 3 to 6 carbon atoms, a cycloalkyl group having 3 to 7 carbon atoms, a cycloalkylalkyl group having 4 to 7 carbon atoms (said group may be substituted with a halogen atom or an alkyl group), a phenyl group (said group may be substituted with the same or different 1 to 4 groups selected from a group consisting of a halogen atom, an alkyl group having 1 to 6 carbon atoms, a haloalkyl group having 1 to 4 carbon atoms or an alkoxy group having 1 to 6 carbon atoms), or a pyridyl group (said group may be substituted with the same or different 1 to 4 groups selected from a group consisting of a halogen atom, an alkyl group having 1 to 6 carbon atoms, a haloalkyl group having 1 to 4 carbon atoms or an alkoxy group having 1 to 6 carbon atoms).

(16) A pest control agent containing, as an effective ingredient, the difluoroalkene or the pharmacologically acceptable salt thereof in accordance with the above inventions (1) to (10).

BEST MODE FOR CARRYING OUT THE INVENTION

The terms used in the present specification are explained by the following examples.

A halogen atom represents a fluorine atom, a chlorine atom, a bromine atom and an iodine atom.

An alkyl group having 1 to 12 carbon atoms is, unless specifically limited, a linear or branched chain alkyl group having 1 to 12 carbon atoms, preferably 1 to 7 carbon atoms, and includes, for example, a methyl group, an ethyl group, a n-propyl group, an isopropyl group, a n-butyl group, an iso-butyl group, a sec-butyl group, a tert-butyl group, a n-penthyl group, an isopentyl group, a neopenthyl group, a n-hexyl group, an isohexyl group, a 3,3-dimethylbutyl group, and the like.

A haloalkyl group having 1 to 4 carbon atoms is, unless specifically limited, a linear or branched chain alkyl group substituted with the same or different 1 to 9 halogen atoms, and includes, for example, a fluoromethyl group, a chloromethyl group, a bromomethyl group, a difluoromethyl group, a trifluoromethyl group, a 2-fluoroethyl group, a 2,2-difluoroethyl group, a 2,2,2-trifluoroethyl group, apenta-fluoroethyl group, and the like.

An alkoxyalkyl group having 2 to 6 carbon atoms is an alkyl group having 2 to 6 carbon atoms, which has an oxygen atom in said carbon chain to form carbon-oxygen-carbon bond, and includes, for example, a methoxymethyl group, a methoxyethyl group, an ethoxymethyl group, an isopropoxymethyl group, a tert-butoxymethyl group, and the like.

An alkenyl group having 2 to 6 carbon atoms represents a linear or branched chain alkenyl group, and includes, for example, an ethenyl group, a 1-propenyl group, a 2-propenyl group, an isopropenyl group, a 1-butenyl group, a 2-butenyl group, a 3-butenyl group, a 2-pentenyl group, and the like.

A haloalkenyl group having 2 to 7 carbon atoms is, unless specifically limited, a linear or branched chain alkenyl group substituted with same or different 1 to 4 halogen atoms, and includes, for example, 3-chloro-2-propenyl group, a 2-chloro-2-propenyl group, a 6,6-difluoro-5-methyl-5-hexenyl group, and the like.

An alkynyl group having 2 to 6 carbon atoms represents a linear or branched chain alkynyl group, and includes, for example, an ethynyl group, a 2-propynyl group, a 2-methyl-2-propynyl group, a 2-butynyl group, a 3-butynyl group, a 2-methyl-3-butynyl group, a phenylethynyl group, and the like. These alkynyl groups may be mono-substituted with any group selected from substituents group α.

A cycloalkyl group having 3 to 6 carbon atoms includes, for example, a cyclopropyl group, a cyclobutyl group, a cyclopentyl group, a cyclohexyl group, and the like.

A cycloalkylalkyl group having 4 to 7 carbon atoms is, unless specifically limited, an alkyl group having 1 to 4 carbon atoms, preferably 1 to 3 carbon atoms which are substituted with a cycloalkyl group having 3 to 6 carbon atoms, and includes, for example, a cyclopropylmethyl group, a 1-cyclopropylethyl group, a 2-cyclopropylethyl group, a 1-cyclopropylpropyl group, a 2-cyclopropylpropyl group, a 3-cyclopropylpropyl group, a cyclobutylmethyl group, a cyclopentylmethyl group, a cyclohexylmethyl group, and the like. These cycloalkylalkyl groups having 4 to 7 carbon atoms may be substituted, at said cycloalkyl group moiety or said alkyl group moiety, with a halogen atom or an alkyl group having 1 to 12 carbon atoms, preferably 1 to 6 carbon atoms, and a cycloalkylalkyl group having such substituents group includes, for example, a 2-chlorocyclopropylmethyl group, a 2,2-dichlorocyclopropylmethyl group, a 2-fluorocyclopropylmethyl group, a 2,2-difluorocyclopropylmethyl group, a 2-methylcyclopropylmethyl group, a 2,2-dimethylcyclopropylmethyl group, a 2-methylcyclopropylethyl group, and the like.

An alkoxy group having 1 to 12 carbon atoms represents an (alkyl)-O— group, wherein an alkyl moiety consists of a linear or branched chain alkyl group having 1 to 12 carbon atoms, preferably 1 to 8 carbon atoms, and includes, for example, a methoxy group, an ethoxy group, a n-propoxy group, an isopropoxy group, a tert-butoxy group, a n-butoxygroup, a sec-butoxy group, an isobutoxy group, a n-hexyloxy group, a n-octyloxy group, and the like.

A haloalkoxy group having 1 to 6 carbon atoms represents a (haloalkyl)-O— group, wherein a haloalkyl moiety consists of a linear or branched chain alkyl group having 1 to 6 carbon atoms, preferably 1 to 4 carbon atoms, substituted with the same or different 1 to 9 halogen atoms, and includes, for example, a difluoromethoxy group, a trifluoromethoxy group, a 2-fluoroethoxy group, a 2,2-difluoroethoxy group, a 2,2,2-trifluoroethoxy group, a 4-chlorobutoxy group, and the like.

An alkoxyalkyloxy group having 2 to 6 carbon atoms represents a (alkoxyalkyl)-O— group, wherein an alkoxyalkyl moiety is defined as described above, and includes, for example, a methoxymethoxy group, a methoxyethoxy group, a n-propoxyethoxy group, a n-butoxyethoxy group, and the like.

An alkenyloxy group having 3 to 8 carbon atoms represents an (alkenyl)-O— group wherein an alkenyl moiety is a linear or branched chain alkenyl group having 3 to 8 carbon atoms, preferably 3 to 6 carbon atoms, and includes, for example, a 2-propenyloxy group, a 2-butenyloxy group, a 5-hexenyloxy group, and the like.

A haloalkenyloxy group having 3 to 8 carbon atoms represents a (haloalkenyl)-O— group wherein an alkenyl moiety is a linear or branched chain alkenyl group having 3 to 8 carbon atoms, preferably 3 to 6 carbon atoms, substituted with the same or different 1 to 9 halogen atoms, preferably 1 to 3 halogen atoms, and includes, for example, a 3-chloro-2-propenyloxy group, a 6,6-difluoro-5-methyl-5-hexenyloxy group, and the like.

An alkynyloxy group having 3 to 6 carbon atoms represents an (alkynyl)-O- group wherein an alkynyl moiety is a linear or branched chain alkynyl group having 3 to 8 carbon atoms, preferably 3 to 6 carbon atoms, and includes, for example, a 2-propynyloxy group, a 2-butynyloxy group, and the like.

A cycloalkyloxy group having 3 to 7 carbon atoms represents a (cycloalkyl)-O— group wherein a cycloalkyl moiety is defined as described above, and includes, for example, a cyclopropyloxy group, a cyclobutyloxy group, a cyclopentyloxy group, a cyclohexyloxy group, a cyclopentyloxy group, and the like.

A cycloalkylalkyloxy group having 4 to 7 carbon atoms represents a (cycloalkylalkyl)-O— group, wherein a cycloalkylalkyl moiety is defined as described above, and includes, for example, a cyclopropylmethoxy group, a 1-cyclopropylethoxy group, a 2-cyclopropylethoxy group, a 3-cyclopropylpropoxy group, a cyclobutylmethoxy group, a cyclopentylmethoxy group, a cyclohexylmethoxy group, etc. These cycloalkylalkyloxy group having 4 to 7 carbon atoms may be substituted, at said cycloalkyl group moiety or a alkyl group moiety, with a halogen atom or an alkyl group having 1 to 12 carbon atoms, preferably 1 to 6 carbon atoms and a cycloalkylalkyloxy group having such substituents group includes, for example, a 2,2-dichlorocyclopropylmethoxy group, a 2,2-difluorocyclopropylmethoxy group, a 2-methylcyclopropylmethoxy group, a 2,2-dimethylcyclopropylmethoxy group, and the like.

An alkylthio group, an alkylsulfinyl group and an alkylsulfonyl group having 1 to 12 carbon atoms, represent a (alkyl)-S— group, (alkyl)-SO— group, (alkyl)-$SO_2$-group, wherein an alkyl moiety is defined as described above, and includes, for example, a methylthio group, an ethylthio group, a n-propylthio group, an isopropylthio group, a methylsulfinyl group, a methylsulfonyl group, an ethylsulfonyl group, a n-propylsulfonyl group, an isopropylsulfonyl group, and the like.

An acyl group having 1 to 6 carbon atoms represents an aliphatic acyl group consisted of a linear or branched chain alkyl group having 1 to 6 carbon atoms, preferably 1 to 4 carbon atoms or a formyl group, and includes, for example, a formyl group, an acetyl group, a propionyl group, an isopropionyl group, a butylyl group, a pivaloyl group, and the like.

An acyloxy group having 1 to 6 carbon atoms represents an (acyl)-O— group, wherein an acyl moiety is defined as described above, and includes, for example, an acetyloxy group, a propionyloxy group, an isopropionyloxy group, a pivaroyloxy group, and the like.

A haloalkylcarbonyl group having 1 to 5 carbon atoms represents a (haloalkyl)-CO— group, wherein a haloalkyl moiety is defined as described above, and includes, for example, a chloroacetyl group, a trifluoroacetyl group, a pentafluoropropionyl group, and the like.

An alkoxycarbonyl group having 1 to 6 carbon atoms represents an (alkyl)-O—(C═O)— group, wherein an alkyl moiety is defined as described above, and includes, for example, a methoxycarbonyl group, an ethoxycarbonyl group, a n-propoxycarbonyl group, an isopropoxycarbonyl group, and the like.

A carbamoyl group (a nitrogen atom of said group may be substituted with the same or different alkyl group having 1 to 4 carbon atoms), and includes, for example, a methylcarbamoyl group, an isopropylcarbamoyl group, a dimethylcarbamoyl group, a diethylcarbamoyl group, and the like.

A substituted or non-substituted amino group in the present invention may be further substituted at the nitrogen atom of said amino group, if necessary, in the range not to provide serious effects on activity and safety, with a substituted or non-substituted alkyl group having 1 to 4 carbon atoms, a substituted or non-substituted alkenyl group having 2 to 4 carbon atoms, a substituted or non-substituted alkynyl group having 3 to 4 carbon atoms, a substituted or non-substituted acyl group having 1 to 4 carbon atoms, a substituted or non-substituted alkoxycarbonyl group having 2 to 4 carbon atoms, an N-substituted or non N-substituted carbamoyl group or a substituted or non-substituted alkylsulfonyl group having 1 to 4 carbon atoms. Such a substituted or non-substituted amino group includes, for example, an amino group, a phenylamino group, an alkylamino group, a cycloalkylamino group, an alkoxyamino group, an acylamino group, a haloalkylcarbonylamino group, an alkylsulfonylamino group, a haloalkylsulfonylamino group, and the like.

A nitrogen atom of an amino group of a phenylamino group may be further substituted, and such an N-substituted or non N-substituted phenylamino group includes a group shown by the formula (phenyl)-N— ($R^{11}$)—(wherein $R^1$ represents a hydrogen atom, an alkyl group having 1 to 4 carbon atoms, an alkenyl group having 2 to 4 carbon atoms, an alkynyl group having 3 to 4 carbon atoms, an acyl group having 1 to 4 carbon atoms, an alkoxycarbonyl group having 2 to 4 carbon atoms or a carbamoyl group whose nitrogen atom may be substituted with same or different alkyl group having 1 to 4 carbon atoms). An N-substituted or non N-substituted phenylamino group includes, for example, a phenylamino group, an N-methyl-N-phenylamino group, an N-ethyl-N-phenylamino group, an N-phenyl-N-2-propenylamino group, an N-phenyl-N-2-propynylamino group, an N-acetyl-N-phenylamino group, an N-tery-butoxycarbonyl-N-4-tolylamino group, a 3,3-dimethyl-1-(4-tolyl)ureido group, and the like. These N-substituted or non-substituted phenylamino groups may further be substituted with any 1 to 4 groups selected from substituents group β.

An alkylamino group having 1 to 12 carbon atoms is an alkylamino group consisting of a linear or branched chain alkyl group having 1 to 12 carbon atoms, preferably 1 to 8 carbon atoms, and the nitrogen atom of said amino group may further be substituted, and such an N-substituted or non N-substituted alkylamino group includes a group shown by the formula (alkyl)-N—($R^{12}$)—(wherein $R^{12}$ represents a hydrogen atom, an alkyl group having 1 to 6 carbon atoms which may be mono-substituted with any group selected from substituents group α, an alkenyl group having 2 to 4 carbon atoms, an alkynyl group having 3 to 4 carbon atoms or a hydroxyl group), for example, a methylamino group, an isopropylamino group, a n-buthylamino group, a n-hexylamino group, a dimethylamino group, a diethylamino group, a dibutylamino group, an isopropylmethylamino group, a n-butylmethylamino group, a n-hexylmethylamino group, a methyl-2-propenylamino group, a methyl-2-propynylamino group, and the like. These N-substituted or non-substituted alkylamino groups may be mono-substituted with any group selected from substituents group α, and includes, for example a benzylmethylamino group.

A cycloalkylamino group having 1 to 6 carbon atoms is a cycloalkylamino group whose cycloalkyl moiety is defined as described above and the nitrogen atom of said amino group may further be substituted, and such an N-substituted or non N-substituted cycloalkylamino group includes a group shown by the formula (cycloalkyl)-N—($R^{13}$)-(wherein $R^{13}$ represents a hydrogen atom, an alkyl group having 1 to 6 carbon atoms, an alkenyl group having 2 to 4 carbon atoms, an alkynyl group having 3 to 4 carbon atoms, an acyl group having 1 to 4 carbon atoms, an alkoxycarbonyl group having 2 to 4 carbon atoms or an alkylsulfonyl group having 1 to 4 carbon atoms) including, for example, a cyclohexylamino group, an N-cyclopropyl-N-methylamino group, an N-cyclohexyl-N-methylamino group, an N-acetyl-N-cyclohexylamino group, an N-cyclohexyl-N-methanesulfonylamino group, and the like.

An alkoxyamino group having 1 to 12 carbon atoms is an alkoxyamino group having a linear or branched chain alkoxy group having 1 to 12 carbon atoms, preferably 1 to 8 carbon atoms, wherein the nitrogen atom of said amino group may further be substituted, and such an N-substituted or non N-substituted alkoxyamino group includes a group shown by the formula (alkoxy)-N—($R^{14}$)— (wherein $R^{14}$ represents a hydrogen atom, an alkyl group having 1 to 10 carbon atoms which may be mono-substituted with any group selected from substituents group α, an alkenyl group having 2 to 4 carbon atoms, an alkynyl group having 3 to 4 carbon atoms, an acyl group having 1 to 4 carbon atoms, an alkoxycarbonyl group having 2 to 4 carbon atoms or an alkylsulfonyl group having 1 to 4 carbon atoms) including, for example, a methoxyamino group, an N-n-butoxy-N-methylamino group, an N-benzyloxy-N-methylamino group, an N-acetyl-N-n-hexyloxyamino group, an N-n-butyl-N-methoxyamino group, and the like. These N-substituted or non N-substituted alkoxyamino groups may be mono-substituted, at alkoxy group moiety, with any group selected from substituents group α.

An acylamino group having 1 to 6 carbon atoms (the nitrogen atom of said group may be substituted with an alkyl group having 1 to 6 carbon atoms) represents an (acyl)-N($R^{15}$)— group wherein acyl moiety is defined as described above, and $R^{15}$ is a hydrogen atom or an alkyl group having 1 to 6 carbon atoms, and includes, for example, an acetylamino group, an N-methylacetamide group, an N-butylacetamide group, a propyonylamino group, an isopropyonylamino group, a pivaloylamino group, and the like.

A haloalkylcarbonylamino group having 1 to 5 carbon atoms (the nitrogen atom of said group may be substituted with an alkyl group having 1 to 6 carbon atoms) represents a (haloalkyl)-C(═O)N($R^{15}$)-group, wherein haloalkyl moiety and $R^{15}$ are defined as described above, and includes, for example, a chloroacetylamino group, a trichloroacetylamino group, a trifluoroacetylamino group, an N-methyltrifluoroacetamide group, an N-butyltrifluoroacetamide group, a pentafluoropropionylamino group, and the like.

An alkylsulfonylamino group having 1 to 6 carbon atoms (the nitrogen atom of said group may be substituted with an alkyl group having 1 to 6 carbon atoms) represents an (alkyl)-$SO_2N(R^{15})$— group wherein alkyl moiety and $R^{15}$ are defined as described above, and includes, for example, a methanesulfonylamino group, an N-methylmethanesulfoneamide group, an N-butyl methanesulfoneamide group, an ethanesulfonylamino group, an isopropylsulfonylamino group, a 1-butanesulfonylamino group, and the like.

A haloalkylsulfonylamino group having 1 to 4 carbon atoms (the nitrogen atom of said group may be substituted with an alkyl group having 1 to 6 carbon atoms) represents a (haloalkyl)-$SO_2N(R^{15})$— group wherein haloalkyl moiety and $R^{15}$ are defined as described above, and includes, for example, a chloromethanesulfonylamino group, an N-methylchloromethanesulfoneamide group, an N-butylchloromethanesulfoneamide group, a chloroethanesulfoneamino group, a difluoromethanesulfonylamino group, a trifluoromethanesulfonylamino group, a 2,2,2-triifluoroethanesulfonylamino group, and the like.

A 5- to 12-membered heterocyclic group having any hetero atom selected from a nitrogen atom, an oxygen atom and a sulfur atom is a monocyclic, polycyclic or condesed cyclic group having 1 or 2 hetero rings of each 5- to 8-membered, preferably 5- to 6-membered ring, with same or different 1 to 4, preferably 1 to 3 hetero atoms selected from a nitrogen atom, an oxygen atom or a sulfur atom, in a ring, and a preferable heterocyclic group includes, for example, a pyridyl group, a pyrimidinyl group, a pyrazinyl group, a pyridazinyl group, a triazinyl group, a furyl group, a thienyl group, a pyrrolyl group, an isoxazolyl group, an oxazolyl group, an isothiazolyl group, a thiazolyl group, a pyrazolyl group, an imidazolyl group, a thiadiazolyl group, a triazolyl group, an oxadiazolyl group, a tetrazolyl group, a quinolyl group, an isoquinolyl group, a quinoxalinyl group, a cinnolinyl group, a phthalazinyl group, a quinazolinyl group, a naphthyridinyl group, a benzofuryl group, a benzothienyl group, a indolyl group, a benzoisoxazolyl group, a benzoxazolyl group, a benzoisothiazolyl group, a benzothiazolyl group, an indazolyl group, a benzoimidazolyl group, a benzotriazolyl group, a benzothiadiazolyl group, a pyrazolopyrimidinyl group, a triazolopyrimidinyl group, a purinyl group, a tetrahydrofuryl group, a tetrahydropiranyl group, a pyrrolidinyl group, a piperidinyl group, and the like.

A pharmacologically acceptable salt in a compound shown by the general formula [1], is a salt between a hydroxyl group, a carboxyl group, an amino group, or the like, when present in the structure, and a metal or an organic base or a salt between these and a mineral acid or an organic acid, and a metal includes an alkali metal such as sodium and potassium; an alkali earth metal such as magnesium and calcium, and an organic base includes triethylamine and diisopropylamine, while a mineral acid includes hydrochloric acid and sulfuric acid, and an organic acid includes acetic acid, methanesulfonic acid and p-toluene sulfonic acid.

A compound shown by the general formula [1] includes one wherein the above-described various substituents group are combined, and preferable one in view of medicinal effect includes the followings:

(1) a compound wherein Q is $Q^1$, X is a chlorine atom, $L^1$ and $L^2$ are oxygen atoms, and n is 4.

(2) a compound wherein Q is $Q^2$, X is a dimethoxy group, $L^1$ and $L^2$ are oxygen atoms, and n is 4 or 6.

(3) a compound wherein Q is $Q^7$, X is a methyl group, $L^1$ and $L^2$ are oxygen atoms, and n is 2 or 4.

(4) a compound wherein Q is $Q^8$, X is a hydrogen atom or a methyl group, $L^1$ and $L^2$ are oxygen atoms, and n is 4 or 6.

(5) a compound wherein Q is $Q^9$, X is a methyl group or a phenyl group, $L^1$ and $L^2$ are oxygen atoms, and n is 2 or 4.

(6) a compound wherein Q is $Q^{12}$, X is a methyl group or a phenyl group, $L^1$ and $L^2$ are oxygen atoms, and n is 2 or 4.

(7) a compound wherein Q is $Q^{13}$, X is a methyl group, an ethyl group and a chlorine atom, $L^1$ and $L^2$ are oxygen atoms, and n is 2 or 4.

(8) a compound wherein Q is $Q^{18}$, X is a hydrogen atom, $L^1$ and $L^2$ are oxygen atoms, and n is 2 or 4.

(9) a compound wherein Q is $Q^{23}$, X is a hydrogen atom, $L^1$ and $L^2$ are oxygen atoms, and n is 2 or 4.

(10) a compound wherein Q is $Q^{24}$, X is a hydrogen atom, $L^1$ is an oxygen atom or a sulfur atom, $L^2$ is an oxygen atom, and n is 2 or 4.

(11) a compound wherein Q is $Q^{24}$, X is a chlorine atom, $L^1$ and $L^2$ are oxygen atoms, and n is 2 or 4.

(12) a compound wherein Q is $Q^{25}$, X is a hydrogen atom or a methyl group, $L^1$ and $L^2$ are oxygen atoms, and n is 2 or 4.

(13) a compound wherein Q is $Q^{29}$, X is a hydrogen atom, m is 0, $L^1$ and $L^2$ are oxygen atoms, and n is 2 or 4.

(14) a compound wherein Q is $Q^1$, X is an alkoxy group having 3 to 7 carbon atoms, $L^1$ and $L^2$ are oxygen atoms, and n is 2.

(15) a compound wherein Q is $Q^1$, X is a cycloalkyloxy group having 5 or 6 carbon atoms, $L^1$ and $L^2$ are oxygen atoms, and n is 2.

(16) a compound wherein Q is $Q^1$, X is a phenoxy group, $L^1$ and $L^2$ are oxygen atoms, and n is 2.

(17) a compound wherein Q is $Q^2$, X is a methyl group and a phenyl group, $L^1$ and $L^2$ are oxygen atoms, and n is 2.

(18) a compound wherein Q is $Q^2$, X is an ethyl group and a phenyl group, $L^1$ and $L^2$ are oxygen atoms, and n is 2.

(19) a compound wherein Q is $Q^2$, X is a methyl group and an alkoxy group having 3 to 6 carbon atoms, $L^1$ and $L^2$ are oxygen atoms, and n is 2.

(20) a compound wherein Q is $Q^2$, X is a methyl group or a benzyl group, $L^1$ and $L^2$ are oxygen atoms, and n is 2.

(21) a compound wherein Q is $Q^2$, X is a methyl group or a phenylamino group whose nitrogen atom is substituted with an alkyl group having 1 to 3 carbon atoms, $L^1$ and $L^2$ are oxygen atoms, and n is 2.

(22) a compound wherein Q is $Q^2$, X is a methyl group and an amino group substituted with the same or different 1 to 2 alkyl groups having 1 to 6 carbon atoms, $L^1$ and $L^2$ are oxygen atoms, and n is 2.

(23) a compound wherein Q is $Q^{12}$, X is a methyl group and a benzyl group, $L^1$ and $L^2$ are oxygen atoms, and n is 2 or 4.

(24) a compound wherein Q is $Q^{12}$, X is a methyl group and an alkyl group having 4 to 6 carbon atoms, $L^1$ and $L^2$ are oxygen atoms, and n is 2.

(25) a compound wherein Q is $Q^{12}$, X is a methyl group and a cycloalkyl group having 5 or 6 carbon atoms, $L^1$ and $L^2$ are oxygen atoms, and n is 2.

(26) a compound wherein Q is $Q^{12}$, X is a methyl group and a phenylamino group whose nitrogen atom is substituted with an alkyl group having 1 to 3 carbon atoms, $L^1$ and $L^2$ are oxygen atoms, and n is 2.

(27) a compound wherein Q is $Q^{13}$, X is a methyl group and a phenyl group, $L^1$ and $L^2$ are oxygen atoms, and n is 2.

(28) a compound wherein Q is $Q^{13}$, X is a methyl group and an alkyl group having 3 to 5 carbon atoms, $L^1$ and $L^2$ are oxygen atoms, and n is 2.

Among these, particularly preferable one includes the followings:

(1) a compound wherein Q is $Q^1$, X is a n-butoxy group, $L^1$ and $L^2$ are oxygen atoms, and n is 2.

(2) a compound wherein Q is $Q^1$, X is a cyclopentyloxy group, L and $L^2$ are oxygen atoms, and n is 2.

(3) a compound wherein Q is $Q^2$, X is a methyl group and a phenyl group, $L^1$ and $L^2$ are oxygen atoms, and n is 2.

(4) a compound wherein Q is $Q^2$, X is a methyl group and a n-butoxy group, $L^1$ and $L^2$ are oxygen atoms, and n is 2.

(5) a compound wherein Q is $Q^2$, X is a methyl group and a benzyl group, $L^1$ and $L^2$ are oxygen atoms, and n is 2.

(6) a compound wherein Q is $Q^2$, X is a methyl group and an N-n-butyl-N-methylamino group, $L^1$ and $L^2$ are oxygen atoms, and n is 2.

(7) a compound wherein Q is $Q^{12}$, X is a methyl group and a phenyl group, $L^1$ and $L^2$ are oxygen atoms, and n is 2.

(8) a compound wherein Q is $Q^{12}$, X is a methyl group and a cyclohexyl group, $L^1$ and $L^2$ are oxygen atoms, and n is 2.

(9) a compound wherein Q is $Q^{12}$, X is a methyl group and an N-methyl—N-phenylamino group, $L^1$ and $L^2$ are oxygen atoms, and n is 2.

(10) a compound wherein Q is $Q^{13}$, X is a methyl group and a phenyl group, $L^1$ and $L^2$ are oxygen atoms, and n is 2.

(11) a compound wherein Q is $Q^{24}$, X is a hydrogen atom, $L^1$ and $L^2$ are oxygen atoms, and n is 4.

Typical examples of a compound of the present invention having the general formula [1] are shown in Table 1 to Table 37. However, a compound of the present invention is by no means limited to these. Numbers of these compounds are referred to hereinafter.

The following expressions in the Tables of the present specification represent the following corresponding groups, respectively:

Me: methyl group

Et: ethyl group

Pr: propyl group

Pr-i: isopropyl group

Pr-c: cyclopropyl group

Bu-t: tert-butyl group

Hex-c: cyclohexyl group

Ph: phenyl group

3-Picolyl: 3-picolyl group

2-Cl-Pyrid-5-yl: 2-chloro-5-pyridyl group

Further, when a compound of the present invention has a hydroxyl group as a substituents group, said compound may include a keto-enol tautomer.

TABLE 1

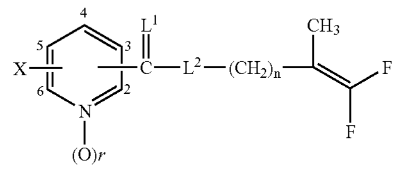

| Bonding position to hetero ring | X | r | $L^1$ | $L^2$ | n |
|---|---|---|---|---|---|
| 2 | H | 0 | O | O | 4 |
| 3 | H | 0 | O | O | 4 |
| 3 | H | 1 | O | O | 4 |
| 3 | H | 0 | O | O | 6 |

TABLE 1-continued

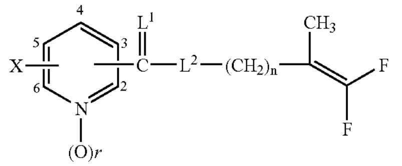

| Bonding position to hetero ring | X | r | $L^1$ | $L^2$ | n |
|---|---|---|---|---|---|
| 3 | H | 0 | O | O | 8 |
| 4 | H | 0 | O | O | 4 |
| 2 | 6-Me | 0 | O | O | 4 |
| 2 | 5-Cl | 0 | O | O | 4 |
| 2 | 3-COPh | 0 | O | O | 4 |
| 2 | 6-OPh | 0 | O | O | 4 |
| 3 | 6-Cl | 0 | O | O | 2 |
| 3 | 6-Cl | 0 | O | O | 4 |
| 3 | 6-Cl | 0 | O | O | 5 |
| 3 | 6-Cl | 0 | O | O | 6 |
| 3 | 6-Cl | 0 | O | O | 8 |
| 3 | 6-Cl | 0 | O | S | 4 |
| 3 | 6-Cl | 0 | S | O | 4 |
| 3 | 2,6-$Cl_2$ | 0 | O | O | 4 |
| 3 | 5,6-$Cl_2$ | 0 | O | O | 4 |
| 3 | 2-COOMe | 0 | O | O | 4 |
| 3 | 2-$COOCH_2$(4-OMe—Ph) | 0 | O | O | 4 |
| 3 | 2-$CONMe_2$ | 0 | O | O | 4 |
| 3 | 2-$CONEt_2$ | 0 | O | O | 4 |
| 3 | 2-CONH(2-Cl-4-$OCHF_2$—Ph) | 0 | O | O | 4 |
| 3 | 2-CON(Me)(2-Cl-4-$OCHF_2$—Ph) | 0 | O | O | 4 |
| 3 | 2-CN | 0 | O | O | 4 |
| 3 | 5-$NO_2$ | 0 | O | O | 4 |
| 3 | 6-OH | 0 | O | O | 4 |
| 3 | 6-OMe | 0 | O | O | 2 |
| 3 | 6-OMe | 0 | O | O | 4 |
| 3 | 6-OMe | 0 | O | O | 6 |
| 3 | 6-OEt | 0 | O | O | 2 |
| 3 | 6-OEt | 0 | O | O | 4 |
| 3 | 6-$O(CH_2)_2C(Me){=}CF_2$ | 0 | O | O | 2 |
| 3 | 6-OPh | 0 | O | O | 2 |
| 3 | 6-OPh | 0 | O | O | 4 |
| 3 | 6-SMe | 0 | O | O | 2 |
| 3 | 6-SMe | 0 | O | O | 4 |
| 3 | 6-SMe | 0 | O | O | 6 |
| 3 | 6-SPh | 0 | O | O | 4 |
| 3 | 6-NH2 | 0 | O | O | 4 |
| 3 | 6-NHCOMe | 0 | O | O | 4 |
| 3 | 6-NHCOPh | 0 | O | O | 4 |
| 3 | 6-NHCO(4-Ph—Ph) | 0 | O | O | 4 |
| 3 | 6-NHCO(3-OPh—Ph) | 0 | O | O | 4 |
| 3 | 6-NHCO(4-$OCH_2$Ph—Ph) | 0 | O | O | 4 |
| 3 | 6-NHCO[4-(Pyrid-2-yl)-Ph] | 0 | O | O | 4 |
| 3 | 6-NHCO[3-(Pyrid-2-yl)-Ph] | 0 | O | O | 4 |
| 3 | 6-$NHSO_2$(4-Me—Ph) | 0 | O | O | 4 |
| 3 | 6-N(Me)$SO_2$(4-Me—Ph) | 0 | O | O | 4 |
| 4 | 2-Cl | 0 | O | O | 4 |
| 4 | 2,6-$Cl_2$ | 0 | O | O | 4 |
| 4 | 2-Ph | 0 | O | O | 4 |
| 4 | 2-OPh | 0 | O | O | 4 |
| 4 | 2-SPh | 0 | O | O | 4 |
| 4 | 2-OEt | 0 | O | O | 4 |
| 3 | 5-(2-Thienyl) | 0 | O | O | 2 |
| 3 | 5-C≡CPh | 0 | O | O | 2 |
| 3 | 6-Ph | 0 | O | O | 2 |
| 3 | 6-Ph | 0 | O | O | 4 |
| 3 | 6-SPh | 0 | O | O | 2 |
| 3 | 6-SOPh | 0 | O | O | 2 |
| 3 | 6-$SO_2$Ph | 0 | O | O | 2 |
| 3 | 6-OPr | 0 | O | O | 2 |
| 3 | 6-OPr | 0 | O | O | 4 |
| 3 | 6-OPr-i | 0 | O | O | 2 |
| 3 | 6-OPr-i | 0 | O | O | 4 |
| 3 | 6-OBu | 0 | O | O | 2 |
| 3 | 6-OBu | 0 | O | O | 4 |
| 3 | 6-OBu-t | 0 | O | O | 2 |
| 3 | 6-OBu-t | 0 | O | O | 4 |

TABLE 1-continued

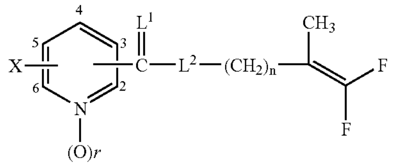

| Bonding position to hetero ring | X | r | $L^1$ | $L^2$ | n |
|---|---|---|---|---|---|
| 3 | 6-$OC_5H_{11}$ | 0 | O | O | 2 |
| 3 | 6-$OC_5H_{11}$ | 0 | O | O | 4 |
| 3 | 6-$OC_5H_9$-c | 0 | O | O | 2 |
| 3 | 6-$OC_5H_9$-c | 0 | O | O | 4 |
| 3 | 6-$OC_6H_{13}$ | 0 | O | O | 2 |
| 3 | 6-$OC_6H_{13}$ | 0 | O | O | 4 |
| 3 | 6-$OC_6H_{11}$-c | 0 | O | O | 2 |
| 3 | 6-$OC_6H_{11}$-c | 0 | O | O | 4 |
| 3 | 6-$OC_7H_{15}$ | 0 | O | O | 2 |
| 3 | 6-$OC_8H_{17}$ | 0 | O | O | 2 |
| 3 | 6-$OC_9H_{19}$ | 0 | O | O | 2 |
| 3 | 6-$OC_{10}H_{21}$ | 0 | O | O | 2 |
| 3 | 6-$OCH_2C{\equiv}CMe$ | 0 | O | O | 2 |
| 3 | 6-$OCH_2C{\equiv}CMe$ | 0 | O | O | 4 |
| 3 | 6-$O(CH_2)_4CH{=}CH_2$ | 0 | O | O | 2 |
| 3 | 6-$O(CH_2)_4CH{=}CH_2$ | 0 | O | O | 4 |
| 3 | 6-$OCH_2CF_3$ | 0 | O | O | 2 |
| 3 | 6-$OCH_2Ph$ | 0 | O | O | 2 |
| 3 | 6-$O(CH_2)_2OPh$ | 0 | O | O | 2 |
| 3 | 6-SEt | 0 | O | O | 2 |
| 3 | 6-SEt | 0 | O | O | 4 |
| 3 | 6-SPr | 0 | O | O | 2 |
| 3 | 6-SPr | 0 | O | O | 4 |
| 3 | 6-SBu | 0 | O | O | 2 |
| 3 | 6-SBu | 0 | O | O | 4 |
| 3 | 6-$SC_5H_{11}$ | 0 | O | O | 2 |
| 3 | 6-$SC_6H_{13}$ | 0 | O | O | 2 |
| 3 | 6-$SOC_6H_{13}$ | 0 | O | O | 2 |
| 3 | 6-$SO_2C_6H_{13}$ | 0 | O | O | 2 |
| 3 | 6-$SC_7H_{15}$ | 0 | O | O | 2 |
| 3 | 6-$SC_8H_{17}$ | 0 | O | O | 2 |
| 3 | 6-NHPh | 0 | O | O | 2 |
| 3 | 6-NHPh | 0 | O | O | 4 |
| 3 | 6-N(Me)Ph | 0 | O | O | 2 |
| 3 | 6-N(Me)Ph | 0 | O | O | 4 |
| 3 | 6-N(Me)COMe | 0 | O | O | 4 |
| 3 | 2-COOMe | 0 | O | O | 2 |
| 2 | 3-CONHPh | 0 | O | O | 2 |
| 3 | 2-CONHPh | 0 | O | O | 2 |
| 3 | 2-$CONEt_2$ | 0 | O | O | 2 |
| 3 | 2-COPh | 0 | O | O | 2 |

TABLE 2

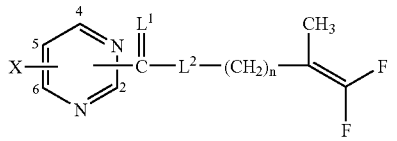

| Bonding position to hetero ring | X | $L^1$ | $L^2$ | n |
|---|---|---|---|---|
| 2 | H | O | O | 4 |
| 2 | 4,6-$Me_2$ | O | O | 2 |
| 2 | 4,6-$Me_2$ | O | O | 4 |
| 2 | 4,6-$Me_2$ | O | O | 6 |
| 2 | 4,6-$(OMe)_2$ | O | O | 2 |
| 2 | 4,6-$(OMe)_2$ | O | O | 4 |
| 2 | 4,6-$(OMe)_2$ | O | O | 5 |
| 2 | 4,6-$(OMe)_2$ | O | O | 6 |
| 2 | 4,6-$(OMe)_2$ | O | O | 8 |

TABLE 2-continued

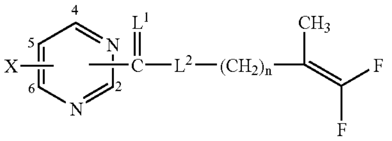

| Bonding position to hetero ring | X | $L^1$ | $L^2$ | n |
|---|---|---|---|---|
| 2 | 4,6-$(OMe)_2$ | S | O | 4 |
| 2 | 4,6-$(OMe)_2$ | O | S | 4 |
| 2 | 4,6-$(OMe)_2$ | S | S | 4 |
| 2 | 4,6-$(OEt)_2$ | O | O | 4 |
| 2 | 4-O(Bu-t)-6-OMe | O | O | 4 |
| 2 | 4-O(2-Me—Ph)-6-OH | O | O | 2 |
| 2 | 4-O(2-Me—Ph)-6-OH | O | O | 4 |
| 2 | 4-O(2-Me—Ph)-6-$O(CH_2)_4C(Me){=}CF_2$ | O | O | 4 |
| 2 | 4-O(2-Me—Ph)-6-OMe | O | O | 2 |
| 2 | 4-O(2-Me—Ph)-6-OMe | O | O | 4 |
| 2 | 4-O(2-Me—Ph)-6-$OCH_2CH{=}CH_2$ | O | O | 2 |
| 2 | 4-O(2-Me—Ph)-6-$OCH_2CH{=}CH_2$ | O | O | 4 |
| 2 | 4-O(2-Me—Ph)-6-$OCH_2C{\equiv}CH$ | O | O | 2 |
| 2 | 4-O(2-Me—Ph)-6-$OCH_2C{\equiv}CH$ | O | O | 4 |
| 2 | 4-O(2-Me—Ph)-6-$OCH_2$(Pr-c) | O | O | 2 |
| 2 | 4-O(2-Me—Ph)-6-$OCH_2$(2,2-$Cl_2$—Pr-c) | O | O | 2 |
| 2 | 4-O(2-Me—Ph)-6-$OCH_2$(2-Me—Pr-c) | O | O | 2 |
| 2 | 4-O(2-Me—Ph)-6-$OCH_2$—CN | O | O | 2 |
| 2 | 4-O(2-Me—Ph)-6-$OCH_2$—CN | O | O | 4 |
| 2 | 4-O(2-Me—Ph)-6-$OCH_2$(4-Cl—Ph) | O | O | 2 |
| 2 | 4-O(2-Me—Ph)-6-$OCH_2$(4-Cl—Ph) | O | O | 4 |
| 2 | 4-O(2-Me—Ph)-6-O(3-Picolyl) | O | O | 2 |
| 2 | 4-O(2-Me—Ph)-6-O(3-Picolyl) | O | O | 4 |
| 2 | 4-O(2-Me—Ph)-6-$OCH_2$(2-Cl-Pyrid-5-yl) | O | O | 2 |
| 2 | 4-O(2-Me—Ph)-6-$OCH_2$(2-Cl-Pyrid-5-yl) | O | O | 4 |
| 2 | 4-$OCOCH_3$-6-O(2-Me—Ph) | O | O | 2 |
| 2 | 4-$OCOCH_3$-6-O(2-Me—Ph) | O | O | 4 |
| 2 | 4-OMe-6-$NMe_2$ | O | O | 2 |
| 2 | 4-OMe-6-$NMe_2$ | O | O | 4 |
| 4 | 6-Me | O | O | 4 |
| 4 | 2-OMe | O | O | 4 |
| 4 | 2-SMe | O | O | 4 |
| 4 | 6-Ph | O | O | 4 |
| 5 | 4-Me | O | O | 4 |
| 5 | 2,4-$Me_2$ | O | O | 4 |
| 5 | 4-$CF_3$ | O | O | 4 |
| S | 4-$CF_3$ | O | O | 6 |
| 5 | 2-Cl-4-Me | O | O | 4 |
| 5 | 2-OEt-4-Me | O | O | 4 |
| 5 | 2-OPh-4-Me | O | O | 4 |
| 5 | 2-SMe-4-Me | O | O | 4 |
| 5 | 2-SOMe-4-Me | O | O | 4 |
| 5 | 2-$SO_2Me$-4-Me | O | O | 4 |
| 5 | 2-$OCH_2Ph$-4-Me | O | O | 4 |
| 5 | 2-Ph-4-Me | O | O | 2 |
| 5 | 2-Ph-4-Me | O | O | 4 |
| 5 | 2-Pr-4-Me | O | O | 2 |
| 5 | 2-Pr-4-Me | O | O | 4 |
| 5 | 2-Pr-i-4-Me | O | O | 2 |
| 5 | 2-Pr-i-4-Me | O | O | 4 |
| 5 | 2-Pr-c-4-Me | O | O | 2 |
| 5 | 2-Pr-c-4-Me | O | O | 4 |
| 5 | 2-Bu-4-Me | O | O | 2 |
| 5 | 2-Bu-4-Me | O | O | 4 |
| 5 | 2-Bu-t-4-Me | O | O | 2 |
| 5 | 2-Bu-t-4-Me | O | O | 4 |
| 5 | 2-$C_5H_{11}$-4-Me | O | O | 2 |
| 5 | 2-$C_5H_{11}$-4-Me | O | O | 4 |
| 5 | 2-$C_5H_9$-c-4-Me | O | O | 2 |
| 5 | 2-$C_5H_9$-c-4-Me | O | O | 4 |
| 5 | 2-$C_6H_{13}$-4-Me | O | O | 2 |
| 5 | 2-$C_6H_{13}$-4-Me | O | O | 4 |
| 5 | 2-$C_6H_{11}$-c-4-Me | O | O | 2 |
| 5 | 2-$C_6H_{11}$-c-4-Me | O | O | 4 |
| 5 | 2-$C_7H_{15}$-4-Me | O | O | 2 |
| 5 | 2-$C_8H_{17}$-4-Me | O | O | 2 |
| 5 | 2-$CH_2Ph$-4-Me | O | O | 2 |

TABLE 2-continued

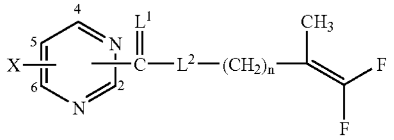

| Bonding position to hetero ring | X | $L^1$ | $L^2$ | n |
|---|---|---|---|---|
| 5 | 2-$CH_2$Ph-4-Me | O | O | 4 |
| 5 | 2-OEt-4-Me | O | O | 2 |
| 5 | 2-OPr-4-Me | O | O | 2 |
| 5 | 2-OPr-4-Me | O | O | 4 |
| 5 | 2-OBu-4-Me | O | O | 2 |
| 5 | 2-OBu-4-Me | O | O | 4 |
| 5 | 2-$OC_5H_{11}$-4-Me | O | O | 2 |
| 5 | 2-$OC_5H_{11}$-4-Me | O | O | 4 |
| 5 | 2-$OC_5H_9$-c-4-Me | O | O | 2 |
| 5 | 2-$OC_5H_9$-c-4-Me | O | O | 4 |
| 5 | 2-$OC_6H_{13}$-4-Me | O | O | 2 |
| 5 | 2-$OC_6H_{13}$-4-Me | O | O | 4 |
| 5 | 2-$OC_5H_{11}$-c-4-Me | O | O | 2 |
| 5 | 2-$OC_6H_{11}$-c-4-Me | O | O | 4 |
| 5 | 2-$OC_7H_{15}$-4-Me | O | O | 2 |
| 5 | 2-$OC_8H_{17}$-4-Me | O | O | 2 |
| 5 | 2-OPh-4-Me | O | O | 2 |
| 5 | 2-$OCH_2$Ph-4-Me | O | O | 2 |
| 5 | 2-SMe-4-Me | O | O | 2 |
| 5 | 2-SOMe-4-Me | O | O | 2 |
| 5 | 2-$SO_2$Me-4-Me | O | O | 2 |
| 5 | 2-SEt-4-Me | O | O | 2 |
| 5 | 2-SEt-4-Me | O | O | 4 |
| 5 | 2-SPr-4-Me | O | O | 2 |
| 5 | 2-SPr-4-Me | O | O | 4 |
| 5 | 2-SBu-4-Me | O | O | 2 |
| 5 | 2-SBu-4-Me | O | O | 4 |
| 5 | 2-$SC_5H_{11}$-4-Me | O | O | 2 |
| 5 | 2-$SC_5H_{11}$-4-Me | O | O | 4 |
| 5 | 2-$SC_6H_{13}$-4-Me | O | O | 2 |
| 5 | 2-$SC_6H_{13}$-4-Me | O | O | 4 |
| 5 | 2-$SC_7H_{15}$-4-Me | O | O | 2 |
| 5 | 2-$SC_8H_{17}$-4-Me | O | O | 2 |
| 5 | 2-SPh-4-Me | O | O | 2 |
| 5 | 2-SPh-4-Me | O | O | 4 |
| 5 | 2-NHPh-4-Me | O | O | 2 |
| 5 | 2-NHPh-4-Me | O | O | 4 |
| 5 | 2-N(Me)Ph-4-Me | O | O | 2 |
| 5 | 2-N(Me)Ph-4-Me | O | O | 4 |
| 5 | 2-N(Et)Ph-4-Me | O | O | 2 |
| 5 | 2-N(Et)Ph-4-Me | O | O | 4 |
| 5 | 2-N(Pr)Ph-4-Me | O | O | 2 |
| 5 | 2-N($CH_2CH{=}CH_2$)Ph-4-Me | O | O | 2 |
| 5 | 2-N($CH_2C{\equiv}CH$)Ph-4-Me | O | O | 2 |
| 5 | 2-N$(Me)_2$-4-Me | O | O | 2 |
| 5 | 2-N$(Me)_2$-4-Me | O | O | 4 |
| 5 | 2-N$(Et)_2$-4-Me | O | O | 2 |
| 5 | 2-N$(Et)_2$-4-Me | O | O | 4 |
| 5 | 2-N$(Pr)_2$-4-Me | O | O | 2 |
| 5 | 2-N$(Bu)_2$-4-Me | O | O | 2 |
| 5 | 2-(Pyrrolidin-1-yl)-4-Me | O | O | 2 |
| 5 | 2-(Pyrrolidin-1-yl)-4-Me | O | O | 4 |
| 5 | 2-(Piperidin-1-yl)-4-Me | O | O | 2 |
| 5 | 2-(Piperidin-1-yl)-4-Me | O | O | 4 |
| 5 | 2-N(Me)Et-4-Me | O | O | 2 |
| 5 | 2-N(Me)Et-4-Me | O | O | 4 |
| 5 | 2-N(Me)Pr-4-Me | O | O | 2 |
| 5 | 2-N(Me)Pr-4-Me | O | O | 4 |
| 5 | 2-N(Me)Bu-4-Me | O | O | 2 |
| 5 | 2-N(Me)Bu-4-Me | O | O | 4 |
| 5 | 2-N(Me)$C_5H_{11}$-4-Me | O | O | 2 |
| 5 | 2-N(Me)$C_6H_{13}$-4-Me | O | O | 2 |
| 5 | 2-N(Me)$C_7H_{15}$-4-Me | O | O | 2 |
| 5 | 2-N(Me)$C_8H_{17}$-4-Me | O | O | 2 |
| 5 | 2-N(Me)OH-4-Me | O | O | 2 |
| 5 | 2-N(Me)OMe-4-Me | O | O | 2 |
| 5 | 2-N(Me)OEt-4-Me | O | O | 2 |

TABLE 2-continued

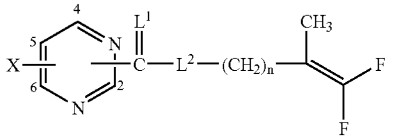

| Bonding position to hetero ring | X | $L^1$ | $L^2$ | n |
|---|---|---|---|---|
| 5 | 2-N(Me)OPr-4-Me | O | O | 2 |
| 5 | 2-N(Me)OBu-4-Me | O | O | 2 |
| 5 | 2-N(Me)$OC_5H_{11}$-4-Me | O | O | 2 |
| 5 | 2-N(Me)$OC_6H_{13}$-4-Me | O | O | 2 |
| 5 | 2-N(Me)$OC_7H_{15}$-4-Me | O | O | 2 |
| 5 | 2-N(Me)$OC_8H_{17}$-4-Me | O | O | 2 |
| 5 | 2-N(Me)$OCH_2$Ph-4-Me | O | O | 2 |
| 5 | 2-NHOMe-4-Me | O | O | 2 |
| 5 | 2-N(Et)OMe-4-Me | O | O | 2 |
| 5 | 2-N(Pr)OMe-4-Me | O | O | 2 |
| 5 | 2-N(Bu)OMe-4-Me | O | O | 2 |
| 5 | 2-N($C_5H_{11}$)OMe-4-Me | O | O | 2 |
| 5 | 2-N($C_6H_{13}$)OMe-4-Me | O | O | 2 |
| 5 | 2-N($C_7H_{15}$)OMe-4-Me | O | O | 2 |
| 5 | 2-N($C_8H_{17}$)OMe-4-Me | O | O | 2 |
| 5 | 2-N($CH_2$Ph)OMe-4-Me | O | O | 2 |
| 5 | 2-N($CH_2CH{=}CH_2$)Bu-4-Me | O | O | 2 |
| 5 | 2-N($CH_2C{\equiv}CH$)Bu-4-Me | O | O | 2 |
| 5 | 2-NH($C_6H_{11}$-c)-4-Me | O | O | 2 |
| 5 | 2-N(Me)$C_6H_{11}$-c-4-Me | O | O | 2 |
| 5 | 2-N($CH_2CH{=}CH_2$)$C_6H_{11}$-c-4-Me | O | O | 2 |
| 5 | 2-N($CH_2C{\equiv}CH$)$C_6H_{11}$-c-4-Me | O | O | 2 |
| 5 | 2-N(COMe)$C_6H_{11}$-c-4-Me | O | O | 2 |
| 5 | 2-N($CO_2$Me)$C_6H_{11}$-c-4-Me | O | O | 2 |
| 5 | 2-N($SO_2$Me)$C_6H_{11}$-c-4-Me | O | O | 2 |
| 5 | 2-N($CH_2CH{=}CH_2$)$OCH_2$Ph-4-Me | O | O | 2 |
| 5 | 2-N($CH_2C{\equiv}CH$)$OCH_2$Ph-4-Me | O | O | 2 |
| 5 | 2-N(COMe)$OCH_2$Ph-4-Me | O | O | 2 |
| 5 | 2-N($CO_2$Me)$OCH_2$Ph-4-Me | O | O | 2 |
| 5 | 2-N($SO_2$Me)$OCH_2$Ph-4-Me | O | O | 2 |
| 5 | 2-N(2-F—Ph)Me-4-Me | O | O | 2 |
| 5 | 2-N(3-F—Ph)Me-4-Me | O | O | 2 |
| 5 | 2-N(4-F—Ph)Me-4-Me | O | O | 2 |
| 5 | 2-N(2-Cl—Ph)Me-4-Me | O | O | 2 |
| 5 | 2-N(3-Cl—Ph)Me-4-Me | O | O | 2 |
| 5 | 2-N(4-Cl—Ph)Me-4-Me | O | O | 2 |
| 5 | 2-N(2-Me—Ph)Me-4-Me | O | O | 2 |
| 5 | 2-N(3-Me—Ph)Me-4-Me | O | O | 2 |
| 5 | 2-N(4-Me—Ph)Me-4-Me | O | O | 2 |
| 5 | 2-N(2-OMe—Ph)Me-4-Me | O | O | 2 |
| 5 | 2-N(3-OMe—Ph)Me-4-Me | O | O | 2 |
| 5 | 2-N(4-OMe—Ph)Me-4-Me | O | O | 2 |
| 5 | 2-N(2-$CF_3$Ph)Me-4-Me | O | O | 2 |
| 5 | 2-N(3-$CF_3$Ph)Me-4-Me | O | O | 2 |
| 5 | 2-N(4-$CF_3$Ph)Me-4-Me | O | O | 2 |
| 5 | 2-N(2,3-Cl2—Ph)Me-4-Me | O | O | 2 |
| 5 | 2-N(2,4-Cl2—Ph)Me-4-Me | O | O | 2 |
| 5 | 2-N(2,5-Cl2—Ph)Me-4-Me | O | O | 2 |
| 5 | 2-N(2,6-Cl2—Ph)Me-4-Me | O | O | 2 |
| 5 | 2-N(3,4-Cl2—Ph)Me-4-Me | O | O | 2 |
| 5 | 2-N(3,5-Cl2—Ph)Me-5-Me | O | O | 2 |
| 5 | 2-(2-F—Ph)-4-Me | O | O | 2 |
| 5 | 2-(3-F—Ph)-4-Me | O | O | 2 |
| 5 | 2-(4-F—Ph)-4-Me | O | O | 2 |
| 5 | 2-(2-Cl—Ph)-4-Me | O | O | 2 |
| 5 | 2-(3-Cl—Ph)-4-Me | O | O | 2 |
| 5 | 2-(4-Cl—Ph)-4-Me | O | O | 2 |
| 5 | 2-(2-Me—Ph)-4-Me | O | O | 2 |
| 5 | 2-(3-Me—Ph)-4-Me | O | O | 2 |
| 5 | 2-(4-Me—Ph)-4-Me | O | O | 2 |
| 5 | 2-(2-OMe—Ph)-4-Me | O | O | 2 |
| 5 | 2-(3-OMe—Ph)-4-Me | O | O | 2 |
| 5 | 2-(4-OMe—Ph)-4-Me | O | O | 2 |
| 5 | 2-(2-CF3—Ph)-4-Me | O | O | 2 |
| 5 | 2-(3-CF3—Ph)-4-Me | O | O | 2 |
| 5 | 2-(4-CF3—Ph)-4-Me | O | O | 2 |
| 5 | 2-(2,3-Cl2—Ph)-4-Me | O | O | 2 |

TABLE 2-continued

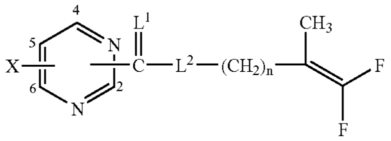

| Bonding position to hetero ring | X | $L^1$ | $L^2$ | n |
|---|---|---|---|---|
| 5 | 2-(2,4-Cl2—Ph)-4-Me | O | O | 2 |
| 5 | 2-(2,5-Cl2—Ph)-4-Me | O | O | 2 |
| 5 | 2-(2,6-Cl2—Ph)-4-Me | O | O | 2 |
| 5 | 2-(3,4-Cl2—Ph)-4-Me | O | O | 2 |
| 5 | 2-(3,5-Cl2—Ph)-4-Me | O | O | 2 |
| 5 | 2-Ph | O | O | 2 |
| 5 | 2-Ph | O | O | 4 |
| 5 | 2-Ph-4-Et | O | O | 2 |
| 5 | 2-Ph-4-Et | O | O | 4 |
| 4 | 2-Me-6-Ph | O | O | 2 |
| 4 | 2-Me-6-Ph | O | O | 4 |
| 5 | 2-N(Me)$CH_2$Ph-4-Me | O | O | 2 |
| 5 | 2-N(Me)$CH_2C{\equiv}CH$-4-Me | O | O | 2 |
| 5 | 2-N(Me)Pr-i-4-Me | O | O | 2 |
| 5 | 2-$OCH_2CH_2$OMe-4-Me | O | O | 2 |
| 5 | 2-$OCH_2$—Pr-c-4-Me | O | O | 2 |
| 5 | 2-O$(CH_2)_4$Cl-4-Me | O | O | 2 |
| 5 | 2-O-(Pyrid-3-yl)-4-Me | O | O | 2 |
| 5 | 2-(6-Me-Pyrid-2-yl)-4-Me | O | O | 2 |
| 5 | 2-N(COMe)Me-4-Me | O | O | 2 |
| 5 | 2-NHBu-4-Me | O | O | 2 |
| 5 | 2-N($COCF_3$)Bu-4-Me | O | O | 2 |
| 5 | 2-N(Me)OMe-4-Me | O | O | 4 |
| 5 | 2-N(COPh)Me-4-Me | O | O | 2 |
| 5 | 2-CN-4-Me | O | O | 4 |
| 5 | 2-Phthalimido-4-Me | O | O | 2 |
| 5 | 2-OBu-4-$CF_3$ | O | O | 2 |
| 5 | 4-$CH_2$OMe | O | O | 2 |
| 4 | 2-Ph-6-Me | O | O | 2 |
| 4 | 2-OBu-6-Me | O | O | 2 |
| 4 | 2-Me-6-OBu | O | O | 2 |
| 2 | 4-O(3-$CF_3$—Ph)6-$NMe_2$ | O | O | 2 |
| 2 | 4-Ph-6-Me | O | O | 2 |

TABLE 3

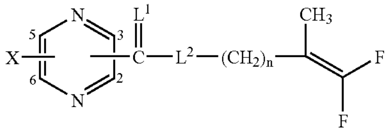

| Bonding position to hetero ring | X | $L^1$ | $L^2$ | n |
|---|---|---|---|---|
| 2 | H | O | O | 4 |
| 2 | H | O | O | 6 |
| 2 | 5-Me | O | O | 2 |
| 2 | 5-Me | O | O | 4 |
| 2 | 5-Me | O | O | 6 |
| 2 | 5-Me | O | O | 3 |
| 2 | 5-Me | S | O | 4 |
| 2 | 6-Me | O | O | 4 |
| 2 | 5-Cl | O | O | 4 |
| 2 | 6-Cl | O | O | 4 |
| 2 | 5-Ph | O | O | 2 |
| 2 | 5-Ph | O | O | 4 |
| 2 | 6-Ph | O | O | 2 |
| 2 | 6-Ph | O | O | 4 |
| 2 | 3-OMe | O | O | 4 |
| 2 | 5-OMe | O | O | 4 |
| 2 | 5-OMe | O | O | 6 |
| 2 | 6-OMe | O | O | 4 |

TABLE 3-continued

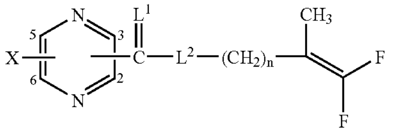

| Bonding position to hetero ring | X | $L^1$ | $L^2$ | n |
|---|---|---|---|---|
| 2 | 6-OMe | O | O | 6 |
| 2 | 6-OPr | O | O | 4 |
| 2 | 6-SEt | O | O | 4 |
| 2 | 5-COMe | O | O | 4 |

TABLE 4

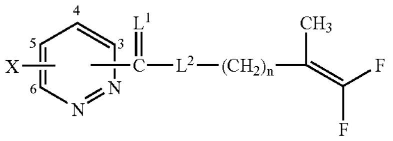

| Bonding position to hetero ring | X | $L^1$ | $L^2$ | n |
|---|---|---|---|---|
| 3 | H | O | O | 4 |
| 4 | H | O | O | 4 |
| 3 | 6-Me | O | O | 4 |
| 3 | 6-Cl | O | O | 4 |
| 4 | 3,6-$Cl_2$ | O | O | 2 |
| 4 | 3,6-$Cl_2$ | O | O | 4 |
| 4 | 3,6-$Cl_2$ | O | O | 6 |
| 3 | 6-$NH_2$ | O | O | 4 |
| 3 | 6-Ph | O | O | 4 |
| 3 | 6-OH | O | O | 4 |
| 3 | 6-OMe | O | O | 4 |
| 3 | 6-OEt | O | O | 4 |
| 3 | 6-OPh | O | O | 4 |
| 4 | 3,6-$(OMe)_2$ | O | O | 4 |

TABLE 5

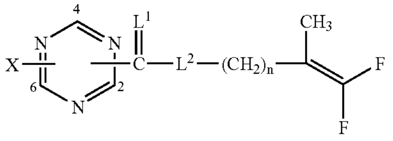

| Bonding position to hetero ring | X | $L^1$ | $L^2$ | n |
|---|---|---|---|---|
| 2 | 4,6-$(OH)_2$ | O | O | 4 |
| 2 | 4,6-$(OMe)_2$ | O | O | 2 |
| 2 | 4,6-$(OMe)_2$ | O | O | 4 |
| 2 | 4,6-$(OMe)_2$ | O | O | 6 |
| 2 | 4,6-$(OMe)_2$ | O | O | 8 |
| 2 | 4,6-$(OMe)_2$ | S | O | 4 |
| 2 | 4,6-$(OMe)_2$ | O | S | 4 |
| 2 | 4,6-$(OMe)_2$ | S | S | 4 |
| 2 | 4,6-$(OEt)_2$ | O | O | 4 |
| 2 | 4,6-$(OPr)_2$ | O | O | 4 |
| 2 | 4,6-$(OCH_2Ph)_2$ | O | O | 4 |
| 2 | 4,6-$Ph_2$ | O | O | 4 |

TABLE 6

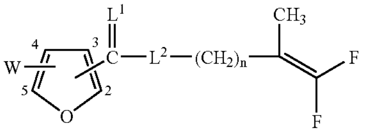

| Bonding position to hetero ring | X | $L^1$ | $L^2$ | n |
|---|---|---|---|---|
| 2 | H | O | O | 2 |
| 2 | H | O | O | 4 |
| 2 | H | O | O | 6 |
| 3 | H | O | O | 4 |
| 3 | H | O | O | 6 |
| 2 | 5-Me | O | O | 4 |
| 2 | 5-Bu-t | O | O | 4 |
| 2 | 5-Cl | O | O | 2 |
| 2 | 5-Cl | O | O | 4 |
| 2 | 5-Cl | O | O | 6 |
| 2 | 4,5-$Cl_2$ | O | O | 4 |
| 2 | 5-Br | O | O | 4 |
| 2 | 5-OMe | O | O | 4 |
| 2 | 5-$NO_2$ | O | O | 4 |
| 2 | 5-Ph | O | O | 4 |
| 2 | 5-$SO_2$Me | O | O | 4 |
| 2 | 5-NHCOMe | O | O | 4 |
| 2 | 5-(2-$NO_2$—Ph) | O | O | 4 |
| 2 | 5-(4-$NO_2$—Ph) | O | O | 2 |
| 2 | 5-(4-$NO_2$—Ph) | O | O | 4 |
| 2 | 5-(4-$NO_2$—Ph) | O | O | 6 |
| 2 | 5-(4-$NH_2$—Ph) | O | O | 4 |
| 2 | 5-(4-NHCOMe—Ph) | O | O | 4 |
| 2 | 5-(4-NHCOPh—Ph) | O | O | 4 |
| 3 | 4-Me | O | O | 4 |
| 3 | 5-$NO_2$ | O | O | 4 |
| 3 | 4-CN | O | O | 4 |

TABLE 7

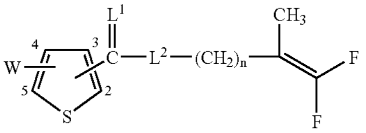

| Bonding position to hetero ring | X | $L^1$ | $L^2$ | n |
|---|---|---|---|---|
| 2 | H | O | O | 4 |
| 2 | 3-Me | O | O | 2 |
| 2 | 3-Me | O | O | 4 |
| 2 | 3-Me | O | O | 6 |
| 2 | 5-Me | O | O | 4 |
| 2 | 5-Bu-t | O | O | 4 |
| 2 | 5-Cl | O | O | 4 |
| 2 | 5-Br | O | O | 2 |
| 2 | 5-Br | O | O | 4 |
| 2 | 5-Br | O | O | 6 |
| 2 | 4,5-$Br_2$ | O | O | 4 |
| 2 | 5-Ph | O | O | 2 |
| 2 | 5-Ph | O | O | 4 |
| 2 | 5-Ph | O | O | 6 |
| 2 | 5-$NO_2$ | O | O | 4 |
| 2 | 5-OMe | O | O | 4 |
| 2 | 5-SMe | O | O | 4 |
| 2 | 5-$SO_2$Me | O | O | 4 |
| 2 | 5-COOMe | O | O | 4 |
| 2 | 5-COOEt | O | O | 4 |
| 2 | 5-(1-Me-3-$CF_3$-Pyrazol-5-yl) | O | O | 2 |

TABLE 8

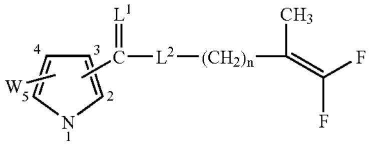

| Bonding position to hetero ring | X | L1 | L2 | n |
|---|---|---|---|---|
| 2 | H | O | O | 4 |
| 2 | H | O | O | 6 |
| 3 | H | O | O | 4 |
| 2 | 1-Me | O | O | 2 |
| 2 | 1-Me | O | O | 4 |
| 2 | 1-Me | O | O | 6 |
| 2 | 1-Me | O | O | 8 |
| 2 | 1-Me | S | O | 4 |
| 2 | 1-Me | O | S | 4 |
| 2 | 1-Me | S | S | 4 |
| 2 | 1-Et | O | O | 4 |
| 2 | 1-$CH_2CH{=}CH_2$ | O | O | 4 |
| 2 | 1-$CH_2C{\equiv}CH$ | O | O | 4 |
| 2 | 1-$CH_2$(Pr-c) | O | O | 4 |
| 2 | 1-$CH_2$OMe | O | O | 4 |
| 2 | 1-$CH_2$CN | O | O | 4 |
| 2 | 1-$CH_2$Ph | O | O | 4 |
| 2 | 1-$CH_2$(4-$NO_2$—Ph) | O | O | 4 |
| 2 | 1-$CH_2$(4-$NH_2$—Ph) | O | O | 4 |
| 2 | 1-$CH_2$(4-$NHSO_2$Me—Ph) | O | O | 4 |
| 2 | 1-$CH_2$[4-$NHSO_2$(4-Cl—Ph)—Ph] | O | O | 4 |
| 2 | 1-Me-4,5-$Cl_2$ | O | O | 2 |
| 2 | 1-Me-4,5-$Cl_2$ | O | O | 4 |
| 2 | 1-Me-4,5-$Cl_2$ | O | O | 6 |
| 2 | 4,5-$Br_2$ | O | O | 4 |
| 2 | 1,3,5-$Me_3$ | O | O | 4 |
| 2 | 1-Me-3-Cl | O | O | 4 |
| 2 | 1-Me-4-Cl | O | O | 4 |
| 2 | 1-Me-5-Cl | O | O | 4 |
| 2 | 4-$NO_2$ | O | O | 4 |
| 2 | 5-$NO_2$ | O | O | 4 |
| 2 | 1-Ph | O | O | 4 |
| 2 | 1-Me-4-$NO_2$ | O | O | 4 |
| 2 | 1-Me-5-CN | O | O | 4 |
| 2 | 1-Me-5-SMe | O | O | 4 |
| 3 | 4-Me | O | O | 4 |
| 3 | 5-Me | O | O | 4 |
| 3 | 1-Ph | O | O | 4 |
| 3 | 1-Me-2-COOMe | O | O | 4 |
| 3 | 2-Me-1,5-$Ph_2$ | O | O | 2 |
| 2 | H | O | O | 2 |
| 2 | 1-$CH_2CH{=}CH_2$ | O | O | 2 |
| 2 | 1-$CH_2$(Pr-c) | O | O | 2 |
| 2 | 1-$CH_2$CN | O | O | 2 |
| 2 | 3-$COCF_3$ | O | O | 2 |
| 2 | 4-$COCF_3$ | O | O | 2 |
| 2 | 1-$CH_2CH_2C{\equiv}CH$ | O | O | 2 |

TABLE 9

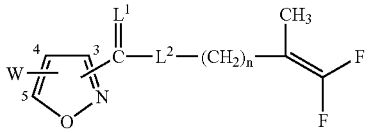

| Bonding position to hetero ring | X | L1 | L2 | n |
|---|---|---|---|---|
| 3 | H | O | O | 4 |
| 4 | H | O | O | 4 |
| 5 | H | O | O | 4 |
| 3 | 5-Me | O | O | 4 |
| 4 | 3-Me | O | O | 4 |

TABLE 9-continued

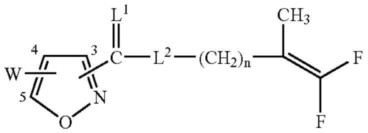

| Bonding position to hetero ring | X | L1 | L2 | n |
|---|---|---|---|---|
| 4 | 3,5-$Me_2$ | O | O | 2 |
| 4 | 3,5-$Me_2$ | O | O | 4 |
| 4 | 3,5-$Me_2$ | O | O | 6 |
| 5 | 3-Me | O | O | 4 |
| 3 | 5-COMe | O | O | 4 |
| 3 | 5-Ph | O | O | 4 |
| 3 | 5-$CH_2OMe$ | O | O | 4 |
| 3 | 5-OMe | O | O | 4 |
| 3 | 5-$NO_2$ | O | O | 4 |
| 4 | 3-Ph-5-Me | O | O | 2 |
| 4 | 3-Ph-5-Me | O | O | 4 |
| 4 | 5-$CH_2Ph$ | O | O | 4 |
| 4 | 5-Pr-c | O | O | 4 |
| 4 | 5-Pr-c | O | O | 6 |
| 5 | 3-CN | O | O | 4 |
| 5 | 3-$CONMe_2$ | O | O | 4 |
| 5 | 3-Ph | O | O | 4 |
| 5 | 4-Ph | O | O | 4 |

TABLE 10

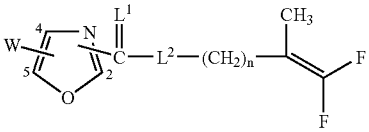

| Bonding position to hetero ring | X | L1 | L2 | n |
|---|---|---|---|---|
| 4 | H | O | O | 6 |
| 4 | 2-Me | O | O | 4 |
| 4 | 2-Et | O | O | 4 |
| 4 | 2-Pr | O | O | 4 |
| 4 | 2-Ph | O | O | 4 |
| 4 | 2-Ph-5-OEt | O | O | 4 |
| 4 | 2-$CH_2Ph$ | O | O | 2 |
| 4 | 2-$CH_2Ph$ | O | O | 4 |
| 5 | 4-Me | O | O | 4 |
| 5 | 2,4-$Me_2$ | O | O | 4 |
| 5 | 2-Ph-4-Me | O | O | 4 |

TABLE 11

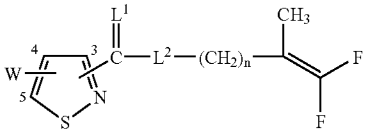

| Bonding position to hetero ring | X | $L^1$ | $L^2$ | n |
|---|---|---|---|---|
| 4 | H | O | O | 4 |
| 3 | 4-Br | O | O | 4 |
| 3 | 5-Br | O | O | 4 |
| 4 | 3-Me | O | O | 4 |
| 4 | 3-Me-5-Br | O | O | 4 |
| 4 | 3,5-$Cl_2$ | O | O | 4 |
| 4 | 3,5-$Me_2$ | O | O | 4 |
| 5 | 3-Me | O | O | 4 |

TABLE 11-continued

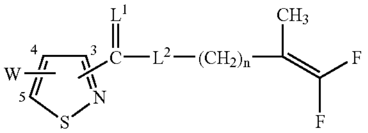

| Bonding position to hetero ring | X | $L^1$ | $L^2$ | n |
|---|---|---|---|---|
| 5 | 4-Me | O | O | 4 |
| 5 | 3,4-$Cl_2$ | O | O | 4 |
| 3 | 4-Ph | O | O | 4 |
| 3 | 5-Ph | O | O | 4 |
| 3 | 4-$NO_2$ | O | O | 4 |
| 3 | 5-$NO_2$ | O | O | 4 |
| 4 | 3-OMe | O | O | 4 |
| 4 | 3-Ph | O | O | 4 |
| 4 | 5-$CONH_2$ | O | O | 4 |
| 4 | 3-Hex-c | O | O | 4 |
| 5 | 3-Ph | O | O | 4 |
| 5 | 3-Me-4-$NO_2$ | O | O | 4 |

TABLE 12

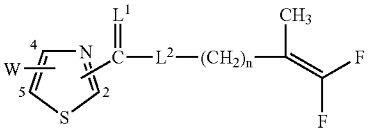

| Bonding position to hetero ring | X | $L^1$ | $L^2$ | n |
|---|---|---|---|---|
| 2 | H | O | O | 4 |
| 4 | H | O | O | 4 |
| 5 | H | O | O | 4 |
| 2 | 4-Me | O | O | 4 |
| 2 | 5-Me | O | O | 4 |
| 2 | 4-Bu-t | O | O | 4 |
| 2 | 4-Me-5-Br | O | O | 4 |
| 5 | 2-Me | O | O | 4 |
| 5 | 2-Et | O | O | 4 |
| 5 | 2-Pr-i | O | O | 4 |
| 5 | 2-Cl | O | O | 4 |
| 2 | 4-Ph | O | O | 4 |
| 2 | 5-$NO_2$ | O | O | 4 |
| 2 | 5-NHCOMe | O | O | 4 |
| 4 | 2-Ph | O | O | 4 |
| 4 | 2-(3,5-$Cl_2$—Ph) | O | O | 4 |
| 4 | 2-(4-OEt—Ph) | O | O | 4 |
| 4 | 2-(3,4-$OCH_2O$—Ph) | O | O | 4 |
| 4 | 2-(4-$NO_2$—Ph) | O | O | 4 |
| 4 | 1-(4-SMe—Ph) | O | O | 4 |
| 4 | 1-(4-SOMe—Ph) | O | O | 4 |
| 4 | 1-(4-$SO_2Me$—Ph) | O | O | 4 |
| 5 | 2-Ph-4-Me | O | O | 4 |
| 5 | 2-(4-OPr-i-Ph) | O | O | 4 |
| 5 | 2-(4-$NO_2$—Ph) | O | O | 4 |
| 5 | 2-(4-Cl—Ph)-4-Me | O | O | 4 |
| 5 | 2-(2,4-$Cl_2$—Ph)-4-Me | O | O | 4 |
| 5 | 2-(4-OEt—Ph)-4-Me | O | O | 4 |
| 5 | 2-(4-OPr-i-Ph)-4-Me | O | O | 4 |
| 5 | 2-(4-$CF_3$—Ph)-4-Me | O | O | 4 |
| 5 | 2-[3,4-$(OMe)_2$—Ph]-4-Me | O | O | 4 |
| 5 | 2-(3,4-$OCH_2O$—Ph)-4-Me | O | O | 4 |
| 5 | 1-(4-SEt—Ph)-4-Me | O | O | 4 |
| 5 | 1-(4-SOEt—Ph)-4-Me | O | O | 4 |
| 5 | 1-(4-$SO_2Et$—Ph)-4-Me | O | O | 4 |
| 5 | 2-OPh-4-Me | O | O | 4 |
| 5 | 2-O(4-Cl—Ph)-4-Me | O | O | 4 |
| 5 | 2-O(3,5-$Cl_2$—Ph)-4-Me | O | O | 4 |
| 5 | 2-[4-CON(Me)(4-OMe—Ph)—Ph]-4-Me | O | O | 4 |
| 5 | 2-(4-$NO_2$—Ph)-4-Me | O | O | 4 |

TABLE 12-continued

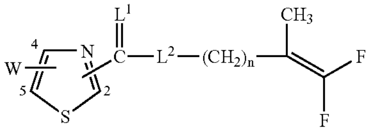

| Bonding position to hetero ring | X | $L^1$ | $L^2$ | n |
|---|---|---|---|---|
| 5 | 2-(4-$NH_2$—Ph)-4-Me | O | O | 4 |
| 5 | 2-[4-NHCO(4-Cl—Ph)—Ph]-4-Me | O | O | 4 |
| 5 | 2-[4-NHCO(4-OMe—Ph)—Ph]-4-Me | O | O | 4 |
| 5 | 2-[4-NHCO(3,4-$OCH_2O$—Ph)—Ph]-4-Me | O | O | 4 |
| 5 | 2-[4-$NHSO_2$(4-Me—Ph)—Ph]-4-Me | O | O | 4 |
| 5 | 2-[4-N(Me)$SO_2$(4-Me—Ph)—Ph]-4-Me | O | O | 4 |
| 5 | 2-(4-NHCOMe—Ph)-4-Me | O | O | 4 |
| 5 | 2-(4-NHCOEt—Ph)-4-Me | O | O | 4 |
| 5 | 2-(4-NHCOPr-i-Ph)-4-Me | O | O | 4 |
| 5 | 2-(4-NHCOBu-t-Ph)-4-Me | O | O | 4 |
| 5 | 2-(4-$NHCOCF_3$—Ph)-4-Me | O | O | 4 |
| 5 | 2-(4-$NHCOCH_2Cl$—Ph)-4-Me | O | O | 4 |
| 5 | 2-(4-$NHSO_2Me$—Ph)-4-Me | O | O | 4 |
| 5 | 2-[4-N(Et)$SO_2Me$—Ph]-4-Me | O | O | 4 |
| 5 | 2(4-$NHSO_2CH_2Cl$—Ph)-4-Me | O | O | 4 |
| 5 | 2(4-N(Pr)$SO_2CH_2Cl$—Ph)-4-Me | O | O | 4 |
| 5 | 2-Ph | O | O | 4 |
| 5 | 4-Ph | O | O | 4 |
| 5 | 2-OPh | O | O | 4 |
| 5 | 2-$NMe_2$ | O | O | 4 |
| 5 | 2-$NO_2$ | O | O | 4 |
| 5 | 2-$NH_2$-4-Me | O | O | 4 |
| 5 | 2-Phthalimido-4-Me | O | O | 4 |
| 4 | 2-$NH_2$ | O | O | 4 |
| 4 | 2-Phthalimido | O | O | 4 |
| 5 | 2-Ph-4-Me | O | O | 2 |
| 4 | 2-(Pyrid-3-yl) | O | O | 4 |
| 4 | 2-(4-$CF_3$—Ph) | O | O | 2 |
| 5 | 2-(2-Cl—Ph)-4-Me | O | O | 4 |
| 5 | 2-(3-Cl—Ph)-4-Me | O | O | 4 |
| 5 | 2-(4-$NO_2$—Ph)-4-Me | O | O | 2 |
| 5 | 2-(4-$NH_2$—Ph)-4-Me | O | O | 2 |
| 5 | 2-(4-$NMe_2$—Ph)-4-Me | O | O | 2 |
| 5 | 2-(4-NHCOMe—Ph)-4-Me | O | O | 2 |
| 5 | 2-[4-N(Me)COMe—Ph]-4-Me | O | O | 2 |
| 5 | 2-(4-$NHSO_2Me$—Ph)-4-Me | O | O | 2 |
| 5 | 2-[4-N(Me)$SO_2Me$—Ph]-4-Me | O | O | 2 |
| 5 | 2-(4-OEt—Ph)-4-Me | O | O | 2 |
| 5 | 2-(3,4-$OCH_2O$—Ph)-4-Me | O | O | 2 |
| 5 | 1-(4-SEt—Ph)-4-Me | O | O | 2 |
| 5 | 1-(4-SOEt—Ph)-4-Me | O | O | 2 |
| 5 | 1-(4-$SO_2Et$—Ph)-4-Me | O | O | 2 |
| 5 | 2-Phthalimido-4-Me | O | O | 2 |
| 5 | 2-NHCOPh-4-Me | O | O | 2 |
| 5 | 2-N(Me)COPh-4-Me | O | O | 2 |
| 5 | 2-[4-N$(COMe)_2$—Ph]-4-Me | O | O | 2 |
| 5 | 2-SPh-4-Me | O | O | 2 |
| 5 | 2-SOPh-4-Me | O | O | 2 |
| 5 | 2-$SO_2Ph$-4-Me | O | O | 2 |
| 5 | 2-(4-$CF_3$—Ph)-4-Me | O | O | 2 |
| 5 | 2-(2-OMe—Ph)-4-Me | O | O | 4 |
| 5 | 2-(3-OMe—Ph)-4-Me | O | O | 4 |
| 5 | 2-(4-OMe—Ph)-4-Me | O | O | 4 |
| 5 | 2-$CH_2Ph$-4-Me | O | O | 2 |
| 5 | 2-$CH_2Ph$-4-Me | O | O | 4 |
| 5 | 2,4-$Me_2$ | O | O | 2 |
| 5 | 2,4-$Me_2$ | O | O | 4 |
| 5 | 2-Et-4-Me | O | O | 2 |
| 5 | 2-Et-4-Me | O | O | 4 |
| 5 | 2-Pr-4-Me | O | O | 2 |
| 5 | 2-Pr-4-Me | O | O | 4 |
| 5 | 2-Pr-i-4-Me | O | O | 2 |
| 5 | 2-Pr-i-4-Me | O | O | 4 |
| 5 | 2-Pr-c-4-Me | O | O | 2 |
| 5 | 2-Pr-c-4-Me | O | O | 4 |
| 5 | 2-Bu-4-Me | O | O | 2 |
| 5 | 2-Bu-4-Me | O | O | 4 |

TABLE 12-continued

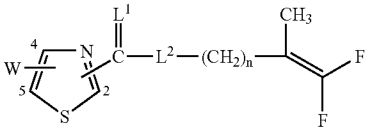

| Bonding position to hetero ring | X | $L^1$ | $L^2$ | n |
|---|---|---|---|---|
| 5 | 2-Bu-t-4-Me | O | O | 2 |
| 5 | 2-Bu-t-4-Me | O | O | 4 |
| 5 | 2-Bu-i-4-Me | O | O | 2 |
| 5 | 2-Bu-i-4-Me | O | O | 4 |
| 5 | 2-$C_5H_{11}$-4-Me | O | O | 2 |
| 5 | 2-$C_5H_{11}$-4-Me | O | O | 4 |
| 5 | 2-CH$(Et)_2$-4-Me | O | O | 2 |
| 5 | 2-CH$(Et)_2$-4-Me | O | O | 4 |
| 5 | 2-$C_5H_9$-c-4-Me | O | O | 2 |
| 5 | 2-$C_5H_9$-c-4-Me | O | O | 4 |
| 5 | 2-$C_6H_{13}$-4-Me | O | O | 2 |
| 5 | 2-$C_6H_{13}$-4-Me | O | O | 4 |
| 5 | 2-$C_6H_{11}$-c-4-Me | O | O | 2 |
| 5 | 2-$C_6H_{11}$-c-4-Me | O | O | 4 |
| 5 | 2-$C_7H_{15}$-4-Me | O | O | 2 |
| 5 | 2-$C_8H_{17}$-4-Me | O | O | 2 |
| 5 | 2-OEt-4-Me | O | O | 2 |
| 5 | 2-OEt-4-Me | O | O | 4 |
| 5 | 2-OPr-4-Me | O | O | 2 |
| 5 | 2-OPr-4-Me | O | O | 4 |
| 5 | 2-OBu-4-Me | O | O | 2 |
| 5 | 2-OBu-4-Me | O | O | 4 |
| 5 | 2-$OC_5H_{11}$-4-Me | O | O | 2 |
| 5 | 2-$OC_5H_{11}$-4-Me | O | O | 4 |
| 5 | 2-$OC_6H_{13}$-4-Me | O | O | 2 |
| 5 | 2-$OC_6H_{13}$-4-Me | O | O | 4 |
| 5 | 2-NHPh-4-Me | O | O | 2 |
| 5 | 2-NHPh-4-Me | O | O | 4 |
| 5 | 2-N(Me)Ph-4-Me | O | O | 2 |
| 5 | 2-N(Me)Ph-4-Me | O | O | 4 |
| 5 | 2-N(Et)Ph-4-Me | O | O | 2 |
| 5 | 2-N(Et)Ph-4-Me | O | O | 4 |
| 5 | 2-N(Pr)Ph-4-Me | O | O | 2 |
| 5 | 2-N($CH_2CH{=}CH_2$)Ph-4-Me | O | O | 2 |
| 5 | 2-N($CH_2C{\equiv}CH$)Ph-4-Me | O | O | 2 |
| 5 | 2-NH(2-Cl—Ph)-4-Me | O | O | 2 |
| 5 | 2-NH(2-Cl—Ph)-4-Me | O | O | 4 |
| 5 | 2-N(Me)(2-Cl—Ph)-4-Me | O | O | 2 |
| 5 | 2-N(Me)(2-Cl—Ph)-4-Me | O | O | 4 |
| 5 | 2-NH(4-Cl—Ph)-4-Me | O | O | 2 |
| 5 | 2-NH(4-Cl—Ph)-4-Me | O | O | 4 |
| 5 | 2-N(Me)(4-Cl—Ph)-4-Me | O | O | 2 |
| 5 | 2-N(Me)(4-Cl—Ph)-4-Me | O | O | 4 |
| 5 | 2-NH(4-OMe—Ph)-4-Me | O | O | 2 |
| 5 | 2-NH(4-OMe—Ph)-4-Me | O | O | 4 |
| 5 | 2-N(Me)(4-OMe—Ph)-4-Me | O | O | 2 |
| 5 | 2-N(Me)(4-OMe—Ph)-4-Me | O | O | 4 |
| 5 | 2-N(Pr-i)(4-OMe—Ph)-4-Me | O | O | 2 |
| 5 | 2-N($SO_2Me$)(4-OMe—Ph)-4-Me | O | O | 2 |
| 5 | 2-NH(4-Me—Ph)-4-Me | O | O | 2 |
| 5 | 2-NH(4-Me—Ph)-4-Me | O | O | 4 |
| 5 | 2-N(Me)(4-Me—Ph)-4-Me | O | O | 2 |
| 5 | 2-N(Me)(4-Me—Ph)-4-Me | O | O | 4 |
| 5 | 2-N(Et)(4-Me—Ph)-4-Me | O | O | 2 |
| 5 | 2-N(COOBu-t)(4-Me—Ph)-4-Me | O | O | 2 |
| 5 | 2-N($CONMe_2$)(4-Me—Ph)-4-Me | O | O | 2 |
| 5 | 2-NH(3-$CF_3$—Ph)-4-Me | O | O | 2 |
| 5 | 2-NH(3-$CF_3$—Ph)-4-Me | O | O | 4 |
| 5 | 2-N(Me)(3-$CF_3$—Ph)-4-Me | O | O | 2 |
| 5 | 2-N(Me)(3-$CF_3$—Ph)-4-Me | O | O | 4 |
| 5 | 2-Cl-4-Me | O | O | 2 |
| 5 | 2-Cl-4-Me | O | O | 4 |
| 5 | 2-Br-4-Me | O | O | 2 |
| 5 | 2-Br-4-Me | O | O | 4 |
| 5 | 2-Ph | O | O | 2 |
| 4 | 2-Ph | O | O | 2 |
| 4 | 2-NHPh | O | O | 2 |

TABLE 12-continued

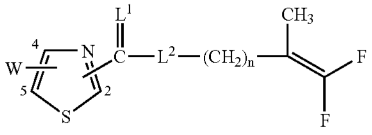

| Bonding position to hetero ring | X | $L^1$ | $L^2$ | n |
|---|---|---|---|---|
| 4 | 2-NHPh | O | O | 4 |
| 4 | 2-N(Me)Ph | O | O | 2 |
| 4 | 2-N(Me)Ph | O | O | 4 |
| 5 | 2-N($CONH_2$)(4-Me—Ph)-4-Me | O | O | 2 |
| 5 | 2-(4-N(Me)$COCF_3$—Ph)-4-Me | O | O | 4 |
| 5 | 2-(4-N(Me)$SO_2CH_2Cl$—Ph)-4-Me | O | O | 4 |
| 5 | 2-[4-NHCO(4-Cl—Ph)—Ph]-4-Me | O | O | 2 |

TABLE 13

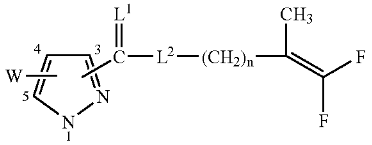

| Bonding position to hetero ring | X | L1 | L2 | n |
|---|---|---|---|---|
| 4 | 1-Me | O | O | 2 |
| 4 | 1-Me | O | O | 4 |
| 4 | 1-Me | O | O | 6 |
| 4 | 1,5-$Me_2$ | O | O | 4 |
| 4 | 1-Me-5-Cl | O | O | 4 |
| 5 | 1-Me | O | O | 2 |
| 5 | 1-Me | O | O | 4 |
| 5 | 1-Me | O | O | 6 |
| 5 | 1-Me-4-Cl | O | O | 4 |
| 5 | 1-Me-3-Et-4-Cl | O | O | 2 |
| 5 | 1-Me-3-Et-4-Cl | O | O | 4 |
| 5 | 1-Me-3-Et-4-Cl | O | O | 6 |
| 5 | 1,3-Me2-4-Cl | O | O | 4 |
| 3 | 1,5-$(CH_2)_3O$— | O | O | 4 |
| 3 | 1-Ph-5-Me | O | O | 4 |
| 3 | 1-(3,4-$OCH_2O$—Ph)-5-Me | O | O | 4 |
| 3 | 1-(4-SMe—Ph)-5-Me | O | O | 4 |
| 3 | 1-(4-SOMe—Ph)-5-Me | O | O | 4 |
| 3 | 1-(4-$SO_2Me$—Ph)-5-Me | O | O | 4 |
| 4 | 1-Ph | O | O | 4 |
| 4 | 1-$CH_2Ph$ | O | O | 4 |
| 4 | 1-Me-3-$NO_2$ | O | O | 4 |
| 4 | 1-$(CH_2)_2$O(4-Ph—Ph) | O | O | 4 |
| 4 | 1-$(CH_2)_2NHSO_2$(4-Cl—Ph) | O | O | 4 |
| 4 | 1-$(CH_2)_2$O(4-Ph—Ph) | O | O | 4 |
| 4 | 1-$(CH_2)_2$O(4-Ph—Ph) | O | O | 4 |
| 4 | 1-$CH_2$CONH(4-OMe—Ph) | O | O | 4 |
| 4 | 1-$CH_2COOCH_2Ph$ | O | O | 4 |
| 4 | 1-(4-SEt—Ph) | O | O | 4 |
| 4 | 1-(4-SOEt—Ph) | O | O | 4 |
| 4 | 1-(4-$SO_2$Et—Ph) | O | O | 4 |
| 4 | 1-(4-$NO_2$—Ph) | O | O | 4 |
| 4 | 1-(4-$NH_2$—Ph) | O | O | 4 |
| 4 | 1-(4-NHCHO—Ph) | O | O | 4 |
| 4 | 1-[4-N(Me)-CHO—Ph] | O | O | 4 |
| 4 | 1-(4-NHMe—Ph) | O | O | 4 |
| 4 | 1-(4-$NMe_2$—Ph) | O | O | 4 |
| 4 | 1-[4-NHCO(4-OMe—Ph)—Ph] | O | O | 4 |
| 4 | 1-[4-NHCO(4-OH—Ph)—Ph] | O | O | 4 |
| 4 | 1-[4-NHCO(4-$OCHF_2$—Ph)—Ph] | O | O | 4 |
| 4 | 1-[4-NHCO(4-F—Ph)—Ph] | O | O | 4 |
| 4 | 1-[4-NHCO(4-$CF_3$—Ph)—Ph] | O | O | 4 |

TABLE 13-continued

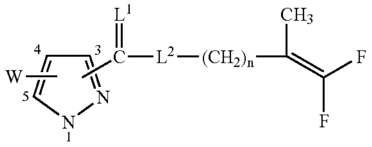

| Bonding position to hetero ring | X | L1 | L2 | n |
|---|---|---|---|---|
| 4 | 1-[4-NHCO(4-Me—Ph)—Ph] | O | O | 4 |
| 4 | 1-[4-NHCO(4-CN—Ph)—Ph] | O | O | 4 |
| 4 | 1-[4-NHCO(4-$NO_2$—Ph)—Ph] | O | O | 4 |
| 4 | 1-[4-NHCO(4-$NH_2$—Ph)—Ph] | O | O | 4 |
| 4 | 1-[4-NHCO(4-NHCOMe—Ph)—Ph] | O | O | 4 |
| 4 | 1-[4-NHCO(4-$NHCOCF_3$—Ph)—Ph] | O | O | 4 |
| 4 | 1-[4-NHCO(4-$NHSO_2$Et—Ph)—Ph] | O | O | 4 |
| 4 | 1-[4-NHCO(4-$NHSO_2CHF_2$—Ph)—Ph] | O | O | 4 |
| 5 | 1-Me-3-Ph | O | O | 4 |
| 5 | 1-Ph-4-Cl | O | O | 4 |
| 5 | 1-Me-4-$NO_2$ | O | O | 4 |
| 5 | 1-(3,4-$OCH_2O$—Ph)-3-Me | O | O | 4 |
| 5 | 1-Me-3,4-$(CH_2)_3$— | O | O | 4 |
| 3 | 1-Ph-5-Me | O | O | 2 |
| 3 | 1-Me-5-Ph | O | O | 2 |
| 3 | 1-Me-4-Cl-5-Ph | O | O | 2 |
| 4 | 1-Ph-3-Me | O | O | 2 |
| 4 | 1-Ph-3-Me | O | O | 4 |
| 4 | 1-$CH_2$Ph-3-Me | O | O | 2 |
| 4 | 1-$CH_2$Ph-3-Me | O | O | 4 |
| 4 | 1-Pr-3-Me | O | O | 2 |
| 4 | 1-Pr-3-Me | O | O | 4 |
| 4 | 1-Bu-3-Me | O | O | 2 |
| 4 | 1-Bu-3-Me | O | O | 4 |
| 4 | 1-$C_5H_{11}$-3-Me | O | O | 2 |
| 4 | 1-$C_6H_{13}$-3-Me | O | O | 2 |
| 4 | 1-Ph-5-Me | O | O | 2 |
| 4 | 1-Ph-5-Me | O | O | 4 |
| 4 | 1-$CH_2$Ph-5-Me | O | O | 2 |
| 4 | 1-$CH_2$Ph-5-Me | O | O | 4 |
| 4 | 1-Pr-5-Me | O | O | 2 |
| 4 | 1-Pr-5-Me | O | O | 4 |
| 4 | 1-Bu-5-Me | O | O | 2 |
| 4 | 1-Bu-5-Me | O | O | 4 |
| 4 | 1-$C_5H_{11}$-5-Me | O | O | 2 |
| 4 | 1-$C_6H_{13}$-5-Me | O | O | 2 |
| 5 | 1-Me-3-Ph | O | O | 2 |
| 5 | 1-Me-3-Ph-4-Cl | O | O | 2 |
| 5 | 1-Me-3-Ph-4-Cl | O | O | 4 |
| 5 | 1-Me-3-Bu-t | O | O | 2 |
| 5 | 1-Me-3-Bu-t | O | O | 4 |
| 5 | 1-Me-3-Pr | O | O | 2 |
| 5 | 1-Me-3-Pr | O | O | 4 |
| 5 | 1-Me-3-Bu | O | O | 2 |
| 5 | 1-Me-3-Bu | O | O | 4 |
| 5 | 1-Me-3-$C_5H_{11}$ | O | O | 2 |
| 5 | 1-Me-3-$C_5H_{11}$ | O | O | 4 |
| 5 | 1-Me-3-$C_6H_{13}$ | O | O | 2 |
| 5 | 1-Me-3-$C_6H_{13}$ | O | O | 4 |
| 5 | 1-Me-3-$C_7H_{15}$ | O | O | 2 |
| 5 | 1-Me-3-$C_8H_{17}$ | O | O | 2 |
| 4 | 1-$(CH_2)_2$N(Me)$SO_2$(4-Cl—Ph) | O | O | 4 |
| 4 | 1-$CH_2$CON(Me)(4-OMe—Ph) | O | O | 4 |
| 4 | 1-[4-N(Me)CO(4-OMe—Ph)—Ph] | O | O | 4 |
| 4 | 1-[4-NHCO(4-N(Me)COMe—Ph)—Ph] | O | O | 4 |
| 4 | 1-[4-NHCO(4-N(Me)$COCF_3$—Ph)—Ph] | O | O | 4 |
| 4 | 1-[4-NHCO(4-N(Me)$SO_2$Et—Ph)—Ph] | O | O | 4 |
| 4 | 1-[4-NHCO(4-N(Me)$SO_2CHF_2$—Ph)—Ph] | O | O | 4 |
| 3 | 1-$(CH_2)_2$C(Me)═$CF_2$-4-$NO_2$ | O | O | 2 |
| 5 | 1-$(CH_2)_2$C(Me)═$CF_2$-4-$NO_2$ | O | O | 2 |
| 5 | 1-Me-3,4-$(CH_2)_3$— | O | O | 2 |

TABLE 14

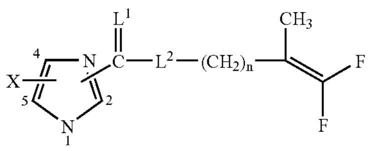

| Bonding position to hetero ring | X | L1 | L2 | n |
|---|---|---|---|---|
| 4 | H | O | O | 4 |
| 4 | H | O | O | 6 |
| 4 | 1-Me | O | O | 2 |
| 4 | 1-Me | O | O | 4 |
| 4 | 1-Me | O | O | 6 |
| 4 | 1-Pr-i | O | O | 4 |
| 4 | 1-Pr-i | O | O | 6 |
| 4 | 1-$CH_2CH{=}CH_2$ | O | O | 4 |
| 4 | 1-$CH_2C{\equiv}CH$ | O | O | 4 |
| 4 | 1-$CH_2$(Pr-c) | O | O | 2 |
| 4 | 1-$CH_2$(Pr-c) | O | O | 4 |
| 4 | 1-$CH_2$(Pr-c) | S | O | 4 |
| 4 | 1-$CH_2$(4-Cl—Ph) | O | O | 2 |
| 4 | 1-$CH_2$(4-Cl—Ph) | O | O | 4 |
| 4 | 1-$CH_2$(4-Cl—Ph) | O | O | 6 |
| 4 | 1-$CH_2$(4-OEt—Ph) | O | O | 4 |
| 4 | 1-$CH_2$(3-OPh—Ph) | O | O | 4 |
| 4 | 1-$CH_2CH_2O$(2-CF3-Pyrid-5-yl) | O | O | 4 |
| 4 | 1-$CH_2CN$ | O | O | 4 |
| 4 | 1-$CH_2OMe$ | O | O | 4 |
| 4 | 1-Me-5-Ph | O | O | 4 |
| 5 | 1,2-$(CH_2)_2S$—, 4-Me | O | O | 4 |
| 5 | 1,2-$(CH_2)_2SO_2$—, 4-Me | O | O | 4 |
| 4 | 1-$CH_2$(2,2-$Cl_2$—Pr-c) | O | O | 2 |
| 4 | 1-$CH_2$(2-Me—Pr-c) | O | O | 2 |

TABLE 15

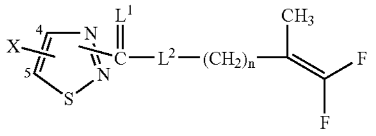

| Bonding position to hetero ring | X | $L^1$ | $L^2$ | n |
|---|---|---|---|---|
| 4 | H | O | O | 4 |
| 5 | H | O | O | 4 |
| 4 | 5-Me | O | O | 4 |
| 4 | 5-Et | O | O | 4 |
| 4 | 5-Cl | O | O | 4 |
| 4 | 5-Br | O | O | 4 |
| 4 | 5-Ph | O | O | 4 |
| 4 | 5-OEt | O | O | 4 |
| 5 | 4-Me | O | O | 2 |
| 5 | 4-Me | O | O | 4 |
| 5 | 4-Me | O | O | 6 |
| 5 | 4-Me | O | O | 8 |
| 5 | 4-Me | S | O | 4 |
| 5 | 4-Me | O | S | 4 |
| 5 | 4-Ph | O | O | 2 |
| 5 | 4-Ph | O | O | 4 |
| 5 | 4-Ph | O | O | 6 |

TABLE 16

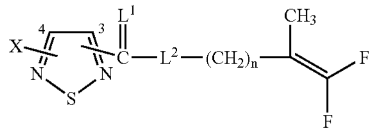

| Bonding position to hetero ring | X | $L^1$ | $L^2$ | n |
|---|---|---|---|---|
| 3 | H | O | O | 2 |
| 3 | H | O | O | 4 |
| 3 | H | O | O | 6 |
| 3 | 4-Me | O | O | 4 |
| 3 | 4-$CF_3$ | O | O | 4 |
| 3 | 4-OMe | O | O | 2 |
| 3 | 4-OMe | O | O | 4 |
| 3 | 4-OMe | O | O | 6 |
| 3 | 4-Ph | O | O | 2 |
| 3 | 4-Ph | O | O | 4 |
| 3 | 4-Ph | S | O | 4 |

TABLE 17

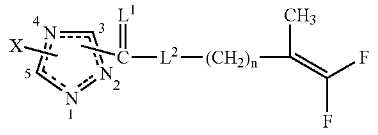

| Bonding position to hetero ring | X | $L^1$ | $L^2$ | n |
|---|---|---|---|---|
| 3 | H | O | O | 4 |
| 3 | 1-Me-5-Ph | O | O | 4 |
| 3 | 1-Me-5-$NO_2$ | O | O | 4 |
| 3 | 1-Ph | O | O | 4 |
| 3 | 1-Ph-5-Me | O | O | 2 |
| 3 | 1-Ph-5-Me | O | O | 4 |
| 3 | 1-(4-OMe—Ph)-5-Me | O | O | 2 |
| 3 | 1-(4-OMe—Ph)-5-Me | O | O | 4 |
| 3 | 1,5-$Ph_2$ | O | O | 2 |
| 3 | 1,5-$Ph_2$ | O | O | 4 |
| 3 | 4,5-$(CH_2)_3NH$— | O | O | 4 |
| 3 | 4,5-$(CH_2)_3N(Me)$— | O | O | 4 |
| 3 | 4,5-$CH(Cl)(CH_2)_2NH$— | O | O | 4 |
| 3 | 4,5-$CH(Cl)(CH_2)_2N(Me)$— | O | O | 4 |

TABLE 18

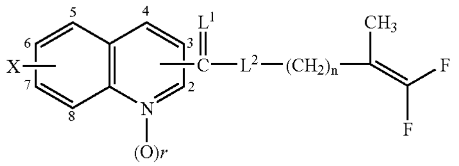

| Bonding position to hetero ring | X | r | $L^1$ | $L^2$ | n |
|---|---|---|---|---|---|
| 2 | H | 0 | O | O | 2 |
| 2 | H | 0 | O | O | 4 |
| 2 | H | 0 | O | O | 6 |
| 2 | H | 0 | O | S | 4 |
| 3 | H | 0 | O | O | 2 |
| 3 | H | 0 | O | O | 4 |
| 3 | H | 0 | O | O | 6 |
| 3 | H | 0 | O | O | 8 |
| 3 | H | 0 | O | S | 4 |
| 3 | H | 0 | S | O | 4 |
| 3 | H | 0 | S | S | 4 |

TABLE 18-continued

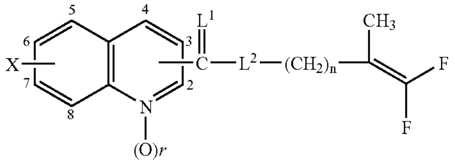

| Bonding position to hetero ring | X | r | $L^1$ | $L^2$ | n |
|---|---|---|---|---|---|
| 3 | H | 1 | O | O | 2 |
| 3 | H | 1 | O | O | 4 |
| 4 | H | 0 | O | O | 2 |
| 4 | H | 0 | O | O | 4 |
| 6 | H | 0 | O | O | 2 |
| 6 | H | 0 | O | O | 4 |
| 6 | H | 0 | O | O | 6 |
| 8 | H | 0 | O | O | 2 |
| 8 | H | 0 | O | O | 4 |
| 2 | 4-Me | 0 | O | O | 4 |
| 2 | 8-Me | 0 | O | O | 4 |
| 2 | 4-Br | 0 | O | O | 4 |
| 2 | 4-OH | 0 | O | O | 4 |
| 2 | 4-$CH_2CH{=}CH_2$ | 0 | O | O | 4 |
| 2 | 4-OPh | 0 | O | O | 4 |
| 2 | 4-CN | 0 | O | O | 4 |
| 2 | 5,8-$(OMe)_2$ | 0 | O | O | 4 |
| 3 | 7-$CF_3$ | 0 | O | O | 4 |
| 3 | 2-$NO_2$ | 0 | O | O | 4 |
| 3 | 4-OH | 0 | O | O | 4 |
| 3 | 8-Ph | 0 | O | O | 4 |
| 3 | 6-OHex-c | 0 | O | O | 4 |
| 3 | 2-Me-6,7-$(OMe)_2$ | 0 | O | O | 4 |
| 3 | 2,4,6,7-$(OMe)_4$ | 0 | O | O | 4 |
| 3 | 2-Me-6,7-$(OMe)_2$-8-$NO_2$ | 0 | O | O | 4 |
| 4 | 2-Cl | 0 | O | O | 4 |
| 6 | 2-Me | 0 | O | O | 4 |
| 6 | 3-Br | 0 | O | O | 4 |
| 6 | 2-Ph | 0 | O | O | 4 |
| 6 | 8-$NO_2$ | 0 | O | O | 4 |
| 6 | 8-OH | 0 | O | O | 4 |
| 6 | 8-Ph | 0 | O | O | 4 |

TABLE 19

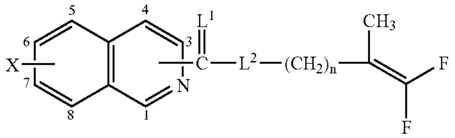

| Bonding position to hetero ring | X | $L^1$ | $L^2$ | n |
|---|---|---|---|---|
| 1 | H | O | O | 4 |
| 3 | H | O | O | 2 |
| 3 | H | O | O | 4 |
| 3 | H | O | O | 6 |
| 3 | H | O | S | 4 |
| 3 | H | O | S | 6 |
| 4 | H | O | O | 4 |
| 6 | H | O | O | 4 |
| 7 | H | O | O | 4 |
| 1 | 6,7-$(OMe)_2$ | O | O | 4 |
| 1 | 3-CN | O | O | 4 |
| 1 | 4-$NO_2$ | O | O | 4 |
| 1 | 5-$NO_2$ | O | O | 4 |
| 1 | 6-$NO_2$ | O | O | 4 |
| 3 | 1-OMe | O | O | 4 |
| 3 | 5-OMe | O | O | 4 |
| 3 | 6-OMe | O | O | 2 |
| 3 | 6-OMe | O | O | 4 |
| 3 | 7-OMe | O | O | 2 |

TABLE 19-continued

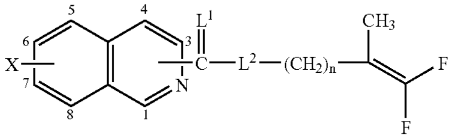

| Bonding position to hetero ring | X | $L^1$ | $L^2$ | n |
|---|---|---|---|---|
| 3 | 7-OMe | O | O | 4 |
| 3 | 8-OMe | O | O | 4 |
| 3 | 5-$NO_2$ | O | O | 4 |
| 3 | 8-$NO_2$ | O | O | 4 |
| 3 | 1-Ph | O | O | 4 |
| 4 | 1-OEt | O | O | 4 |

TABLE 20

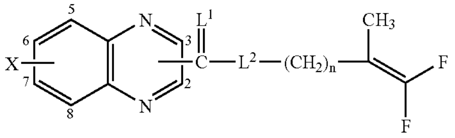

| Bonding position to hetero ring | X | $L^1$ | $L^2$ | n |
|---|---|---|---|---|
| 2 | H | O | O | 2 |
| 2 | H | O | O | 4 |
| 2 | H | O | O | 6 |
| 2 | H | O | O | 8 |
| 2 | H | S | O | 4 |
| 2 | H | O | S | 4 |
| 2 | H | S | S | 4 |
| 6 | H | O | O | 2 |
| 6 | H | O | O | 4 |
| 2 | 3-Me | O | O | 4 |
| 2 | 6-Me | O | O | 4 |
| 2 | 7-Me | O | O | 4 |
| 2 | 3-OMe | O | O | 4 |
| 2 | 6-OMe | O | O | 4 |
| 2 | 3-OPh | O | O | 4 |
| 6 | 2-Me | O | O | 4 |
| 6 | 2-Cl | O | O | 4 |
| 6 | 3-Cl | O | O | 4 |
| 6 | 2,3-$Me_2$-7-Cl | O | O | 4 |
| 6 | 3-Ph | O | O | 4 |

TABLE 21

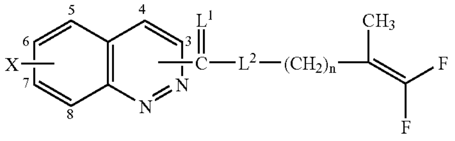

| Bonding position to hetero ring | X | $L^1$ | $L^2$ | n |
|---|---|---|---|---|
| 3 | H | O | O | 4 |
| 4 | H | O | O | 2 |
| 4 | H | O | O | 4 |
| 4 | H | O | O | 6 |
| 4 | H | S | O | 4 |
| 4 | H | O | S | 4 |
| 3 | 6-Cl | O | O | 4 |
| 3 | 6-Et | O | O | 4 |
| 3 | 4-OH-6-OMe | O | O | 4 |
| 3 | 4-OH-7-Ct | O | O | 4 |
| 4 | 8-OH | O | O | 4 |

TABLE 21-continued

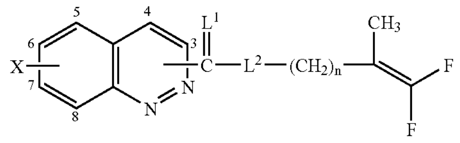

| Bonding position to hetero ring | X | $L^1$ | $L^2$ | n |
|---|---|---|---|---|
| 4 | 3-Ph | O | O | 4 |
| 7 | 4-Me | O | O | 4 |

TABLE 22

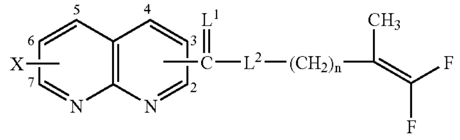

| Bonding position to hetero ring | X | $L^1$ | $L^2$ | n |
|---|---|---|---|---|
| 4 | H | O | O | 2 |
| 4 | H | O | O | 4 |
| 4 | H | O | O | 6 |
| 4 | H | S | O | 4 |
| 3 | 2-Me | O | O | 4 |
| 3 | 4-Cl-7-Me | O | O | 4 |
| 3 | 4-OMe-7-Me | O | O | 4 |
| 4 | 2,7-$Cl_2$ | O | O | 4 |
| 4 | 2,7-$(OMe)_2$ | O | O | 4 |
| 4 | 2-Ph | O | O | 4 |
| 4 | 2-$CH_2$Ph | O | O | 4 |

TABLE 23

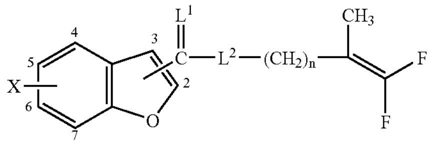

| Bonding position to hetero ring | X | $L^1$ | $L^2$ | n |
|---|---|---|---|---|
| 2 | H | O | O | 2 |
| 2 | H | O | O | 4 |
| 2 | H | O | O | 6 |
| 2 | H | O | O | 8 |
| 2 | H | S | O | 4 |
| 3 | H | O | O | 4 |
| 5 | H | O | O | 4 |
| 2 | 3-Cl | O | O | 4 |
| 2 | 5-OMe | O | O | 4 |
| 2 | 6-OMe | O | O | 4 |
| 2 | 7-OMe | O | O | 4 |
| 2 | 5-$NO_2$ | O | O | 4 |
| 2 | 7-$NO_2$ | O | O | 4 |
| 2 | 5-CN | O | O | 4 |
| 2 | 6-CN | O | O | 4 |
| 2 | 6-Ph | O | O | 4 |
| 2 | 5,6-$O(CH_2)_2O$— | O | O | 4 |
| 2 | 5,6-$O(CH_2)_2O$—, 3-Me | O | O | 4 |
| 3 | 5-OMe | O | O | 4 |
| 5 | 2-Me | O | O | 4 |
| 5 | 2-Cl | O | O | 4 |
| 5 | 4-OMe | O | O | 4 |
| 6 | 2,3-$Me_2$ | O | O | 4 |

TABLE 23-continued

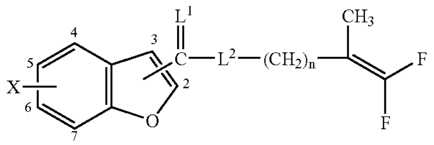

| Bonding position to hetero ring | X | $L^1$ | $L^2$ | n |
|---|---|---|---|---|
| 6 | 4-OH | O | O | 4 |
| 6 | 2-Me-4-OMe | O | O | 4 |
| 2 | 5,6-$CH(Cl)(CH_2)_2$— | O | O | 4 |
| 2 | 5,6-$CH(Cl)(CH_2)_2O$— | O | O | 4 |
| 2 | 5,6-$CH(Cl)(CH_2)_2S$— | O | O | 4 |
| 2 | 5,6-$OCH(Cl)CH_2O$— | O | O | 4 |
| 2 | 5,6-$CH(Cl)(CH_2)_2SO_2$— | O | O | 4 |

TABLE 24

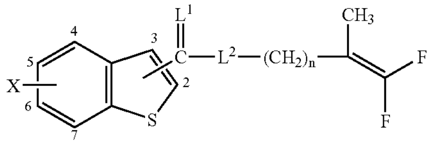

| Bonding position to hetero ring | X | $L^1$ | $L^2$ | n |
|---|---|---|---|---|
| 2 | H | O | O | 2 |
| 2 | H | O | O | 4 |
| 2 | H | O | O | 6 |
| 2 | H | O | O | 8 |
| 2 | H | S | O | 2 |
| 2 | H | S | O | 4 |
| 2 | H | O | S | 4 |
| 2 | H | S | S | 4 |
| 3 | H | O | O | 4 |
| 5 | H | O | O | 4 |
| 6 | H | O | O | 4 |
| 7 | H | O | O | 4 |
| 2 | 3-Cl | O | O | 2 |
| 2 | 3-Cl | O | O | 4 |
| 2 | 4-Cl | O | O | 4 |
| 2 | 5-Cl | O | O | 4 |
| 2 | 6-Cl | O | O | 4 |
| 2 | 4-Me | O | O | 4 |
| 2 | 5-Me | O | O | 4 |
| 2 | 5-OH | O | O | 4 |
| 2 | 5-$OCH_2CF_3$ | O | O | 4 |
| 2 | 5-$O(CH_2)_2OMe$ | O | O | 4 |
| 2 | 5-$OCH_2CH$═CHCl | O | O | 4 |
| 2 | 5-$O(CH_2)_2O(5$-$CF_3$-Pyrid-2-yl) | O | O | 4 |
| 2 | 5-$O(CH_2)_2OCH_2$(4-CN—Ph) | O | O | 4 |
| 2 | 5-$O(CH_2)_2$OCO(4-OH—Ph) | O | O | 4 |
| 2 | 5-$O(CH_2)_2$OCO(2-CON$(Me)_2$—Ph) | O | O | 4 |
| 2 | 5-$O(CH_2)_2$NHCO(4-$OCHF_2$—Ph) | O | O | 4 |
| 2 | 6-OMe | O | O | 4 |
| 2 | 7-OMe | O | O | 4 |
| 2 | 4-$NO_2$ | O | O | 4 |
| 2 | 5-$NO_2$ | O | O | 4 |
| 2 | 5-$NH_2$ | O | O | 4 |
| 2 | 5-NHMe | O | O | 4 |
| 2 | 5-NHCO(3-OPh—Ph) | O | O | 4 |
| 2 | 5-N(Me)CO(3-OPh—Ph) | O | O | 4 |
| 2 | 5-$NHCOCH_2Cl$ | O | O | 4 |
| 2 | 5-$NHCOCF_3$ | O | O | 4 |
| 2 | 5-$NHSO_2Me$ | O | O | 4 |
| 2 | 5-N(Me)$SO_2$Me | O | O | 4 |
| 2 | 5-$NHSO_2CH_2Cl$ | O | O | 4 |
| 2 | 5-$NHSO_2$(4-Me—Ph) | O | O | 4 |
| 2 | 5-NHCO(3,4-$OCH_2O$—Ph) | O | O | 4 |
| 2 | 5-N(Me)CO(3,4-$OCH_2O$—Ph) | O | O | 4 |

TABLE 24-continued

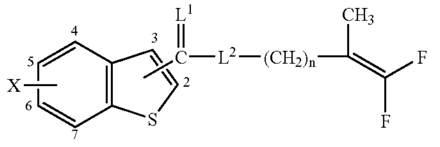

| Bonding position to hetero ring | X | $L^1$ | $L^2$ | n |
|---|---|---|---|---|
| 2 | 6-$NO_2$ | O | O | 4 |
| 2 | 7-$NO_2$ | O | O | 4 |
| 2 | 5-CN | O | O | 4 |
| 3 | 5-Me | O | O | 4 |
| 3 | 5-OMe | O | O | 4 |
| 3 | 2-Hex-c | O | O | 4 |
| 5 | 3-Me | O | O | 4 |
| 5 | 4-OMe | O | O | 4 |
| 6 | 3-Me | O | O | 4 |
| 6 | 2-Me-4-OMe | O | O | 4 |
| 3 | H | O | O | 2 |
| 2 | 5-N(Me)$COCF_3$ | O | O | 4 |
| 2 | 5-N(Me)$SO_2CH_2Cl$ | O | O | 4 |
| 2 | 5-O$(CH_2)_2$N(Me)CO(4-$OCHF_2$—Ph) | O | O | 4 |
| 2 | 5-O$(CH_2)_2$OCO(2-$CONH_2$—Ph) | O | O | 4 |
| 2 | 3-Ph | O | O | 2 |
| 2 | 5-$NMe_2$ | O | O | 4 |

TABLE 25

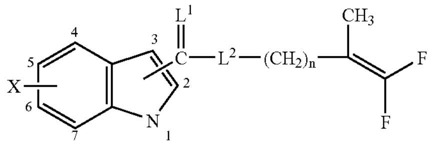

| Bonding position to hetero ring | X | $L^1$ | $L^2$ | n |
|---|---|---|---|---|
| 2 | H | O | O | 2 |
| 2 | H | O | O | 4 |
| 3 | H | O | O | 2 |
| 3 | H | O | O | 4 |
| 5 | H | O | O | 2 |
| 5 | H | O | O | 4 |
| 7 | H | O | O | 2 |
| 7 | H | O | O | 4 |
| 2 | 1-Me | O | O | 2 |
| 2 | 1-Me | O | O | 4 |
| 2 | 1-Me | O | O | 6 |
| 2 | 1-Me | S | O | 4 |
| 2 | 1-Et | O | O | 2 |
| 2 | 1-Et | O | O | 4 |
| 2 | 3-Ph | O | O | 4 |
| 2 | 1-Me-3-Ph | O | O | 4 |
| 2 | 5-OMe | O | O | 4 |
| 2 | 1-Me-5-OMe | O | O | 4 |
| 2 | 1-Me-5-$NO_2$ | O | O | 4 |
| 2 | 5,6-O$(CH_2)_2$O— | O | O | 4 |
| 2 | 5,6-O$(CH_2)_2$O—, 3-Cl | O | O | 4 |
| 2 | 5,6-O$(CH_2)_2$O—, 4-Cl | O | O | 4 |
| 2 | 5,6-O$(CH_2)_2$O—, 7-Cl | O | O | 4 |
| 3 | 1-Me | O | O | 4 |
| 3 | 1-Pr-i | O | O | 4 |
| 3 | 6-Ph | O | O | 4 |
| 3 | 5-OMe | O | O | 4 |
| 3 | 6-OMe | O | O | 4 |
| 3 | 1-$CH_2$Ph | O | O | 4 |
| 5 | 1-Me | O | O | 4 |
| 5 | 1-Me | S | O | 4 |
| 5 | 1-$CHF_2$ | O | O | 4 |
| 5 | 1-$CH_2CH_2F$ | O | O | 4 |
| 5 | 1-$CH_2$(4-OPr-i-Ph) | O | O | 4 |

TABLE 25-continued

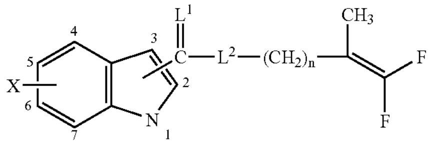

| Bonding position to hetero ring | X | $L^1$ | $L^2$ | n |
|---|---|---|---|---|
| 5 | 7-OMe | O | O | 4 |
| 5 | 1-$CH_2$OMe | O | O | 4 |
| 5 | 1-$CH_2$(Pr-c) | O | O | 4 |
| 5 | 1-$CH_2$(2-Cl-Pyrid-5-yl) | O | O | 4 |
| 5 | 1-$CH_2$(4-Cl—Ph) | O | O | 4 |
| 6 | 1-Me | O | O | 4 |
| 6 | 4-OMe | O | O | 4 |
| 7 | 1-Me | O | O | 4 |

TABLE 26

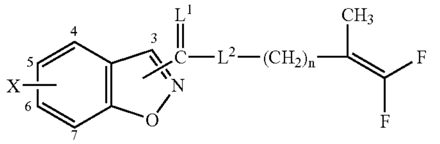

| Bonding position to hetero ring | X | $L^1$ | $L^2$ | n |
|---|---|---|---|---|
| 3 | H | O | O | 2 |
| 3 | H | O | O | 4 |
| 3 | H | O | O | 6 |
| 3 | H | S | O | 4 |
| 3 | 6-Cl | O | O | 4 |
| 3 | 6-$NO_2$ | O | O | 2 |
| 3 | 6-$NO_2$ | O | O | 4 |
| 3 | 6-$NH_2$ | O | O | 4 |
| 3 | 6-NHCOMe | O | O | 4 |
| 3 | 6-OMe | O | O | 2 |
| 3 | 6-OMe | O | O | 4 |

TABLE 27

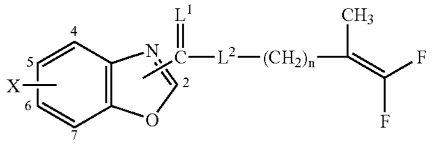

| Bonding position to hetero ring | X | $L^1$ | $L^2$ | n |
|---|---|---|---|---|
| 5 | H | O | O | 2 |
| 5 | H | O | O | 4 |
| 5 | H | O | O | 6 |
| 5 | H | O | O | 8 |
| 5 | H | S | O | 4 |
| 5 | 2-Me | O | O | 2 |
| 5 | 2-Me | O | O | 4 |
| 5 | 2-Me | O | O | 6 |
| 5 | 2-Ph | O | O | 2 |
| 5 | 2-Ph | O | O | 4 |
| 5 | 2-Ph | O | O | 6 |

TABLE 28

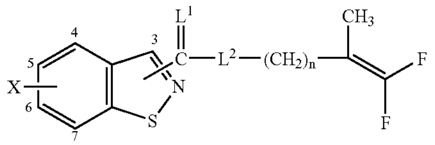

| Bonding position to hetero ring | X | $L^1$ | $L^2$ | n |
|---|---|---|---|---|
| 3 | H | O | O | 2 |
| 3 | H | O | O | 4 |
| 3 | H | O | O | 6 |
| 3 | H | S | O | 4 |
| 3 | 5-$NO_2$ | O | O | 2 |
| 3 | 5-$NO_2$ | O | O | 4 |
| 5 | 3-Me | O | O | 2 |
| 5 | 3-Me | O | O | 4 |

TABLE 29

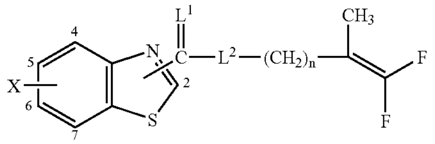

| Bonding position to hetero ring | X | $L^1$ | $L^2$ | n |
|---|---|---|---|---|
| 2 | H | O | O | 2 |
| 2 | H | O | O | 4 |
| 2 | H | O | O | 6 |
| 2 | H | S | O | 4 |
| 5 | H | O | O | 2 |
| 5 | H | O | O | 4 |
| 6 | H | O | O | 2 |
| 6 | H | O | O | 4 |
| 2 | 5,6-$Me_2$ | O | O | 4 |
| 5 | 2-Me | O | O | 2 |
| 5 | 2-Me | O | O | 4 |
| 6 | 2-Me | O | O | 2 |
| 6 | 2-Me | O | O | 4 |
| 2 | 4-OMe | O | O | 4 |
| 2 | 6-OMe | O | O | 4 |
| 2 | 6-$NO_2$ | O | O | 4 |
| 5 | 2-$NH_2$ | O | O | 4 |
| 5 | 2-Ph | O | O | 4 |
| 6 | 2-Ph | O | O | 4 |

TABLE 30

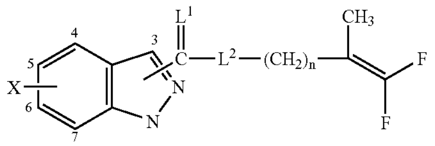

| Bonding position to hetero ring | X | $L^1$ | $L^2$ | n |
|---|---|---|---|---|
| 3 | 1-H | O | O | 2 |
| 3 | 1-H | O | O | 4 |
| 5 | 1-H | O | O | 2 |
| 5 | 1-H | O | O | 4 |
| 6 | 1-H | O | O | 2 |
| 6 | 1-H | O | O | 4 |
| 3 | 1-Me | O | O | 2 |
| 3 | 1-Me | O | O | 4 |

TABLE 30-continued

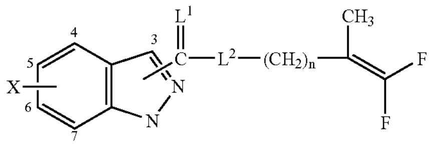

| Bonding position to hetero ring | X | $L^1$ | $L^2$ | n |
|---|---|---|---|---|
| 3 | 1-Me | O | O | 6 |
| 3 | 1-Et | O | O | 2 |
| 3 | 1-Et | O | O | 4 |
| 3 | 1-Ph | O | O | 4 |
| 3 | 1-(4-OMe—Ph) | O | O | 4 |
| 3 | 1-(4-Me—Ph) | O | O | 4 |
| 3 | 1-Ph-6-$NO_2$ | O | O | 4 |
| 3 | 1-(4-OMe—Ph)-6-$NO_2$ | O | O | 4 |
| 3 | 1-(4-Me—Ph)-6-$NO_2$ | O | O | 4 |
| 3 | 1-COMe | O | O | 4 |
| 3 | 1-COMe-6-$NO_2$ | O | O | 4 |
| 3 | 1-COPh | O | O | 4 |
| 3 | 1-CO(4-Cl—Ph) | O | O | 4 |
| 3 | 1-COPh-6-$NO_2$ | O | O | 4 |
| 3 | 1-CO(4-Cl—Ph)-6-$NO_2$ | O | O | 4 |
| 5 | 1-COMe | O | O | 4 |
| 6 | 1-COMe | O | O | 4 |

TABLE 31

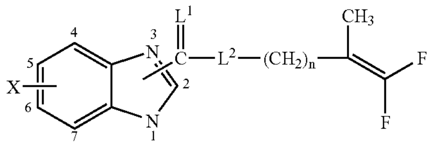

| Bonding position to hetero ring | X | $L^1$ | $L^2$ | n |
|---|---|---|---|---|
| 5 | 1-H | O | O | 2 |
| 5 | 1-H | O | O | 4 |
| 5 | 1-H | O | O | 6 |
| 5 | 1-Me | O | O | 2 |
| 5 | 1-Me | O | O | 4 |
| 5 | 1-Me | O | O | 6 |
| 5 | 1-Me | S | O | 4 |
| 6 | 1-Me | O | O | 2 |
| 6 | 1-Me | O | O | 4 |
| 5 | 1-$CH_2Ph$ | O | O | 2 |
| 5 | 1-$CH_2Ph$ | O | O | 4 |
| 6 | 1-$CH_2Ph$ | O | O | 2 |
| 6 | 1-$CH_2Ph$ | O | O | 4 |
| 5 | 1-$(CH_2)_2C(Me){=}CF_2$ | O | O | 2 |
| 5 | 1-$(CH_2)_4C(Me){=}CF_2$ | O | O | 4 |
| 6 | 1-$(CH_2)_2C(Me){=}CF_2$ | O | O | 2 |
| 6 | 1-$(CH_2)_4C(Me){=}CF_2$ | O | O | 4 |

TABLE 32

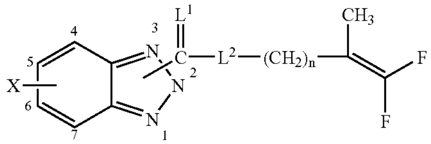

| Bonding position to hetero ring | X | $L^1$ | $L^2$ | n |
|---|---|---|---|---|
| 5 | 2-H | O | O | 2 |
| 5 | 2-H | O | O | 4 |

TABLE 32-continued

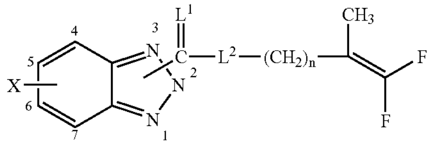

| Bonding position to hetero ring | X | $L^1$ | $L^2$ | n |
|---|---|---|---|---|
| 5 | 2-H | O | O | 6 |
| 5 | 2-Me | O | O | 2 |
| 5 | 2-Me | O | O | 4 |
| 5 | 2-Me | O | O | 6 |
| 5 | 2-Me | S | O | 4 |
| 5 | $2\text{-}CH_2Ph$ | O | O | 2 |
| 5 | $2\text{-}CH_2Ph$ | O | O | 4 |
| 5 | $2\text{-}(CH_2)_2C(Me){=}CF_2$ | O | O | 2 |
| 5 | $2\text{-}(CH_2)_4C(Me){=}CF_2$ | O | O | 4 |

TABLE 33

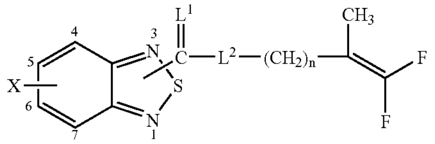

| Bonding position to hetero ring | X | $L^1$ | $L^2$ | n |
|---|---|---|---|---|
| 5 | H | O | O | 2 |
| 5 | H | O | O | 4 |
| 5 | H | O | O | 6 |
| 5 | H | O | O | 8 |
| 5 | H | S | O | 2 |
| 5 | H | S | O | 4 |
| 5 | H | S | O | 6 |

TABLE 34

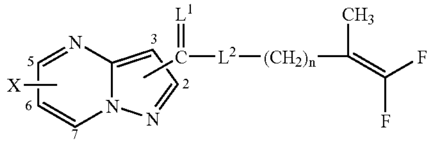

| Bonding position to hetero ring | X | $L^1$ | $L^2$ | n |
|---|---|---|---|---|
| 3 | $5,7\text{-}Me_2$ | O | O | 2 |
| 3 | $5,7\text{-}Me_2$ | O | O | 4 |
| 3 | $5,7\text{-}Pr_2$ | O | O | 4 |
| 3 | $5,7\text{-}(OMe)_2$ | O | O | 2 |
| 3 | $5,7\text{-}(OMe)_2$ | O | O | 4 |
| 3 | 5-Me-7-OH | O | O | 4 |
| 5 | 2-Ph-7-Me | O | O | 2 |
| 5 | 2-Ph-7-Me | O | O | 4 |
| 5 | 2-Ph-7-Pr-i | O | O | 4 |
| 5 | 2-Ph-7-Bu-t | O | O | 4 |
| 5 | $2,7\text{-}Ph_2$ | O | O | 4 |
| 6 | 2-Ph-7-Me | O | O | 4 |
| 6 | 2-(4-Cl—Ph)-7-Me | O | O | 4 |

TABLE 35

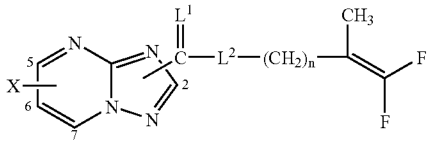

| Bonding position to hetero ring | X | $L^1$ | $L^2$ | n |
|---|---|---|---|---|
| 2 | $5,7\text{-}Me_2$ | O | O | 2 |
| 2 | $5,7\text{-}Me_2$ | O | O | 4 |
| 2 | $5,7\text{-}Me_2$ | O | O | 6 |
| 2 | $5,7\text{-}Pr_2$ | O | O | 4 |
| 2 | 5-Me-7-OH | O | O | 4 |
| 2 | 5-Me-7-OMe | O | O | 4 |
| 5 | 7-Me | O | O | 4 |
| 6 | 7-Me | O | O | 4 |
| 6 | 7-OH | O | O | 4 |
| 7 | 5-Me | O | O | 4 |

TABLE 36

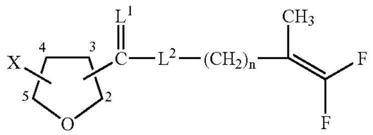

| Bonding position to hetero ring | X | $L^1$ | $L^2$ | n |
|---|---|---|---|---|
| 2 | H | O | O | 2 |
| 2 | H | O | O | 4 |
| 2 | H | O | O | 6 |
| 2 | H | O | O | 8 |
| 2 | H | S | O | 4 |
| 3 | H | O | O | 2 |
| 3 | H | O | O | 4 |
| 3 | H | O | O | 6 |
| 3 | H | O | O | 8 |
| 3 | H | S | O | 4 |

TABLE 37

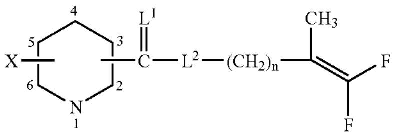

| Bonding position to hetero ring | X | $L^1$ | $L^2$ | n |
|---|---|---|---|---|
| 3 | 1-COMe | O | O | 2 |
| 3 | 1-COMe | O | O | 4 |
| 3 | $1\text{-}COCF_3$ | O | O | 4 |
| 3 | $1\text{-}COCCl_3$ | O | O | 4 |
| 3 | 1-COO—Bu-t | O | O | 2 |
| 3 | 1-COO—Bu-t | O | O | 4 |
| 3 | 1-COPh | O | O | 2 |
| 3 | 1-COPh | O | O | 4 |
| 3 | 1-CO(4-Cl—Ph) | O | O | 2 |
| 3 | 1-CO(4-Cl—Ph) | O | O | 4 |
| 3 | 1-CO(4-Cl—Ph) | S | O | 4 |
| 3 | $1\text{-}CH_2Ph$ | O | O | 2 |
| 3 | $1\text{-}CH_2Ph$ | O | O | 4 |
| 3 | $1\text{-}CH_2(4\text{-}Cl\text{—}Ph)$ | O | O | 2 |
| 3 | $1\text{-}CH_2(4\text{-}Cl\text{—}Ph)$ | O | O | 4 |
| 4 | 1-COMe | O | O | 2 |

TABLE 37-continued

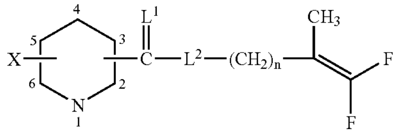

| Bonding position to hetero ring | X | $L^1$ | $L^2$ | n |
|---|---|---|---|---|
| 4 | 1-COMe | O | O | 4 |
| 4 | $1\text{-}COCF_3$ | O | O | 4 |
| 4 | $1\text{-}COCCl_3$ | O | O | 4 |
| 4 | 1-COO—Bu-t | O | O | 2 |
| 4 | 1-COO—Bu-t | O | O | 4 |
| 4 | 1-COPh | O | O | 2 |
| 4 | 1-COPh | O | O | 4 |
| 4 | 1-CO(4-Cl—Ph) | O | O | 2 |
| 4 | 1-CO(4-Cl—Ph) | O | O | 4 |
| 4 | 1-CO(4-Cl—Ph) | S | O | 4 |
| 4 | $1\text{-}CH_2Ph$ | O | O | 2 |
| 4 | $1\text{-}CH_2Ph$ | O | O | 4 |
| 4 | $1\text{-}CH_2$(4-Cl—Ph) | O | O | 2 |
| 4 | $1\text{-}CH_2$(4-Cl—Ph) | O | O | 4 |

A compound of the present invention having the general formula [1] can be produced in accordance with the production methods shown below, but it should not be limited to these methods.

<Production Method 1>

A compound [1a] of the present invention can be synthesized by reacting a compound [5] with a compound [2] in a solvent in the presence of a base as follows.

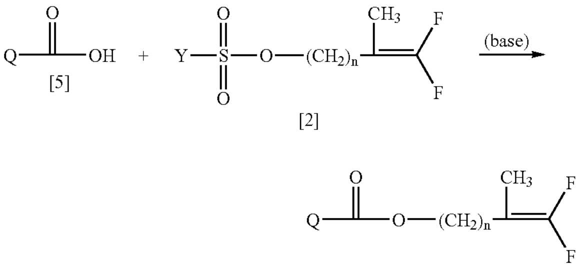

[5] [2] [1a]

(wherein Q, n and Y represent the same meaning described above.) Molar ratio of the raw materials can be set arbitrary, but, in general, the ratio of the compound [2] is 0.5 to 2 equivalents to 1 equivalent of the compound [5]. Reaction temperature in any of the reactions can be set arbitrary from 0° C. to refluxing temperature of a reaction system, and preferably in the range from room temperature to 120° C., and reaction is completed within 0.5 hour to 5 hours, although it depends on compounds.

A solvent includes, for example, ethers such as dioxane and tetrahydrofuran (THF); halogenated hydro carbons such as dichloroethane, carbon tetrachloride, chlorobenzene and di chlorobenzene; amides such as N,N-dimethylacetamide, N,N-dimethylformamide (DMF) and N-methyl-2-pyrrolidinone; sulfur compounds such as dimethylsulfoxide (DMSO) and sulfolane; aromatic hydrocarbons such as benzene, toluene and xylene; ketones such as acetone and 2-butanone; nitriles such as acetonitrile; water or a mixture thereof.

A base includes, for example, a metal hydride such as sodium hydride; organic bases such as pyridine, triethylamine, dimethylaminopyridine or 1,8-diazabicyclo-[5.4.0]-7-undecene; inorganic salts including hydroxides of alkali metals such as sodium hydroxide and potassium hydroxide; hydroxides of alkali earth metals such as calcium hydroxide and magnesium hydroxide; carbonate salts of alkali metals such as sodium carbonate and potassium carbonate; bicarbonates of alkali metals such as sodium hydrogen carbonate and potassium hydrogen carbonate; and metal salts of alcohols such as sodium methoxide and potassium tert-butoxide.

A raw material compound [5] is either obtained as a commercial product or by hydrolysis of a commercial ester product or nitrile product, or can be synthesized by a method described in known literature or a method in accordance with said method. Known literature includes, for example:

"Methoden Der Organischen Chemie", vol. E7b, page 296 to 662 (1992) for the case Q is a pyridyl group;

"Methods Of Organic Chemistry", vol. E9b1, page 8 to 249 (1998) for the case Q is a pyrimidinyl group;

"Methods Of Organic Chemistry", vol. E9b1, page 260 to 346 (1998) for the case Q is a pyrazinyl group;

"Methods Of Organic Chemistry", vol. E9a, page 568 to 666 (1997) for the case Q is a pyridazinyl group;

"Methods Of Organic Chemistry", vol. E9c, page 674 to 782 (1997) for the case Q is a triazinyl group;

"Methoden Der Organischen Chemie", vol. E6a, page 26 to 154 (1994) for the case Q is a furyl group;

"Methoden Der Organischen Chemie", vol. E6a, page 194 to 488 (1994) for the case Q is a thienyl group;

"Methoden Der Organischen Chemie", vol. E6a, page 570 to 769 (1994) for the case Q is a pyrrolyl group;

"Methoden Der Organischen Chemie", vol. E8a, page 49 to 176 (1993) for the case Q is an isoxazolyl group;

"Methoden Der Organischen Chemie", vol. E8a, page 894 to 1001 (1993) for the case Q is an oxazolyl group;

"Methoden Der Organischen Chemie", vol. E8a, page 674 to 771 (1993) for the case Q is an isothiazolyl group;

"Methoden Der Organischen Chemie", vol. E8b, page 5 to 325 (1994) for the case Q is a thiazolyl group;

"Methoden Der Organischen Chemie", vol. E8b, page 408 to 704 (1994) for the case Q is a pyrazolyl group;

"Methoden Der Organischen Chemie", vol. E8c, page 4 to 185 (1994) for the case Q is an imidazolyl group;

"Methoden Der Organischen Chemie", vol. E8d, page 60 to 84 or page 153 to 167 (1994) for the case Q is a thiadiazolyl group;

"Methoden Der Organischen Chemie", vol. E8d, page 481 to 583 (1994) for the case Q is a triazolyl group;

"Methoden Der Organischen Chemie", vol. E7a, page 307 to 469 (1991) for the case Q is a quinolyl group;

"Methoden Der Organischen Chemie", vol. E7a, page 583 to 726 (1991) for the case Q is an isoquinolyl group;

"Methods Of Organic Chemistry", vol. E9b2, page 196 to 249 (1997) for the case Q is a quinoxalinyl group;

"Methods Of Organic Chemistry", vol. E9a, page 691 to 738 (1997) for the case Q is a cinnolinyl group;

"J. Org. Chem.", page 2838 (1990) or "J. Med. Chem.", page 2674 (1997) for the case Q is a naphthyrlidinyl group;

"Methoden Der Organischen Chemie", vol. E6b1, page 40 to 141 (1994) for a benzofuryl group;

"Methoden Der Organischen Chemie", vol. E6b1, page 220 to 263 (1994) for the case Q is a benzothienyl group;

"Methoden Der Organischen Chemie", vol. E6b1, page 562 to 848 or vol. E6b2, page 849 to 1216 (1994) for the case Q is an indolyl group;

"Methoden Der Organischen Chemie", vol. E8a, page 232 to 321 (1993) for the case Q is a benzoisoxazolyl group;

"Methoden Der Organischen Chemie", vol. E8a, page 1022 to 1164 (1993) for the case Q is a benzoxazolyl group;

"Methoden Der Organischen Chemie", vol. E8a, page 801 to 840 (1993) for the case Q is a benzoisothiazolyl group;

"Methoden Der Organischen Chemie", vol. E8b, page 869 to 1009 (1994) for the case Q is a benzothiazolyl group;

"Methoden Der Organischen Chemie", vol. E8b, page 770 to 851 (1994) for the case Q is an indazolyl group;

"Methoden Der Organischen Chemie", vol. E8c, page 222 to 372 (1994) for the case Q is a benzoimidazolyl group;

"Methoden Der Organischen Chemie", vol. E8d, page 409 to 467 (1994) for the case Q is a bezotriazolyl group;

"Methoden Der Organischen Chemie", vol. E8d, page 171 to 184 (1994) for the case Q is a benzothiadiazolyl group; and "J. Heterocycl. Chem.", page 735 (1983) for the case Q is a pyrazolopyrimidinyl group and a triazolopyrimidinyl group.

A compound [2a] wherein n is 4 to 8, in a raw material compound [2], can be synthesized by the following method:

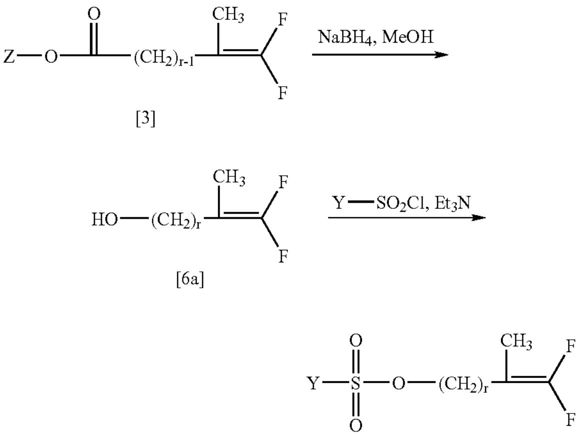

[3]

[6a]

[2a]

(wherein Z and Y represent the same meaning as described above, and r represents 4 to 8.)

A compound [3] can be synthesized by the following method:

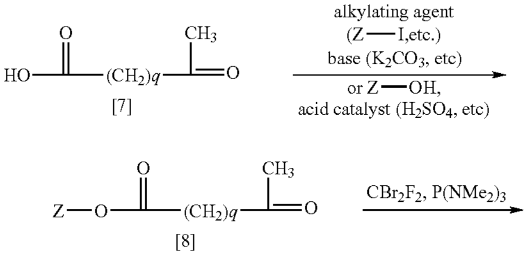

[7]

[8]

-continued

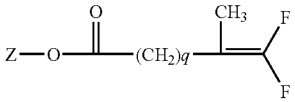

[3]

(wherein Z and q represent the same meaning as described above.) A compound [7] having q representing 3 to 5, can be available as a commercial product, while one whose q represents 6 can be produced in accordance with a method described in, for example, "J. Org. Chem.", page 3456 (1975), and one whose q represents 7 can be produced in accordance with a method described in, for example, "J. Med. Chem.", page 1152 (1977).

A compound [2b] wherein n represents 2 or 3, in a raw material compound [2], can be synthesized by the following method:

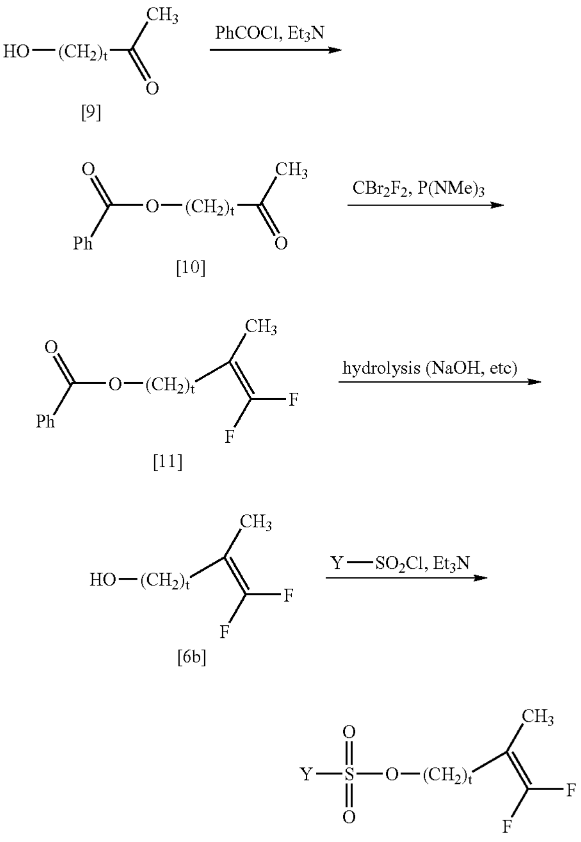

[9]

[10]

[11]

[6b]

[2b]

(wherein Y represents the same meaning as described above and t represents 2 or 3.) A compound [9] can be available as a commercial product.

<Production Method 2>

A compound [1b-1] or [1b-2] of the present invention can be synthesized by reacting a compound [12] with a compound [6] or a compound [13] in a solvent in the presence of a base.

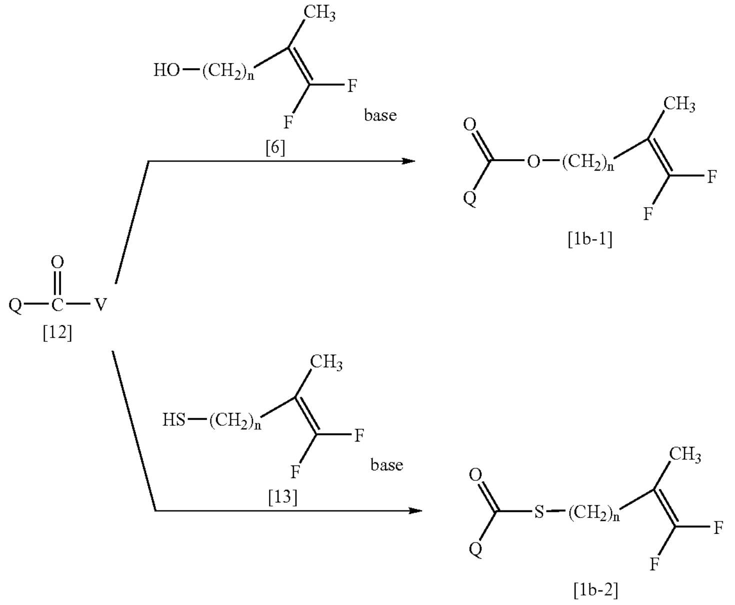

[6] [12] [13] [1b-1] [1b-2]

(wherein Q and n represent the same meaning described above and V represents a halogen atom.)

Molar ratio of raw materials can be set arbitrarily, but, in general, the ratio of a compound [6] or a compound [13] is 0.5 to 2 equivalents to 1 equivalent of a compound [12].

Reaction temperature in any reaction can be set arbitrarily from −20° C. to refluxing temperature of a reaction system, and preferably in the range of 0° C. to 60° C., and reaction is completed within 0.2 hour to 5 hours, although it depends on compounds.

A solvent includes, for example, ethers such as diethyl ether, dioxane and tetrahydrofuran (THF); halogenated hydro-carbons such as dichloromethane, dichloroethane, tetrachloride, chlorobenzene and dichlorobenzene; amides such as N,N-dimethylacetamide, N,N-dimethylformamide (DMF) and N-methyl-2-pyrrolidinone; sulfur compounds such as dimethylsulfoxide (DMSO) and sulfolane; esters such as ethyl acetate; aromatic hydrocarbons such as benzene, toluene and xylene; ketones such as acetone and 2-butanone; nitriles such as acetonitrile; pyridine, water or a mixture thereof.

A base includes, for example, organic bases such as pyridine, triethylamine, dimethylaminopyridine or 1,8-diazabicyclo[5.4.0]-7-undecene; inorganic salts including hydroxides of alkali metals such as sodium hydroxide and potassium hydroxide; hydroxides of alkali earth metals such as calcium hydroxide and magnesium hydroxide; carbonate salts of alkali metals such as sodium carbonate and potassium carbonate; bicarbonates of alkali metals such as sodium hydrogen carbonate and potassium hydrogen carbonate.

A raw material compound [12] is either obtained as a commercial product, or can be synthesized by reacting a compound [5] with thionyl chloride or oxalyl chloride.

A raw material compound [13] can be synthesized by the following method:

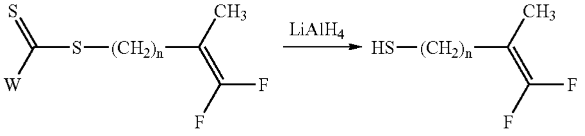

[4] [13]

(wherein W and n represent the same meaning described above.)

A compound [4] can be synthesized by reacting a compound [2] with a dialkyldithiocarbamate salt in a solvent.

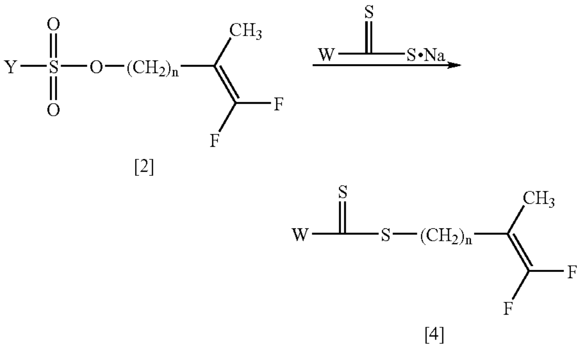

[2] [4]

(wherein Y, W and n represent the same meaning described above.)

<Production Method 3>

A compound [1b-1] or [1b-2] of the present invention can also be synthesized, as shown below, by reacting a compound [5] with a compound [6] or a compound [13] in a solvent in the presence of a dehydrating-condensing agent:

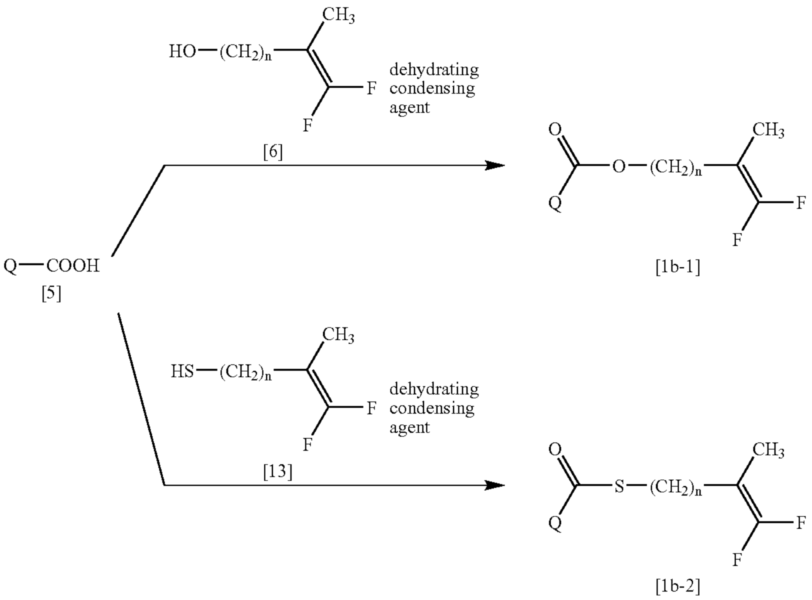

[6] [1b-1] [5] [13] [1b-2]

(wherein Q and n represent the same meaning described above.)

Molar ratio of raw materials can be set arbitrarily, but, in general, the ratio of a compound [6] or a compound [13] is 0.5 to 2 equivalents to 1 equivalent of a compound [5].

Reaction temperature in any reaction can be set arbitrarily from −20° C. to refluxing temperature of a reaction system, and preferably in the range from 0° C. to 60° C., and reaction is completed within 0.5 hour to 50 hours, although it depends on compounds.

A catalytic amount of 1-hydroxybenzotriazole, 3-hydroxy-4-oxo-3,4-dihydro-1,2,3-benzotriazine, dimethylaminopyridine or the like may be added depending on a dehydrating-condensing agent used.

A solvent includes, for example, ethers such as diethyl ether, dioxane and tetrahydrofuran (THF); halogenated hydrocarbons such as dichloromethane, dichloroethane, carbon tetrachloride, chlorobenzene and dichlorobenzene; amides such as N,N-dimethylacetamide, N,N-dimethylformamide (DMF) and N-methyl-2-pyrrolidinone; sulfur compounds such as dimethylsulfoxide (DMSO) and sulfolane; aromatic hydrocarbons such as benzene, toluene and xylene; ketones such as acetone and 2-butanone; nitrites such as acetonitrile; pyridine or a mixture thereof.

A dehydrating-condensing agent includes, for example, dicyclohexylcarbodiimide (DCC), N-ethyl-N'-3-dimethylaminopropylcarbodiimide (WSC) and a hydrochloric acid salt thereof, benzotriazole-1-yl-tris(pyrrolidino)phosphonium hexafluorophosphide salt (PYBOP), 1,1'-carbonyldiimidazole (CDI) and a combination of triphenylphosphine and azodicarboxylate ester.

<Production Method 4>

A compound [1c] of the present invention can be synthesized by reacting a compound [1b] with a sulfiding agent in a solvent.

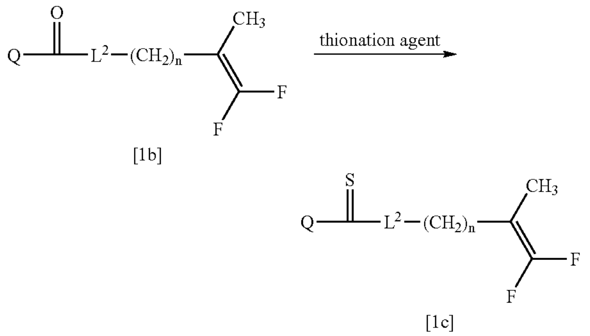

[1b] [1c]

(wherein Q, $L^2$ and n represent the same meaning described above.)

A ratio by equivalent in the reaction can be set arbitrarily, but, in general, the ratio of a sulfiding agent is 1 to 20 equivalents to 1 equivalent of a compound [1b].

Reaction temperature in any reaction can be set arbitrarily from 0° C. to refluxing temperature of a reaction system, and preferably in the range from room temperature to 180° C., and the reaction is completed within 0.5 hour to 50 hours, although it depends on compounds.

A solvent includes, for example, ethers such as dioxane and tetrahydrofuran (THF); halogenated hydrocarbons such as dchloroform, dichloroethane, carbon tetrachloride, chlorobenzene and dichlorobenzene; aromatic hydrocarbons such as benzene, toluene and xylene; aromatic heteroaryls such as pyridine and quinoline; nitrites such as acetonitrile.

A thionation agent includes, for example, Lawesson's reagent, diphosphorus pentasulfide and the like.

<Production Method 5>

A compound [1e] of the present invention can be synthesized by reacting a compound [1d] with a compound [14] in a solvent in the presence of a base.

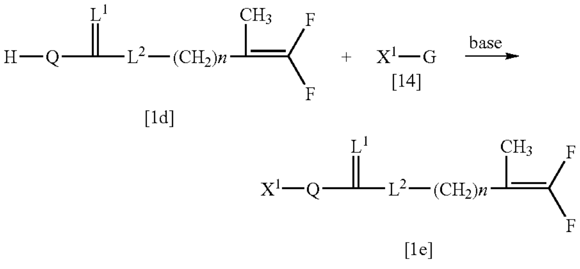

[1d] [14] [1e]

[wherein $L^1$, $L^2$ and n represent the same meaning described above, Q represents $Q^9$, $Q^{14}$, $Q^{15}$, $Q^{18}$, $Q^{26}$, $Q^{31}$, $Q^{32}$ or $Q^{33}$, and $X^1$ represents an alkyl group having 1 to 6 carbon atoms which may be mono-substituted with any group selected from substituents group α, a haloalkyl group having 1 to 4 carbon atoms, an alkoxyalkyl group having 2 to 6 carbon atoms, an alkenyl group having 3 to 6 carbon atoms, a haloalkenyl group having 3 to 7 carbon atoms, an alkynyl group having 3 to 6 carbon atoms, a cycloalkyl group having 3 to 6 carbon atoms or a cycloalkylalkyl group having 4 to 7 carbon atoms (said group may be substituted with a halogen atom or an alkyl group) and substituents group α represents the same meaning described above, and G represents a chlorine atom, a bromine atom, an iodine atom or a methanesulfonyloxy group.]

This reaction is carried out, in general, at reaction temperature from 0° C. to 120° C. for 10 minutes to 24 hours. Amounts of reagents fed to the reaction are 1 to 20 equivalents of a compound [14] and 1 to 3 equivalents of a base to 1 equivalent of a compound [1d].

A base and a solvent include, for example, similar ones used in the production method 1.

<Production Method 6>

A compound [1g] of the present invention can be synthesized by reacting a compound [1f] with an acid halide or an acid anhydride in a solvent in the presence of a base, or by reacting with an acid anhydride as a solvent.

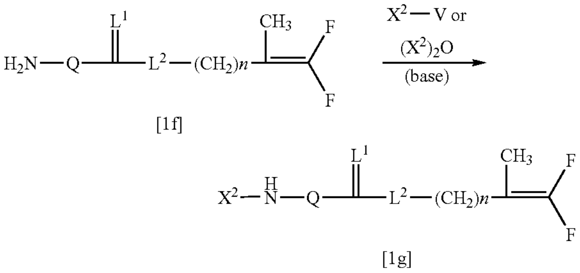

[1f] [1g]

(wherein Q, $L^1$, $L^2$, n and V represent the same meaning described above, $X^2$ represents an acyl group having 1 to 6 carbon atoms which may be mono-substituted with any group selected from substituents group α, an alkylsulfonyl group having 1 to 6 carbon atoms which may be mono-substituted with any group selected from substituents group α, a haloalkylcarbonyl group having 2 to 5, a haloalkylsulfonyl group having 1 to 4 carbon atoms, a benzoyl group which may be substituted with any 1 to 4 groups selected from substituents group β or a phenylsulfonyl group which may be substituted with any 1 to 4 groups selected from substituents group β. Substituents group α and substituents group β represent the same meaning described above.)

This reaction is carried out, in general, at reaction temperature from −20° C. to 140° C. for 10 minutes to 24 hours. Amounts of reagents fed to the reaction are 1 to 20 equivalents of an acid chloride or an acid anhydride and 1 to 3 equivalents of a base to 1 equivalent of a compound [1f].

A base and a solvent include, for example, similar ones used in the production method 2.

<Production Method 7>

A compound [1i] of the present invention can be synthesized by reacting a compound [1 h] with a compound [14] in a solvent in the presence of a base.

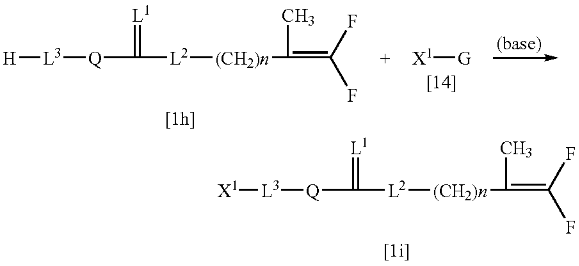

[1h] [14] [1i]

[wherein Q, $L^1$, $L^2$, n, $X^1$ and G represent the same meaning described above; $L^3$ represents —O— or —N(R)—, wherein R represents a hydrogen atom, an alkyl group having 1 to 12 carbon atoms which may be mono-substituted with any group selected from substituents group α, a cycloalkyl group having 3 to 6 carbon atoms, an alkoxy group having 1 to 12 carbon atoms which may be mono-substituted with any group selected from substituents group α, a phenyl group which may be substituted with any 1 to 4 groups selected from substituents group β, an acyl group having 1 to 6 carbon atoms which may be mono-substituted with any group selected from substituents group α, a haloalkylcarbonyl group having 2 to 5 carbon atoms, an alkylsulfonyl group having 1 to 6 carbon atoms which may be mono-substituted with any group selected from substituents group α, a haloalkylsulfonyl group having 1 to 4 carbon atoms, a benzoyl group which may be substituted with any 1 to 4 groups selected from substituents group β or a phenylsulfonyl group which may be substituted with any 1 to 4 groups selected substituents group β. Substituents group α and substituents group β represent the same meaning described above.]

This reaction is carried out, in general, at reaction temperature from 0° C. to 120° C. for 10 minutes to 24 hours. Amounts of reagents fed to the reaction are 1 to 20 equivalents of a compound [14] and 1 to 3 equivalents of a base to 1 equivalent of a compound [1h].

A base and a solvent include, for example, similar ones used in the production method 1.

<Production Method 8>

A compound [1j] of the present invention can be synthesized by the following method:

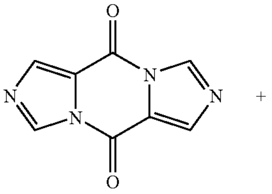

[15]

-continued

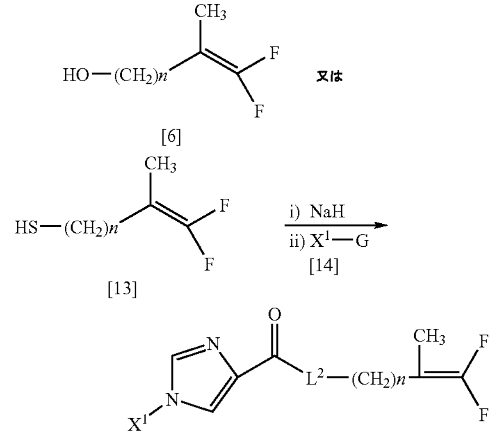

[6] 又は [13] [1j]

(wherein $L^2$, n, $X^1$ and G represent the same meaning described above.)

This reaction is carried out, in general, at reaction temperature from 0° C. to 120° C. for 10 minutes to 24 hours.

Amounts of reagents fed to the reaction are 1 to 3 equivalents of a compound [6] or a compound [13], 1 to 3 equivalents of sodium hydride and 1 to 20 equivalents of a compound [14] to 1 equivalent of a compound [15]. A solvent includes, for example, ethers such as diethyl ether, dioxane and tetrahydrofuran (THF); halogenated hydrocarbons such as dichloromethane, dichloroethane, carbon tetrachloride, chlorobenzene and dichlorobenzene; amides such as N,N-dimethylacetamide, N,N-dimethylformamide (DMF) and N-methyl-2-pyrrolidinone; sulfur compounds such as dimethylsulfoxide (DMSO) and sulfolane; aromatic hydrocarbons such as benzene, toluene and xylene; ketones such as acetone and 2-butanone; nitrites such as acetonitrile; or a mixture thereof.

A compound [15] can be synthesized by reacting imidazole-4-carboxylic acid with thionyl chloride in the presence of the catalytic amount of N,N-dimethylformamide.

<Production Method 9>

A compound [1 m] of the present invention can be synthesized by reacting a compound [1k] with an oxidizing agent in a solvent.

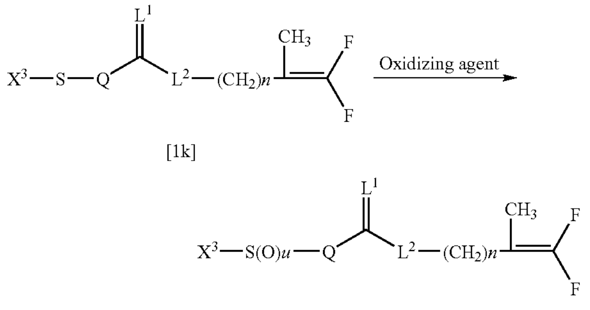

[1k] [1m]

(wherein Q, $L^1$, $L^2$ and n represent the same meaning described above, $X^3$ represents an alkyl group having 1 to 12 carbon atoms which may be mono-substituted with any group selected from substituents group α or a phenyl group which may be substituted with any 1 to 4 groups selected from substituents group β, and u represents 1 or 2. Substituents group α and substituents group β represent the same meaning described above.)

This reaction is carried out, in general, at reaction temperature from −20° C. to 100° C. for 10 minutes to 24 hours.

Amount of an oxidizing agent fed to the reaction is 1 to 20 equivalents to 1 equivalent of a compound [1k]. A solvent includes, for example, halogenated hydrocarbons such as dichloromethane, chloroform, dichloroethane, carbon tetrachloride, chlorobenzene and dichlorobenzene; amides such as N,N-dimethylacetamide, N,N-dimethylformamide (DMF) and N-methyl-2-pyrrolidinone; aromatic hydrocarbons such as benzene, toluene and xylene; ketones such as acetone and 2-butanone; nitriles such as acetonitrile; alcohols such as methanol and ethanol; acetic acid, water or a mixture thereof.

An oxidizing agent includes m-chloroperbenzoic acid, "Oxon" (a trade name of 2 $KHSO_5 \cdot KHSO4 \cdot K_2SO_4$), or a combination of hydrogen peroxide and sodium tungstate.

<Manufacturing Method 10>

A compound [1k], [1n] or [1p] of the present invention can be synthesized by the following method.

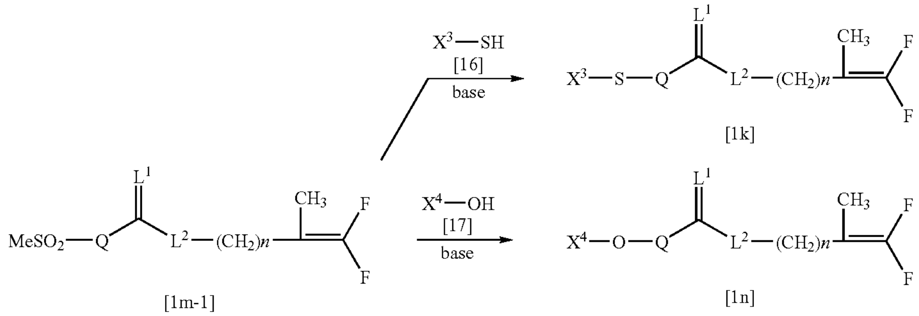

[1m-1] [1k] [1n]

-continued

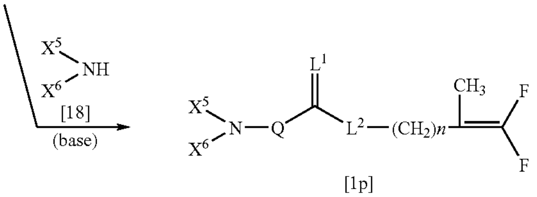

[1p]

(wherein Q, $L^1$, $L^2$, n and $X^3$ represent the same meaning described above; $X^4$ represents an alkyl group having 1 to 12 carbon atoms which may be mono-substituted with any group selected from substituents group α, a haloalkyl group having 1 to 4 carbon atoms, an alkoxyalkyl group having 2 to 6 carbon atoms, an alkenyl group having 3 to 8 carbon atoms, an haloalkenyl group having 3 to 8 carbon atoms, an alkynyl group having 3 to 6 carbon atoms, a cycloalkyl group having 3 to 7 carbon atoms, a cycloalkylalkyl group having 4 to 7 carbon atoms (said group may be substituted with a halogen atom or an alkyl group), a phenyl group which may be substituted with any 1 to 4 groups selected from substituents group β or a pyridyl group which may be substituted with any 1 to 4 groups selected substituents group β; $X^5$ represents an alkyl group having 1 to 12 carbon atoms which may be mono-substituted with any group selected from substituents group α, a cycloalkyl group having 3 to 6 carbon atoms, an alkoxy group having 1 to 12 carbon atoms which may be mono-substituted with any group selected from substituents group α or a phenyl group which may be substituted with any 1 to 4 groups selected from substituents group α; $X^6$ represents a hydrogen atom, an alkyl group having 1 to 12 carbon atoms which may be mono-substituted with any group selected from substituents group α or $X^5$, $X^6$ and said nitrogen atom all together represent a pyrrolidinyl group, a piperidinyl group or a phthalimide group. Substituents group α and substituents group β represent the same meaning described above.)

This reaction is carried out, in general, at reaction temperature at from −20° C. to 120° C. for 10 minutes to 24 hours.

Amounts of reagents fed to the reaction are 1 to 10 equivalents of a compound [16], [17] or [18] and 0 to 5 equivalents of a base to 1 equivalent of a compound [1m-1].

A base and a solvent include, for example, similar ones to those in the production method 1.

Herein, the entireties of JP Application No. 2001-299687 and JP Application No. 2002-142329 are incorporated as a part of the present invention.

EXAMPLES

A production method for a compound of the present invention, a preparation method and applications thereof are described specifically hereinbelow using Examples, but the present invention is by no means limited thereto. Production Examples of a compound of the present invention are shown first.

Production Example 1

Production of Compound (18) by the Production Method 1

To 5 ml of N,N-dimethylformamide were dissolved 0.40 g (1.8 mmol) of 4,4-difluoro-3-methyl-3-butenyl methanesulfonate and 0.33 g (1.9 mmol) of benzo[b]thiophene-2-carboxylicacid, followed by the addition of 0.46 g (5.5 mmol) of sodium hydrogencarbonate and stirring at 100° C. for 2 hours. The reaction liquid was then poured in water and extracted with diethyl ether. The organic layer was washed with water and a saturated saline solution in this order, followed by drying over anhydrous magnesium sulfate and concentrating under reduced pressure. The residue was purified with silica gel column chromatography (diisopropyl ether:hexane=1:7) to obtain 0.48 g (yield: 93%) of 4,4-difluoro-3-methyl-3-butenyl benzo[b]thiophene-2-carboxylate.

$^1$H-NMR ($CDCl_3$, TMS) δ ppm: 1.69 (3H, t), 2.42-2.49 (2H, m), 4.41 (2H, t), 7.38-7.49 (2H, m), 7.85-7.90 (2H, m), 8.05 (1H, s)

Production Example 2

Production of Compound (3) by the Production Method 1

To 40 ml of N,N-dimethylformamide were dissolved 5.00 g (22 mmol) of 6,6-difluoro-5-methyl-5-hexenyl methanesulfonate and 4.30 g (24 mmol) of benzo[b]thiophene-2-carboxylicacid, followed by the addition of 6.00 g (71 mmol) of sodium hydrogencarbonate and stirring at 100° C. for 3 hours. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (diisopropyl ether:hexane=1:7) to obtain 5.50 g (yield: 81%) of 6,6-difluoro-5-methyl-5-hexenyl benzo[b]thiophene-2-carboxylate.

$^1$H-NMR ($CDCl_3$, TMS) δ ppm: 1.52-1.62 (5H, m), 1.73-1.83 (2H, m), 2.03-2.09 (2H, m), 4.36 (2H, t), 7.38-7.49 (2H, m), 7.85-7.90 (2H, m), 8.06 (1H, s)

Production Example 3

Production of Compound (6) by then Production Method 1

To 20 ml of N,N-dimethylformamide were dissolved 1.50 g (6.6 mmol) of 6,6-difluoro-5-methyl-5-hexenylmethanesulfonate and 1.30 g (8.1 mmol) of 1H-indole-2-carboxylicacid, followed by the addition of 1.40 g (17 mmol) of sodium hydrogencarbonate and stirring at 100° C. for 3 hours. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (ethyl acetate:hexane=1:4) to obtain 1.70 g (yield: 88%) of 6,6-difluoro-5-methyl-5-hexenyl 1H-indole-2-carboxylate.

$^1$H-NMR ($CDCl_3$, TMS) δ ppm: 1.52-1.62 (5H, m), 1.73-1.83 (2H, m), 2.03-2.09 (2H, m), 4.36 (2H, t), 7.16 (1H, t), 7.23 (1H, s), 7.33 (1H, t), 7.43 (1H, d), 7.70 (1H, d), 8.92 (1H, br.s)

Production Example 4

Production of Compound (15) by the Production Method 1

To 7 ml of N,N-dimethylformamide were dissolved 0.68 g (3.0 mmol) of 6,6-difluoro-5-methyl-5-hexenylmethanesulfonate and 0.58 g (3.6 mmol) of 1H-indole-5-carboxylic acid, followed by the addition of 0.75 g (8.9 mmol) of sodium hydrogencarbonate and stirring at 100° C. for 3 hours. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (ethyl acetate:hexane=1:3) to obtain 0.81 g (yield: 93%) of 6,6-difluoro-5-methyl-5-hexenyl 1H-indole-5-carboxylate.

$^1$H-NMR ($CDCl_3$, TMS) δ ppm: 1.52-1.62 (5H, m), 1.73-1.83 (2H, m), 2.03-2.09 (2H, m), 4.35 (2H, t), 6.66-6.67 (1H, m), 7.27-7.29 (1H, m), 7.41 (1H, d), 7.91 (1H, d), 8.37 (1H, br.s), 8.42 (1H, s)

Production Example 5

Production of compound (26) by the production method 1

To 10 ml of N,N-dimethylformamide were dissolved 0.50 g (2.2 mmol) of 6,6-difluoro-5-methyl-5-hexenyl methanesulfonate and 0.45 g (2.4 mmol) of 4-chloro-5-ethyl-2-methyl-2H-pyrazole-3-carboxylic acid, followed by the addition of 0.37 g (4.4 mmol) of sodium hydrogencarbonate and stirring at 100° C. for 7 hours. The reaction liquid was then poured in water and extracted with ethyl acetate. The organic layer was washed with water and a saturated saline solution in this order, followed by drying over anhydrous magnesium sulfate and concentration under reduced pressure. The residue was purified with silica gel column chromatography (ethyl acetate:hexane=1:19) to obtain 0.52 g (yield: 74%) of 6,6-difluoro-5-methyl-5-hexenyl 4-chloro-5-ethyl-2-methyl-2H-pyrazole-3-carboxylate.

$^1$H-NMR ($CDCl_3$, TMS) δ ppm: 1.24 (3H, t), 1.54-1.64 (5H, m), 1.71-1.80 (2H, m), 2.01-2.07 (2H, m), 2.65 (2H, q), 4.10 (3H, s), 4.34 (2H, t)

Production Example 6

Production of Compound (29) by the Production Method 1

To 10 ml of N,N-dimethylformamide were dissolved 0.50 g (2.2 mmol) of 6,6-difluoro-5-methyl-5-hexenyl methanesulfonate and 0.53 g (2.4 mmol) of 4-methyl-2-phenylthiazole-5-carboxylic acid, followed by the addition of 0.37 g (4.4 mmol) of sodium hydrogencarbonate and stirring at 100° C. for 6 hours. The reaction liquid was then poured in water and extracted with ethyl acetate. The organic layer was washed with water and a saturated saline solution in this order, followed by drying over anhydrous magnesium sulfate and concentration under reduced pressure. The residue was purified with silica gel column chromatography (ethyl acetate:hexane=1:19) to obtain 0.57 g (yield: 74%) of 6,6-difluoro-5-methyl-5-hexenyl 4-methyl-2-phenylthiazole-5-carboxylate.

$^1$H-NMR ($CDCl_3$, TMS) δ ppm: 1.50-1.60 (5H, m), 1.70-1.79 (2H, m), 2.02-2.08 (2H, m), 2.79 (3H, s), 4.31 (2H, t), 7.42-7.47 (3H, m), 7.95-7.98 (2H, m)

Production Example 7

Production of Compound (42) by the Production Method 1

To 30 ml of ethanol was dissolved 2.0 g (10 mmol) of methyl benzo[1,2,5]thiadiazole-5-carboxylate, followed by the addition of 3.3 g of a 25% aqueous solution of sodium hydroxide and stirring at room temperature for 3 hours. To the reaction liquid was added 50 ml of water and a dilute hydrochloric acid to make pH of 2. Crystal precipitated was filtered off and dried under reduced pressure to obtain 1.7 g (yield: 92%) of benzo[1,2, 5]thiadiazole-5-carboxylic acid. In a separate reactor, 0.50 g (2.2 mmol) of 6,6-difluoro-5-methyl-5-hexenyl methanesulfonate and 0.43 g (2.4 mmol) of benzo[1,2,5]thiadiazole-5-carboxylic acid were dissolved in 7 ml of N,N-dimethylformamide, followed by the addition of 0.37 g (4.4 mmol) of sodium hydrogencarbonate and stirring at 100° C. for 3 hours. The reaction liquid was then poured in water and extracted with ethyl acetate. The organic layer was washed with water and a saturated saline solution in this order, followed by drying over anhydrous magnesium sulfate and concentration under reduced pressure. The residue was purified with silica gel column chromatography (ethyl acetate:hexane=1:19) to obtain 0.44 g (yield: 64%) of 6,6-difluoro-5-methyl-5-hexenyl benzo[1,2,5]thiadiazole-5-carboxylate.

$^1$H-NMR ($CDCl_3$, TMS) δ ppm: 1.55-1.65 (5H, m), 1.77-1.87 (2H, m), 2.05-2.11 (2H, m), 4.42 (2H, t), 8.06 (1H, d), 8.22 (1H, d), 8.75 (1H, d)

Production Example 8

Production of Compound (56) by the Production Method 1

To 7 ml of N,N-dimethylformamide were dissolved 0.92 g (4.0 mmol) of 6,6-difluoro-5-methyl-5-hexenyl methanesulfonate and 0.72 g (5.2 mmol) of 6-aminonicotinic acid, followed by the addition of 1.30 g (16 mmol) of sodium hydrogencarbonate and stirring at 100° C. for 3 hours. The reaction liquid was then poured in water and extracted with ethyl acetate. The organic layer was washed with water and a saturated saline solution in this order, followed by drying over anhydrous magnesium sulfate and concentration under reduced pressure. The residue was purified with silica gel column chromatography (ethyl acetate:hexane=1:1) to obtain 0.85 g (yield: 78%) of 6,6-difluoro-5-methyl-5-hexenyl 6-aminonicotinate.

$^1$H-NMR ($CDCl_3$, TMS) δ ppm: 1.51-1.60 (5H, m), 1.69-1.79 (2H, m), 2.00-2.07 (2H, m), 4.29 (2H, t), 4.85 (2H, br.s), 6.48 (1H, d), 8.02 (1H, dd), 8.74 (1H, d)

Production Example 9

Production of Compound (10) by the Production Method 1

To 10 ml of N,N-dimethylformamide were dissolved 0.29 g (1.1 mmol) of 8,8-difluoro-7-methyl-7-octenyl methanesulfonate and 0.26 g (1.5 mmol) of benzo[b]thiophene-2-carboxylic acid, followed by the addition of 0.28 g (3.3 mmol) of sodium hydrogencarbonate and stirring at 100° C. for 3 hours. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (diisopropyl ether:hexane=1:8) to obtain 0.27 g (yield: 71%) of 8,8-difluoro-7-methyl-7-octenyl benzo[b]thiophene-2-carboxylate.

$^{1}$H-NMR ($CDCl_3$, TMS) δ ppm: 1.34-1.52 (6H, m), 1.55 (3H, t), 1.74-1.84 (2H, m), 1.95-2.00 (2H, m), 4.35 (2H, t), 7.38-7.49 (2H, m), 7.85-7.90 (2H, m), 8.06 (1H, s)

Production Example 10

Production of Compound (4) by the Production Method 2

A mixture consisting of 1.1 g (6.0 mmol) of 4,6-dimethoxypyrimidine-2-carboxylic acid, obtained in accordance with a method descibed in the specification of WO 9318012 A1, 1.1 g (9.0 mmol) of thionyl chloride, one drop of N,N-dimethylformamide and 5 ml of toluene was stirred under heating and refluxing for 3 hours. After the reaction, excess thionyl chloride and the solvent were removed under reduced pressure to obtain crystal of 4,6-dimethoxypyrimidine-2-carbonylchloride. In a separate vessel, 0.30 g (2.0 mmol) of 6,6-difluoro-5-methyl-5-hexenole and 0.61 g (3.0 mmol) of 4,6-dimethoxypyrimidine-2-carbonylchloride were dissolved in 10 ml of tetrahydrofuran, followed by the drop-wise addition of 0.40 g (4.0 mmol) of triethylamine at room temperature, followed by stirring at the same temperature for 1 hour. The reaction liquid was then poured in water and extracted with ethyl acetate. The organic layer was washed with water and a saturated saline solution in this order, followed by drying over anhydrous magnesium sulfate and concentration under reduced pressure. The residue was purified with silica gel column chromatography (ethyl acetate:hexane=1:7) to obtain 0.20 g (yield: 21%) of 6,6-difluoro-5-methyl-5-hexenyl 4,6-dimethoxypyrimidine-2-carboxylate.

$^{1}$H-NMR ($CDCl_3$, TMS) δ ppm: 1.51-1.62 (5H, m), 1.75-1.84 (2H, m), 2.02-2.08 (2H, m), 4.02 (6H, s), 4.40 (2H, t), 6.16 (1H, s)

Production Example 11

Production of compound (45) by the production method 2

To 30 ml of tetrahydrofuran were dissolved 1.10 g (5.6 mmol) of benzo[d]isothiazole-3-carbonylchloride, obtained in accordance with the method described in "J. Med. Chem.", page 2308 to 2314 (1994) and 0.59 g (3.9 mmol) of 6,6-difluoro-5-methyl-5-hexenole, followed by the drop-wise addition of 0.74 g (7.3 mmol) of triethylamine at room temperature and stirring at the same temperature for 1 hour. The reaction liquid was then poured in water and extracted with ethyl acetate. The organic layer was washed with water and a saturated saline solution in this order, followed by drying over anhydrous magnesium sulfate and concentration under reduced pressure. The residue was purified with silica gel column chromatography (ethyl acetate:hexane=1:9) to obtain 1.00 g (yield: 82%) of 6,6-difluoro-5-methyl-5-hexenyl benzo[d]isothiazole-3-carboxylate.

$^{1}$H-NMR ($CDCl_3$, TMS) δ ppm: 1.55-1.65 (5H, m), 1.83-1.92 (2H, m), 2.04-2.10 (2H, m), 4.50 (2H, t), 7.52-7.62 (2H, m), 7.99 (1H, d), 8.76 (1H, d)

Production Example 12

Production of Compound (52) by the Production Method 2

A mixture consisting of 1.00 g (6.3 mmol) of 6-chloronicotinic acid, 5 ml of thionyl chloride and three drops of N,N-dimethylformamide was stirred under heating and refluxing for 3 hours. After the reaction, excess thionyl chloride was removed under reduced pressure, followed by the addition of 10 ml of toluene and removing the solvent again under reduced pressure to obtain crystal of 6-chloronicotinoyl chloride. In a separate vessel, 0.50 g (3.0 mmol) of 6,6-difluoro-5-methyl-5-hexene-1-thiol and 0.80 g (4.5 mmol) of 6-chloronicotinoyl chloride were dissolved in 10 ml of tetrahydrofuran, followed by the drop-wise addition of 0.50 g (4.9 mmol) of triethylamine at room temperature and stirring at the same temperature for 1 hour. The reaction liquid was then poured in water and extracted with ethyl acetate. The organic layer was washed with water and a saturated saline solution in this order, followed by drying over anhydrous magnesium sulfate and concentration under reduced pressure. The residue was purified with silica gel column chromatography (diisopropyl ether:hexane=1:6) to obtain 0.80 g (yield: 87%) of S-(6,6-difluoro-5-methyl-5-hexenyl) 6-chlorothionicotinate.

$^{1}$H-NMR ($CDCl_3$, TMS) δ ppm: 1.48-1.58 (5H, m), 1.63-1.73 (2H, m), 1.99-2.05 (2H, m), 3.12 (2H, t), 7.43 (1H, d), 8.16 (1H, dd), 8.95(1H, d)

Production Example 13

Production of Compound (53) by the Production Method 2

To 10 ml of tetrahydrofuran were dissolved 0.25 g (1.5 mmol) of 6,6-difluoro-5-methyl-5-hexene-1-thiol and 0.39 g (2.0 mmol) of benzo[b]thiophene-2-carbonylchloride, followed by the drop-wise addition of 0.30 g (3.0 mmol) of triethylamine at room temperature, followed by stirring at the same temperature for 1 hour. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (diisopropyl ether:hexane=1:20) to obtain 0.39 g (yield: 80%) of S-(6,6-difluoro-5-methyl-5-hexenyl) benzo[b]thiophene-2-thiocarboxylate.

$^{1}$H-NMR ($CDCl_3$, TMS) δ ppm: 1.50-1.60 (5H, m), 1.65-1.75 (2H, m), 1.99-2.05 (2H, m), 3.13(2H, t), 7.38-7.49 (2H, m), 7.85-7.90 (2H, m), 8.05 (1H, s)

Production Example 14

Production of Compound (1) by the Production Method 3

To 10 ml of dichloromethane were dissolved 0.35 g (2.2 mmol) of 6-chloronicotinic acid, 0.40 g (2.7 mmol) of 6,6-difluoro-5-methyl-5-hexenole and 0.33 g (2.7 mmol) of dimethylaminopyridine, followed by the addition of 0.51 g (2.7 mmol) of N-ethyl-N'-3-dimethylaminopropyl-carbodiimide (WSC) hydrochloric acid salt at room temperature and stirring at the same temperature for 15 hours. The reaction liquid was then poured in water and extracted with dichloromethane. The organic layer was washed with water and a saturated saline solution in this order, followed by drying over anhydrous magnesium sulfate and concentration under reduced pressure. The residue was purified with silica gel column chromatography (ethyl acetate:hexane=1:9) to obtain 0.59 g (yield: 92%) of 6,6-difluoro-5-methyl-5-hexenyl 6-chloronicotinate.

$^{1}$H-NMR ($CDCl_3$, TMS) δ ppm: 1.50-1.59 (5H, m), 1.72-1.81 (2H, m), 2.02-2.07 (2H, m), 4.37 (2H, t), 7.42 (1H, d), 8.24 (1H, dd), 8.99 (1H, d)

Production Example 15

Production of Compound (11) by the Production Method 3

To 4 ml of dichloromethane were dissolved 0.23 g (1.1 mmol) of 4-phenyl[1,2,3]thiadiazole-5-carboxylic acid, 0.17 g (1.1 mmol) of 6,6-difluoro-5-methyl-5-hexenole and 0.13 g (1.1 mmol) of dimethylaminopyridine, followed by the addition of 0.29 g (1.5 mmol) of N-ethyl-N'-3-dimethylaminopropylcarbodiimide (WSC) hydrochloric acid salt at room temperature and stirring at the same temperature for 20 hours. The reaction liquid was then poured in water and extracted with dichloromethane. The organic layer was washed with water and a saturated saline solution in this order, followed by drying over anhydrous magnesium sulfate and concentration under reduced pressure. The residue was purified with silica gel column chromatography (diisopropyl ether:hexane=1:6) to obtain 0.27 g (yield: 66%) of 6,6-difluoro-5-methyl-5-hexenyl 4-phenyl[1,2,3]thiadiazole-5-carboxylate.

$^1$H-NMR ($CDCl_3$, TMS) δ ppm: 1.37-1.47 (2H, m), 1.54 (3H, m), 1.63-1.73 (2H, m), 1.95-2.01 (2H, m), 4.32 (2H, t) 7.50-7.54 (3H, m), 7.87-7.90 (2H, m)

Production Example 16

Production of Compound (21) by the Production Method 3

To 4 ml of dichloromethane were dissolved 0.24 g (1.3 mmol) of benzothiazole-2-carboxylic acid, manufactured by a method described in "J. Amer. Chem. Soc.", page 2328 (1949), 0.17 g (1.1 mmol) of 6,6-difluoro-5-methyl-5-hexenol and 0.13 g (1.1 mmol) of dimethylaminopyridine, followed by the addition of 0.38 g (2.0 mmol) of N-ethyl-N'-3-dimethyl-aminopropylcarbodiimide (WSC) hydrochloric acid salt at room temperature and stirring at the same temperature for 20 hours. The reaction liquid was then poured in water and extracted with dichloromethane. The organic layer was washed with water and a saturated saline solution in this order, followed by drying over anhydrous magnesium sulfate and concentration under reduced pressure. The residue was purified with silica gel column chromatography (ethyl acetate:hexane=1:6) to obtain 0.15 g (yield: 43%) of 6,6-difluoro-5-methyl-5-hexenyl benzothiazole-2-carboxylate.

$^1$H-NMR ($CDC_1$, TMS) δ ppm: 1.53-1.63 (5H, m), 1.81-1.90 (2H, m), 2.04-2.09 (2H, m), 4.50 (2H, t), 7.53-7.62 (2H, m), 7.98 (1H, d) 8.26 (1H, d)

Production Example 17

Production of Compound (55) by the Production Method 4

To 5 ml of 2-chlorotoluene was dissolved 0.20 g (0.64 mmol) of 6,6-difluoro-5-methyl-5-hexenyl benzo[b]thiophene-2-carboxylate, followed by the addition of 0.26 g (0.64 mmol) of Lawesson's reagent and stirring by heating under refluxing for 4 hours. To the reaction liquid were added 2 ml of isopropyl ether and 10 ml of hexane and precipitated solid was filtered off. The filtrate was concentrated under reduced pressure and the residue was purified with silica gel column chromatography (diisopropyl ether:hexane=1:30) to obtain 0.17 g (yield: 81%) of O-(6,6-difluoro-5-methyl-5-hexenyl) benzo[b]thiophene-2-thiocarboxylate.

$^1$H-NMR ($CDCl_3$, TMS) δ ppm: 1.58-1.68 (5H, m), 1.85-1.95 (2H, m), 2.05-2.11 (2H, m), 4.67 (2H, t), 7.38 (1H, t), 7.45 (1H, t), 7.81 (1H, d), 7.87 (1H, d), 8.09 (1H, s)

Production Example 18

Production of Compound (16) by the Production Method 5

To 5 ml of N,N-dimethylformamide were dissolved 0.40 g (1.4 mmol) of 6,6-difluoro-5-methyl-5-hexenyl 1H-indole-5-carboxylate and 0.40 g (2.8 mmol) of methyl iodide, followed by the addition of 0.07 g (1.7 mmol) of sodium hydride at room temperature and stirring at the same temperature for 1 hour. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (ethyl acetate:hexane=1:5) to obtain 0.36 g (yield: 86%) of 6,6-difluoro-5-methyl-5-hexenyl 1-methyl-1H-indole-5-carboxylate.

$^1$H-NMR ($CDCl_3$, TMS) δ ppm: 1.54-1.64 (5H, m), 1.74-1.83 (2H, m), 2.03-2.09 (2H, m), 3.83 (3H, s), 4.34 (2H, t), 6.59 (1H, d), 7.11 (1H, d), 7.33 (1H, d), 7.93 (1H, dd), 8.39 (1H, d)

Production Example 19

Production of Compound (25) by the Production Method 5

To 5 ml of N,N-dimethylformamide were dissolved 0.32 g (1.1 mmol) of 6,6-difluoro-5-methyl-5-hexenyl 1H-indole-2-carboxylate and 0.34 g (2.2 mmol) of ethyl iodide, followed by the addition of 0.06 g (1.5 mmol) of sodium hydride at room temperature and stirring at the same temperature for 1 hour. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (ethyl acetate:hexane=1:5) to obtain 0.31 g (yield: 88%) of 6,6-difluoro-5-methyl-5-hexenyl 1-ethyl-1H-indole-2-carboxylate.

$^1$H-NMR ($CDCl_3$, TMS) δ ppm: 1.40 (3H, t), 1.53-1.63 (5H, m), 1.73-1.83 (2H, m), 2.03-2.09 (2H, m), 4.33 (2H, t), 4.63 (2H, q), 7.15 (1H, t), 7.29 (1H, s), 7.30-7.42 (2H, m), 7.68 (1H, d)

Production Example 20

Production of a Compound (35) and a Compound (36) by the Production Method 1 and the Production Method 5

To 5 ml of N,N-dimethylformamide were dissolved 0.68 g (3.0 mmol) of 6,6-difluoro-5-methyl-5-hexenyl methanesulfonate and 0.24 g (1.5 mmol) of 1H-benzoimidazole-5-carboxylic acid, followed by the addition of 0.42 g (5.0 mmol) of sodium hydrogencarbonate and stirring at 100° C. for 3 hours. The reaction liquid was then poured in water and extracted with ethyl acetate. The organic layer was washed with water and a saturated saline solution in this order, followed by drying over anhydrous magnesium sulfate and concentration under reduced pressure. The residue was purified with silica gel column chromatography (ethyl acetate:hexane 1:2) to obtain 0.22 g (yield: 35%) of 6,6-difluoro-5-methyl-5-hexenyl 1-(6,6-difluoro-5-methyl-5-hexenyl)-1H-benzoimidazole-5-carboxylate as the first elution component and 0.21 g (yield: 33%) of 6,6-difluoro-5-methyl-5-hexenyl 3-(6,6-difluoro-5-methyl-5-hexenyl)-3H-benzoimidazole-5-carboxylate as the second elution component.

A compound (35): $^1$H-NMR ($CDCl_3$, TMS) δ ppm: 1.39-1.64 (1H, m), 1.74-1.94 (4H, m), 1.99-2.09 (4H, m), 4.22 (2H, t), 4.37 (2H, t), 7.42 (1H, d), 7.97 (1H, s), 8.05 (1H, d), 8.54(1H, s)

A compound (36): $^1$H-NMR ($CDCl_3$, TMS) δ ppm: 1.43-1.64 (1H, m), 1.76-1.96 (4H, m), 2.00-2.09 (4H, m), 4.25 (2H, t), 4.38 (2H, t), 7.82 (1H, d), 7.97-8.01 (2H, m), 8.16 (1H, s)

Production Example 21

Production of Compound (57) by the Production Method 6

To 5 ml of pyridine was dissolved 0.62 g (2.3 mmol) of 6,6-difluoro-5-methyl-5-hexenyl 6-aminonicotinate, followed by the addition of 0.48 g (2.5 mmol) of toluene-4-sulfonylchloride under ice-cooling, stirring for 10 minutes and then stirring at room temperature for 15 hours. The reaction liquid was then poured in 5% hydrochloric acid and extracted with ethyl acetate. The organic layer was washed with water and a saturated saline solution in this order, followed by drying over anhydrous magnesium sulfate and concentration under reduced pressure. The residue was purified with silica gel column chromatography (ethyl acetate:hexane=1:2) to obtain 0.88 g (yield: 90%) of 6,6-difluoro-5-methyl-5-hexenyl 6-(toluene-4-sulfonylamino) nicotinate.

$^1$H-NMR ($CDCl_3$, TMS) δ ppm: 1.45-1.55 (5H, m), 1.67-1.76 (2H, m), 1.97-2.03 (2H, m), 2.40 (3H, s), 4.30 (2H, t), 7.27 (2H, d), 7.39 (1H, d), 7.80 (2H, d), 8.19 (1H, d), 8.93 (1H, s), 11.60 (1H, br.s)

Production Example 22

Production of compound (58) by the production method 7

To 5 ml of N,N-dimethylformamide were dissolved 0.30 g (0.7 mmol) of 6,6-difluoro-5-methyl-5-hexenyl 6-(toluene-4-sulfonylamino)nicotinate and 0.15 g (1.1 mmol) of methyl iodide, followed by the addition of 0.20 g (1.4 mmol) of potassium carbonate at room temperature and stirring at the same temperature for 1 hour. The reaction liquid was then poured in water and extracted with ethyl acetate. The organic layer was washed with water and a saturated saline solution in this order, followed by drying over anhydrous magnesium sulfate and concentration under reduced pressure. The residue was purified with silica gel column chromatography (ethyl acetate:hexane=1:4) to obtain 0.15 g (yield: 48%) of 6,6-difluoro-5-methyl-5-hexenyl 6-[N-methyl-N-(toluene-4-sulfonyl)amino] nicotinate.

$^1$H-NMR ($CDCl_3$, TMS) δ ppm: 1.49-1.58 (5H, m), 1.70-1.80 (2H, m), 2.01-2.07 (2H, m), 2.39 (3H, s), 3.37 (3H, s), 4.33 (2H, t), 7.24 (2H, d), 7.53 (2H, d), 7.80 (1H, d), 8.23 (1H, dd), 8.88 (1H, d)

Production Example 23

Production of Compound (61) by the Production Method 1 and the Production Method 7

To 10 ml of N,N-dimethylformamide were dissolved 0.80 g (4.0 mmol) of 4,4-difluoro-3-methyl-3-butenyl methanesulfonate and 0.72 g (5.2 mmol) of 6-hydroxynicotinic acid, followed by the addition of 1.3 g (15 mmol) of sodium hydrogencarbonate and stirring at 130° C. for 4 hours. The reaction liquid was then poured in water and extracted with ethyl acetate. The organic layer was washed with water and a saturated saline solution in this order, followed by drying over anhydrous magnesium sulfate and concentration under reduced pressure. The residue was purified with silica gel column chromatography (ethyl acetate:hexane=1:5) to obtain 0.19 g (yield: 27%) of 4,4-difluoro-3-methyl-3-butenyl 6-(4,4-difluoro-3-methyl-3-butenyloxy)nicotinate.

$^1$H-NMR ($CDCl_3$, TMS) δ ppm: 1.64-1.67 (6H, m), 2.40-2.48 (4H, m), 4.37 (2H, t), 4.44 (2H, t), 6.75 (1H, d), 8.13 (1H, dd), 8.80 (1H, d)

Production Example 24

Production of Compound (39) by the Production Method 8

A mixture consisting of 1.5 g (13 mmol) of 1H-imidazole-4-carboxylic acid and 5 ml of thionyl chloride and three drops of N,N-dimethylformamide and 10 ml of toluene was stirred under heating and refluxing for 30 hours. After the reaction, excess thionyl chloride and the solvent were removed under reduced pressure to obtain crystal of diimidazo[1, 5-a, 1', 5'-d] pyrazine-5,10-dione. In a separate vessel, 0.10 g (2.5 mmol) of sodium hydride was added at room temperature to a mixture consisting of 0.30 g (2.0 mmol) of 6,6-difluoro-5-methyl-5-hexenol, 0.18 g (1.0 mmol) of diimidazo[1,5-a, 1', 5'-d]pyrazine-5,10-dione and 5 ml of tetrahydrofuran, followed by stirring at the same temperature for 2 hours, the addition of 0.40 g (2.8 mmol) of methyl iodide and further stirring for 2 hours. To the reaction liquid was added 20 ml of ethyl acetate to filter off solid and the filtrate was concentrated under reduced pressure. The residue was purified with silica gel column chromatography (ethyl acetate methanol=10:1) to obtain 0.15 g (yield: 30%) of 6,6-difluoro-5-methyl-5-hexenyl 1-methyl-1H-imidazole-4-carboxylate.

$^1$H-NMR ($CDCl_3$, TMS) δ ppm: 1.47-1.56 (5H, m), 1.70-1.79 (2H, m), 1.98-2.04 (2H, m), 3.75 (3H, s), 4.31 (2H, t), 7.51 (2H, s), 7.56 (1H, s)

Production Example 25

Production of Compound (105) by the Production Method 1

To 50 ml of N,N-dimethylformamide were dissolved 6.6 g (33 mmol) of 4,4-difluoro-3-methyl-3-butenyl methanesulfonate and 7.6 g (36 mmol) of 2-butoxy-4-methylpyrimidine-5-carboxylic acid, followed by the addition of 3.6 g (43 mmol) of sodium hydrogencarbonate and stirring at 100° C. for 2 hours. The reaction liquid was then poured in water and extracted with ethyl acetate. The organic layer was washed with water and a saturated saline solution in this order, followed by drying over anhydrous magnesium sulfate and concentration under reduced pressure. The residue was purified with silica gel column chromatography (ethyl acetate:hexane=1:9) to obtain 3.3 g (yield: 32%) of 4,4-difluoro-3-methyl-3-butenyl 2-butoxy-4-methylpyrimidine-5-carboxylate.

$^1$H-NMR ($CDCl_3$, TMS) δ ppm: 0.97 (3H, t), 1.44-1.57 (2H, m), 1.66 (3H, t), 1.76-1.85 (2H, m), 2.41-2.47 (2H, m), 2.76 (3H, s), 4.37 (2H, t), 4.42 (2H, t), 8.96 (1H, s)

Production Example 26

Production of Compound (77) by the Production Method 1

To 5 ml of N,N-dimethylformamide were dissolved 0.39 g (2.0 mmol) of 6-butoxynicotinic acid, synthesized by a method in accordance with one used in Intermediate Production Example 1, and 0.40 g (2.0 mmol) of 4,4-difluoro-3-methyl-3-butenyl methanesulfonate, followed by the addition of 0.34 g (4.0 mmol) of sodium hydrogencarbonate and stirring at 100° C. for 3 hours. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (diisopropyl ether:hexane=1:7) to obtain 0.45 g (yield: 75%) of 4,4-difluoro-3-methyl-3-butenyl 6-butoxynicotinate.

$^1$H-NMR ($CDCl_3$, TMS) δ ppm: 0.98 (3H, t), 1.42-1.54 (2H, m), 1.66 (3H, t), 1.73-1.82 (2H, m), 2.40-2.46 (2H, m), 4.36 (4H, t), 6.74 (1H, dd), 8.12 (1H, dd), 8.81 (1H, dd)

Production Example 27

Production of Compound (81) by the Production Method 1

To 5 ml of N,N-dimethylformamide were dissolved 0.42 g (2.1 mmol) of 4,4-difluoro-3-methyl-3-butenyl methanesulfonate and 0.42 g (2.0 mmol) of 6-cyclopentyloxynicotinic acid, followed by the addition of 0.35 g (4.2 mmol) of sodium hydrogencarbonate and stirring at 100° C. for 3 hours. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (diisopropyl ether: hexane=1:7) to obtain 0.44 g (yield: 70%) of 4,4-difluoro-3-methyl-3-butenyl 6-cyclopentyloxynicotinate.

$^1$H-NMR ($CDCl_3$, TMS) δ ppm: 1.60-2.05 (1H, m), 2.40-2.45 (2H, m), 4.36 (4H, t), 5.45-5.51 (1H, m), 6.70 (1H, d), 8.10 (1H, dd), 8.82 (1H, d)

Production Example 28

Production of Compound (93) by the Production Method 1

To 5 ml of N,N-dimethylformamide were dissolved 0.34 g (1.6 mmol) of 4-methyl-2-phenylpyrimidine-5-carboxylic acid, synthesized in accordance with a method described in "J. Chem. Soc.", page 2183 (1923), and 0.30 g (1.5 mmol) of 4,4-difluoro-3-methyl-3-butenyl methanesulfonate, followed by the addition of 0.27 g (3.2 mmol) of sodium hydrogencarbonate and stirring at 100° C. for 3 hours. The reaction liquid was then poured in water and extracted with diethtyl ether. The organic layer was washed with water and a saturated saline solution in this order, followed by drying over anhydrous magnesium sulfate and concentration under reduced pressure. The residue was purified with silica gel column chromatography (diisopropyl ether:hexane=1:4) to obtain 0.35 g (yield: 73%) of 4,4-difluoro-3-methyl-3-butenyl 4-methyl-2-phenylpyrimidine-5-carboxylate.

$^1$H-NMR ($CDCl_3$, TMS) δ ppm: 1.68 (3H, t), 2.45-2.50 (2H, m), 2.89 (3H, s), 4.42(2H, t), 7.47-7.55 (3H, m), 8.50-8.54 (2H, m), 9.20 (1H, s)

Production Example 29

Production of Compound (218) by the Production Method 1

To 10 ml of N,N-dimethylformamide were dissolved 1.00 g (5.0 mmol) of 4,4-difluoro-3-methyl-3-butenyl methanesulfonate and 1.30 g (5.5 mmol) of 2-benzyl-4-methylpyrimidine-5-carboxylic acid, followed by the addition of 0.50 g (6.0 mmol) of sodium hydrogencarbonate and stirring at 100° C. for 3 hours. The reaction liquid was then poured in water and extracted with diethyl ether. The organic layer was washed with water and a saturated saline solution in this order, followed by drying over an hydrous magnesium sulfate, the addition of "Florisil" and filtering. The solution was concentrated under reduced pressure to obtain 1.30 g (yield: 78%) of 4,4-difluoro-3-methyl-3-butenyl 2-benzyl-4-methylpyrimidine-5-carboxylate.

$^1$H-NMR ($CDCl_3$, TMS) δ ppm: 1.64 (3H, t), 2.41-2.45 (2H, m), 2.80 (3H, s), 4.29 (2H, s), 4.38 (2H, t), 7.24 (1H, t), 7.30 (2H, t), 7.37 (2H, d), 9.05 (1H, s)

Production Example 30

Production of Compound (110) by the Production Method 1

To 40 ml of N,N-dimethylformamide were dissolved 4.00 g (20 mmol) of 4,4-difluoro-3-methyl-3-butenyl methanesulfonate and 4.00 g (22 mmol) of 4-methyl-2-(methylthio) pyrimidine-5-carboxylic acid, followed by the addition of 3.70 g (44 mmol) of sodium hydrogencarbonate and stirring at 100° C. for 3 hours. The reaction liquid was then poured in water and extracted with diethyl ether. The organic layer was washed with water and a saturated saline solution in this order, followed by drying over anhydrous magnesium sulfate, the addition of "Florisil" and filtering. The solution was concentrated under reduced pressure to obtain 5.30 g (yield: 92%) of 4,4-difluoro-3-methyl-3-butenyl 4-methyl-2-(methylthio)-pyrimidine-5-carboxylate.

$^1$H-NMR ($CDCl_3$, TMS) δ ppm: 1.66 (3H, t), 2.42-2.46 (2H, m), 2.61 (3H, s), 2.76 (3H, s), 4.38 (2H, t), 8.92 (1H, s)

Production Example 31

Production of Compound (111) by the Production Method 9

To 20 ml of chloroform was dissolved 1.10 g (3.8 mmol) of 4,4-difluoro-3-methyl-3-butenyl 4-methyl-2-(methylthio) pyrimidine-5-carboxylate, followed by the addition, in three portions, of 2.00 g (8.1 mmol) of 70% m-chloroperbenzoic acid under ice-cooling and stirring for 1 hour after warming to room temperature. An aqueous solution of sodium hydrogensulfite was added under ice-cooling and the mixture was filtered to fractionate an organic layer. The organic layer was washed with a saturated sodium hydrogencarbonate solution and water in this order, followed by drying over anhydrous magnesium sulfate, the addition of "Florisil" and filtering. The solution was concentrated at 40° C. under reduced pressure to obtain 1.13 g (yield: 92%) of 4,4-difluoro-3-methyl-3-butenyl 2-methanesulfonyl-4-methylpyrimidine-5-carboxylate.

$^1$H-NMR ($CDCl_3$, TMS) δ ppm: 1.67 (3H, t), 2.46-2.50 (2H, m), 2.95 (3H, s), 3.39 (3H, s), 4.47 (2H, t), 9.25 (1H, s)

Production Example 32

Production of Compound (214) by the Production Method 10

To 3 ml of N,N-dimethylformamide were dissolved 0.50 g (1.6 mmol) of 4,4-difluoro-3-methyl-3-butenyl 2-methanesulfonyl-4-methylpyrimidine-5-carboxylate, followed by the addition of 0.28 g (3.2 mmol) of N-butyl-N-methylamine and stirring at room temperature for 30 minutes. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (ethyl acetate ether:hexane=1:7) to obtain 0.41 g (yield: 80%) of 4,4-difluoro-3-methyl-3-butenyl 2-(N-butyl-N-methylamino)-4-methylpyrimidine-5-carboxylate.

$^1$H-NMR ($CDCl_3$, TMS) δ ppm: 0.95 (3H, t), 1.28-1.40 (2H, m), 1.55-1.66 (5H, m), 2.38-2.42 (2H, m), 2.63 (3H, s), 3.20 (3H, br.s), 3.69 (2H, br.t), 4.30 (2H, t), 8.79 (1H, s)

Production Example 33

Production of Compound (117) by the Production Method 10

To 5 ml of tetrahydrofuran were dissolved 0.56 g (1.8 mmol) of 4,4-difluoro-3-methyl-3-butenyl 2-methanesulfonyl-4-methylpyrimidine-5-carboxylate and 0.21 g (1.9 mmol) of thiophenol, followed by the addition of 0.30 g (2.8 mmol) of sodium carbonate and stirring at room temperature for 1 hour. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (ethyl acetate:hexane=1:8) to obtain 0.54 g (yield: 88%) of 4,4-difluoro-3-methyl-3-butenyl 4-methyl-2-(phenylthio)pyrimidine-5-carboxylate.

$^1$H-NMR ($CDCl_3$, TMS) δ ppm: 1.63 (3H, t), 2.38-2.44 (2H, m), 2.71 (3H, s), 4.35 (2H, t), 7.43-7.48 (3H, m), 7.60-7.64 (2H, m), 8.86 (1H, s)

Production Example 34

Production of Compound (254) by the Production Method 10

To 1.02 g (9.4 mmol) of 4-chlorobutanol was dissolved 1.00 g (3.1 mmol) of 4,4-difluoro-3-methyl-3-butenyl 2-methanesulfonyl-4-methylpyrimidine-5-carboxylate, followed by the addition of 0.38 g (3.8 mmol) of triethylamine under ice-cooling and stirring at room temperature for 14 hours. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (ethyl acetate:hexane=1:9) to obtain 0.30 g (yield: 27%) of 4,4-difluoro-3-methyl-3-butenyl 2-(4-chlorobutoxy)-4-methylpyrimidine-5-carboxylate.

$^1$H-NMR ($CDCl_3$, TMS) δ ppm: 1.66 (3H, t), 1.97-2.01 (4H, m), 2.41-2.47 (2H, m), 2.76 (3H, s), 3.59-3.64 (2H, m), 4.37 (2H, t), 4.45-4.49 (2H, m), 8.96 (1H, s)

Production Example 35

Production of Compound (63) by the Production Method 1

To 25 ml of N,N-dimethylformamide were dissolved 2.60 g (13 mmol) of 4,4-difluoro-3-methyl-3-butenyl methanesulfonate and 2.19 g (10 mmol) of 4-methyl-2-phenylthiazole-5-carboxylic acid, followed by the addition of 1.68 g (20 mmol) of sodium hydrogencarbonate and stirring at 100° C. for 3 hours. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (ethyl acetate ether: hexane=1:9) to obtain 3.03 g (yield: 94%) of 4,4-difluoro-3-methyl-3-butenyl 4-methyl-2-phenylthiazole-5-carboxylate.

$^1$H-NMR ($CDCl_3$, TMS) δ ppm: 1.67 (3H, t), 2.40-2.46 (2H, m), 2.78 (3H, s), 4.36 (2H, t), 7.44-7.49 (3H, m), 7.95-7.99 (2H, m), Production Example 36

Production of Compound (169) by the Production Method 1

To 7 ml of N,N-dimethylformamide were dissolved 0.50 g (2.5 mmol) of 4,4-difluoro-3-methyl-3-butenyl methanesulfonate and 0.56 g (2.5 mmol) of 2-cyclohexyl-4-methylthiazole-5-carboxylic acid, followed by the addition of 0.42 g (5.0 mmol) of sodium hydrogencarbonate and stirring at 100° C. for 3 hours. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (ethyl acetate:hexane=1:9) to obtain 0.64 g (yield: 78%) of 4,4-difluoro-3-methyl-3-butenyl 2-cyclohexyl-4-methylthiazole-5-carboxylate.

$^1$H-NMR ($CDCl_3$, TMS) δ ppm: 1.21-1.52 (5H, m), 1.65 (3H, t), 1.72-1.88 (3H, m), 2.09-2.15 (2H, m), 2.37-2.42 (2H, m), 2.69 (3H, s), 2.88-2.98 (1H, m), 4.31 (2H, t)

Production Example 37

Production of Compound (172) by the Production Method 1

To 15 ml of N,N-dimethylformamide were dissolved 1.00 g (5.0 mmol) 4,4-difluoro-3-methyl-3-butenyl methanesulfonate and 1.17 g (5.0 mmol) of 4-methyl-2-(N-phenylamino)thiazole-5-carboxylic acid, followed by the addition of 0.84 g (10 mmol) of sodium hydrogencarbonate and stirring at 80° C. for 5 hours. The reaction liquid was then poured in water and extracted with ethyl acetate. The organic layer was washed with water and a saturated saline solution in this order, followed by drying over anhydrous magnesium sulfate and concentration under reduced pressure. The residue was purified with silica gel column chromatography (ethyl acetate:hexane=1:3) to obtain 0.90 g (yield: 53%) of 4,4-difluoro-3-methyl-3-butenyl 4-methyl-2-(N-phenylamino) thiazole-5-carboxylate.

$^1$H-NMR ($CDCl_3$, TMS) δ ppm: 1.64 (3H, t), 2.35-2.40 (2H, m), 2.57 (3H, s), 4.28 (2H, t), 7.16 (1H, t), 7.32 (2H, d), 7.40 (2H, t), 7.93 (1H, br.s)

Production Example 38

Production of Compound (173) by the Production Method 7

To 4 ml of N,N-dimethylformamide were dissolved 0.68 g (2.0 mmol) of 4,4-difluoro-3-methyl-3-butenyl 4-methyl-2-(N-phenylamino)thiazole-5-carboxylate and 0.57 g (4.0 mmol) of methyl iodide, followed by the addition of 0.10 g (2.5 mmol) of 60% sodium hydride and stirring at room temperature for 3 hours. The reaction liquid was then poured in water and extracted with ethyl acetate. The organic layer was washed with water and a saturated saline solution in this order, followed by drying over anhydrous magnesium sulfate and concentration under reduced pressure. The residue was purified with silica gel column chromatography (ethyl acetate:hexane=1:4) to obtain 0.66 g (yield: 93%) of 4,4-difluoro-3-methyl-3-butenyl 4-methyl-2-(N-methyl-N-phenylamino) thiazole-5-carboxylate.

$^1$H-NMR ($CDCl_3$, TMS) δ ppm: 1.59 (3H, t), 2.29-2.35 (2H, m), 2.58 (3H, s), 3.55 (3H, s), 4.21 (2H, t), 7.30-7.48 (5H, m)

Production Example 39

Production of Compound (196) by the Production Method 1

To 5 ml of N,N-dimethylformamide were dissolved 0.57 g (2.8 mmol) of 3-methyl-1-phenyl-1H-pyrazole-4-carboxylic acid, obtained in accordance with a method described in J. Chem. Soc., page 2736 (1961), and 0.58 g (2.9 mmol) of 4,4-difluoro-3-methyl-3-butenyl methanesulfonate, followed by the addition of 0.48 g (5.7 mmol) of sodium hydrogencarbonate and stirring at 100° C. for 3 hours. The reaction liquid was then poured in water and extracted with diethyl ether. The organic layer was washed with water and a saturated saline solution in this order, followed by drying over anhydrous magnesium sulfate and concentration under reduced pressure. The residue was purified with silica gel column chromatography (ethyl acetate:hexane=1:6) to obtain 0.66 g (yield: 76%) of 4,4-difluoro-3-methyl-3-butenyl 3-methyl-1-phenyl-1H-pyrazole-4-carboxylate.

$^1$H-NMR ($CDCl_3$, TMS) δ ppm: 1.66 (3H, t), 2.39-2.45 (2H, m), 2.55 (3H, s), 4.33 (2H, t), 7.33 (1H, t), 7.47 (2H, t), 7.67 (2H, d), 8.32 (1H, s)

Reference Example 1

Production of 6,6-difluoro-5-methyl-5-hexenethiol

Reaction was carried out under nitrogen atmosphere. To 20 ml of tetrahydrofuran, 0.59 g (16 mmol) of lithium aluminium hydride was suspended, followed by the dropwise addition of 2.60 g (10 mmol) of 6,6-difluoro-5-methyl-5-hexenyl N,N-dimethyldithiocarbamate dissolved in 20 ml of tetrahydrofuran at room temperature and then stirring for 3 hours under refluxing. The reaction liquid was ice-cooled and quenched by the addition of water, followed by the addition of dilute hydrochloric acid to make acidic, and extracting with diethyl ether. The organic layer was washed with water, followed by drying over anhydrous magnesium sulfate and concentrating under reduced pressure to about 10 ml. The pressure was increased to normal level by nitrogen to quantitatively obtain 6,6-difluoro-5-methyl-5-hexenethiol to be used in the next reaction.

Reference Example 2

Production of 2-benzyl-4-methylpyrimidine-5-carboxylic acid (1) To 100 ml of N,N-dimethylformamide, 17.1 g (100 mmol) of 2-phenylacetoamidine hydrochloric acid salt, synthesized in accordance with a method described in "Tetrahedron", page 887 (1984), 18.6 g (100 mmol) of ethyl 2-acetyl-3-ethoxyacrylate and 9.0 g (110 mmol) of sodium acetate were suspended, followed by stirring at 100° C. for 3 hours. The reaction liquid was cooled and then poured into ice water, and extracting with diethyl ether. The organic layer was washed with water and a saturated saline solution in this order, followed by drying over anhydrous magnesium sulfate and concentrating under reduced pressure to obtain 22.8 g (yield: 89%) of ethyl 2-benzyl-4-methylpyrimidine-5-carboxylate.

$^1$H-NMR ($CDCl_3$, TMS) δ ppm: 1.39 (3H, t), 2.80 (3H, s), 4.28 (2H, s), 4.38 (2H, q), 7.22 (1H, t), 7.30 (2H, t), 7.36 (2H, d), 9.07 (1H, s)

(2) To 40 ml of ethanol, 10.0 g (39 mmol) of ethyl 2-benzyl-4-methylpyrimidine-5-carboxylate was dissolved, followed by adding 12.5 g (78 mmol) of 25% sodium hydroxide aqueous solution and stirring at room temperature for 15 hours. Ethanol was then removed, and the residue was dissolved in 100 ml of water, and 10% hydrochloric acid was added to make acidic. Crystal precipitated was filtered, washed with water and dried to obtain 8.10 g (yield: 91%) of 2-benzyl-4-methylpyrimidine-5-carboxylic acid.

$^1$H-NMR ($CDCl_3$, TMS) δ ppm: 2.87 (3H, s), 4.33 (2H, s), 7.25 (1H, t), 7.30 (2H, t), 7.38 (2H, d), 9.22 (1H, s)

Reference Example 3

Production of 2-cyclohexyl-4-methylthiazole-5-carboxylic acid (1) To 90 ml of tetrahydrofuran, 11.1 g (87 mmol) of cyclohexanecarboxamide and 17.6 g (43.5 mmol) of Lawesson's reagent were suspended, followed by heating under refluxing for 3 hours. The reaction liquid was cooled to room temperature, followed by adding 14.4 g (87 mmol) of ethyl 2-chloro-3-oxobutanate and heating under refluxing for further 3 hours. The reaction liquid was poured into ice water and extracted with diethyl ether. The organic layer was washed with water, dilute hydrochloric acid, an aqueous solution of sodium carbonate and saturated saline solution in this order, followed by drying over anhydrous magnesium sulfate and concentrating under reduced pressure. The residue was purified with silica gel column chromatography (ethyl acetate:hexane=1:5) to obtain 20.3 g (yield: 92%) of ethyl 2-cyclohexyl-4-methylthiazole-5-carboxylate.

$^1$H-NMR ($CDCl_3$, TMS) δ ppm: 1.24-1.56 (8H, m), 1.65 (3H, t), 1.70-1.87 (3H, m), 2.09-2.15 (2H, m), 2.70 (3H, s), 2.90-3.00 (1H, m), 4.32 (2H, q)

(2) To 20 ml of methanol, 17.3 g (68 mmol) of ethyl 2-cyclohexyl-4-methylthiazole-5-carboxylate was dissolved, followed by adding 24 g (150 mmol) of 25% sodium hydroxide aqueous solution and stirring at room temperature for 15 hours. Methanol was removed, and the residue was then dissolved in 200 ml of water, and 10% hydrochloric acid was added to make acidic. Crystal precipitated was filtered, washed with water and dried to obtain 12.8 g (yield: 83%) of 2-cyclohexyl-4-methylthiazole-5-carboxylic acid.

$^1$H-NMR ($CDCl_3$, TMS) δ ppm: 1.22-1.57 (5H, m), 1.73-1.88 (3H, m), 2.12-2.16 (2H, m), 2.73 (3H, s), 2.93-3.03 (1H, m)

Similarly, thiazolcarboxylic acid derivatives were synthesized as raw materials for compounds (67), (130), (133), (134) and (142) to (168).

Reference Example 4

Production of 4-methyl-2-(N-phenylamino) thiazole-5-carboxylic acid (1) To 70 ml of ethanol, 10.7 g (70 mmol) of phenylthiourea and 11.6 g (70 mmol) of ethyl 2-chloro-3-oxobutanate were dissolved, followed by heating under refluxing for 8 hours. The reaction liquid was concentrated and dissolved in ethyl acetate and the organic layer was washed with an aqueous solution of sodium carbonate, water and a saturated saline solution in this order, followed by drying over anhydrous magnesium sulfate and concentrating under reduced pressure. Solid obtained was washed with diisopropyl ether to obtain 16.8 g (yield: 91%) of ethyl 4-methyl-2-(N-phenylamino)thiazole-5-carboxylate.

(2) To 50 ml of ethanol, 12.8 g (49 mmol) of ethyl-4-methyl-2-(N-phenylamino)thiazole-5-carboxylate was dissolved, followed by adding 24 g (150 mmol) of 25% sodium hydroxide aqueous solution, and stirring at 80° C. for 15 hours. The reaction liquid was poured into ice water, and acetic acid was added to make acidic. Crystal precipitated was filtered, washed with water and a mixed solvent of hexane/ethyl acetate and dried to obtain 5.50 g (yield: 48%) of 4-methyl-2-(N-phenylamino)thiazole-5-carboxylic acid.

Similarly, thiazolcarboxylic acid derivatives were synthesized as raw materials for compounds (178), (179), (183) and (188).

Some specific examples of compounds of the present invention, shown by the general formula [1] are shown below with compound numbers and physical properties (refractive index: $n_d^{20}$; melting point: m.p.) thereof.

(1) 6,6-di-fluoro-5-methyl-5-hexenyl 6-chloronicotinate ($n_D^{20}$=1.4967)
(2) 6,6-difluoro-5-methyl-5-hexenyl 3-methylthiophene-2-carboxylate ($n_D^{20}$=1.4931)
(3) 6,6-difluoro-5-methyl-5-hexenyl benzo[b]thiophene-2-carboxylate ($n_D^{20}$=1.5468)
(4) 6,6-difluoro-5-methyl-5-hexenyl 4,6-dimethoxy-pyrimidine-2-carboxylate ($n_D^{20}$=1.4788)
(5) 6,6-difluoro-5-methyl-5-hexenyl 1H-pyrrole-2-carboxylate ($n_D^{20}$=1.4871)
(6) 6,6-difluoro-5-methyl-5-hexenyl 1H-indole-2-carboxylate (m.p.=85 to 86° C.)
(7) 6,6-difluoro-5-methyl-5-hexenyl benzo[b]furan-2-carboxylate ($n_D^{20}$=1.5203)
(8) 6,6-difluoro-5-methyl-5-hexenyl quinoline-3-carboxylate ($n_D^{20}$=1.5399)
(9) 6,6-difluoro-5-methyl-5-hexenyl furan-2-carboxylate ($n_D^{20}$=1.4596)
(10) 8,8-difluoro-7-methyl-7-octenyl benzo[b]thiophene-2-carboxylate ($n_D^{20}$=1.5388)
(11) 6,6-difluoro-5-methyl-5-hexenyl 4-phenyl[1,2,3]-thiadiazole-5-carboxylate ($n_D^{20}$=10.5421)
(12) 6,6-difluoro-5-methyl-5-hexenyl 5-methyl-3-phenyl-isoxazole-4-carboxylate ($n_D^{20}$=1.5083)
(13) 6,6-difluoro-5-methyl-5-hexenyl 1H-indole-3-carboxylate (m.p.=68 to 69° C.)
(14) 6,6-difluoro-5-methyl-5-hexenyl 1-methyl-1H-indole-3-carboxylate ($n_D^{20}$=1.5355)
(15) 6,6-difluoro-5-methyl-5-hexenyl 1H-indole-5-carboxylate ($n_D^{20}$2=1.5405)
(16) 6,6-difluoro-5-methyl-5-hexenyl 1-methyl-1H-indrole-5-carboxylate ($n_D^{20}$=1.5391)
(17) 6,6-difluoro-5-methyl-5-hexenyl pyridine-2-carboxylate ($n_D^{20}$=1.4807)
(18) 4,4-difluoro-3-methyl-3-butenyl benzo[b]thiophene-2-carboxylate (m.p.=52 to 53° C.)
(19) 6,6-difluoro-5-methyl-5-hexenyl nicotinate ($n_D^{20}$=1.4791)
(20) 6,6-difluoro-5-methyl-5-hexenyl isonicotinate ($n_D^{20}$=1.4740)
(21) 6,6-difluoro-5-methyl-5-hexenyl benzothiazole-2-carboxylate ($n_D^{20}$=1.5476)
(22) 6,6-difluoro-5-methyl-5-hexenyl [1,2,5]thiadiazole-3-carboxylate ($n_D^{20}$=1.4790)
(23) 6,6-difluoro-5-methyl-5-hexenyl 4,6-dimethoxy [1,3,5]-triazine-2-carboxylate ($n_D^{20}$=1.4696)
(24) 6,6-difluoro-5-methyl-5-hexenyl 1-methyl-1H-indole-2-carboxylate ($n_D^{20}$=1.5447)
(25) 6,6-difluoro-5-methyl-5-hexenyl 1-ethyl-1H-indole-2-carboxylate ($n_D^{20}$=1.5400)
(26) 6,6-difluoro-5-methyl-5-hexenyl 4-chloro-5-ethyl-2-methyl-2H-pyrazole-3-carboxylate ($n_D^{20}$=1.4796)
(27) 6,6-difluoro-5-methyl-5-hexenyl isoquinoline-3-carboxylate ($n_D^{20}$=1.5438)
(28) 6,6-difluoro-5-methyl-5-hexenyl pyrazine-2-carboxylate ($n_D^{20}$=1.4789)
(29) 6,6-difluoro-5-methyl-5-hexenyl 4-methyl-2-phenyl-thiazole-5-carboxylate ($n_D^{20}$=1.5583)
(30) 6,6-difluoro-5-methyl-5-hexenyl 1H-benzotriazole-5-carboxylate ($n_D^{20}$=1.5257)
(31) 6,6-difluoro-5-methyl-5-hexenyl 2-(6,6-difluoro-5-methyl-5-hexenyl)-2H-benzotriazole-5-carboxylate ($n_D^{20}$=1.5020)
(32) 6,6-difluoro-5-methyl-5-hexenyl quinoxaline-2-carboxylate ($n_D^{20}$=1.5430)
(33) 6,6-difluoro-5-methyl-5-hexenyl 1H-indazole-3-carboxylate ($n_D^{20}$=1.5351)
(34) 6,6-difluoro-5-methyl-5-hexenyl 5,7-dimethyl [1,2,4]-triazolo[1,5-a]pyrimidine-2-carboxylate (m.p.=123 to 126° C.)
(35) 6,6-difluoro-5-methyl-5-hexenyl 1-(6,6-difluoro-5-methyl-5-hexenyl)-1H-benzoimidazole-5-carboxylate ($n_D^{20}$=1.5071)
(36) 6,6-difluoro-5-methyl-5-hexenyl 3-(6,6-difluoro-5-methyl-5-hexenyl)-3H-benzoimidazole-5-carboxylate ($n_D^{20}$=1.5042)
(37) 6,6-difluoro-5-methyl-5-hexenyl cinnoline-4-carboxylate ($n_D^{20}$=1.5393)
(38) 6,6-difluoro-5-methyl-5-hexenyl 1-methyl-1H-pyrrole-2-carboxylate ($n_D^{20}$=1.4807)
(39) 6,6-difluoro-5-methyl-5-hexenyl 1-methyl-1H-imidazole-4-carboxylate ($n_D^{20}$=not measurable)
(40) 6,6-difluoro-5-methyl-5-hexenyl 1-acetylpiperidine-4-carboxylate ($n_D^{20}$=1.4650)
(41) 6,6-difluoro-5-methyl-5-hexenyl tetrahydrofuran-3-carboxylate ($n_D^{20}$=1.4357)
(42) 6,6-difluoro-5-methyl-5-hexenyl benzo[1,2,5]-thiadiazole-5-carboxylate ($n_D^{20}$=1.5443)
(43) 6,6-difluoro-5-methyl-5-hexenyl benzoxazole-5-carboxylate (m.p.=35 to 37° C.)
(44) 6,6-difluoro-5-methyl-5-hexenyl benzo[d]isoxazole-3-carboxylate ($n_D^{20}$=1.5036)
(45) 6,6-difluoro-5-methyl-5-hexenyl benzo[d]isothiazole-3-carboxylate ($n_D^{20}$=1.5421)
(46) 6,6-difluoro-5-methyl-5-hexenyl 5,7-dimethoxypyrazolo-[1,5-a]pyrimidine-3-carboxylate
(47) 6,6-difluoro-5-methyl-5-hexenyl 5-methyl-1-phenyl-1H-[1,2,4]triazole-3-carboxylate ($n_D^{20}$=1.5178)
(48) 6,6-difluoro-5-methyl-5-hexenyl 3,6-dichloropyridazine-4-carboxylate ($n_D^{20}$=1.5048)
(49) 6,6-difluoro-5-methyl-5-hexenyl 3,4-dichloroisothiazole-5-carboxylate ($n_D^{20}$=not measurable)
$^1$H-NMR ($CDCl_3$, TMS) δ ppm: 1.49-1.59 (5H, m), 1.71-1.81 (2H, m), 2.01-2.07 (2H, m), 4.38 (2H, t)
(50) 6,6-difluoro-5-methyl-5-hexenyl 5-ethoxy-2-phenyl-oxazole-4-carboxylate ($n_D^{20}$=1.5230)
(51) 6,6-difluoro-5-methyl-5-hexenyl 4-chloro-7-methyl [1,8]-naphthyridine-3-carboxylate
(52) S-(6,6-difluoro-5-methyl-5-hexenyl) 6-chlorothio-nicotinate ($n_D^{20}$=1.5327)
(53) S-(6,6-difluoro-5-methyl-5-hexenyl) benzo[b] thiophene-2-thiocarboxylate ($n_D^{20}$=1.5995)
(54) O-(4,4-difluoro-3-methyl-3-butenyl) benzo[b] thiophene-2-thiocarboxylate
(55) O-(6,6-difluoro-5-methyl-5-hexenyl) benzo[b] thiophene-2-thiocarboxylate ($n_D^{20}$=1.6144)
(56) 6,6-difluoro-5-methyl-5-hexenyl 6-aminonicotinate (m.p.=78 to 80° C.)
(57) 6,6-difluoro-5-methyl-5-hexenyl 6-(toluene-4-sulfonyl-amino)nicotinate (m.p.=107 to 108° C.)

(58) 6,6-difluoro-5-methyl-5-hexenyl 6-[N-methyl-N-(toluene-4-sulfonyl)amino]nicotinate ($n_D^{20}$=1.5420)

(59) 6,6-difluoro-5-methyl-5-hexenyl 4-hydroxy-6-(2-tolyloxy)pyrimidine-2-carboxylate ($n_D^{20}$=1.5155)

(60) 6,6-difluoro-5-methyl-5-hexenyl 4-(6,6-difluoro-5-methyl-5-hexenyloxy)-6-(2-tolyloxy)pyrimidine-2-carboxylate ($n_D^{20}$=1.4985)

(61) 4,4-difluoro-3-methyl-3-butenyl 6-(4,4-difluoro-3-methyl-3-butenyloxy)nicotinate ($n_D^{20}$=1.4757)

(62) 6,6-difluoro-5-methyl-5-hexenyl 5-methyl-1-phenyl-1H-pyrazole-3-carboxylate ($n_D^{20}$=1.5211)

(63) 4,4-difluoro-3-methyl-3-butenyl 4-methyl-2-phenylthiazole-5-carboxylate ($n_D^{20}$=1.5688)

(64) 4,4-difluoro-3-methyl-3-butenyl benzo[1,2, 5]thiadiazole-5-carboxylate ($n_D^{20}$=1.5559)

(65) 6,6-difluoro-5-methyl-5-hexenyl 2-(3-pyridyl)thiazole-4-carboxylate ($n_D^{20}$=1.5527)

(66) 4,4-difluoro-3-methyl-3-butenyl 2-(4-trifluoromethylphenyl)thiazole-4-carboxylate (m.p.=65 to 66° C.)

(67) 6,6-difluoro-5-methyl-5-hexenyl 2-(2-chlorophenyl)-4-methylthiazole-5-carboxylate ($n_D^{20}$=1.5661)

(68) 4,4-difluoro-3-methyl-3-butenyl 6-ethoxynicotinate ($n_D^{20}$=1.4864)

(69) 6,6-difluoro-5-methyl-5-hexenyl 6-ethoxynicotinate ($n_D^{20}$=1.4841)

(70) 4,4-difluoro-3-methyl-3-butenyl 6-phenoxynicotinate ($n_D^{20}$=1.5364)

(71) 4,4-difluoro-3-methyl-3-butenyl 5-(2-thienyl)nicotinate ($n_D^{20}$=1.5670)

(72) 4,4-difluoro-3-methyl-3-butenyl 5-(phenylethynyl)-nicotinate ($n_D^{20}$=1.5779)

(73) 4,4-difluoro-3-methyl-3-butenyl 6-phenylnicotinate (m.p.=43 to 45° C.)

(74) 4,4-difluoro-3-methyl-3-butenyl 6-(phenylthio)nicotinate ($n_D^{20}$=1.5743)

(75) 4,4-difluoro-3-methyl-3-butenyl 6-propoxynicotinate ($n_D^{20}$=1.4860)

(76) 4,4-difluoro-3-methyl-3-butenyl 6-isopropoxy nicotinate ($n_D^{20}$=1.4831)

(77) 4,4-difluoro-3-methyl-3-butenyl 6-butoxynicotinate ($n_D^{20}$=1.4842)

(78) 6,6-difluoro-5-methyl-5-hexenyl 6-butoxynicotinate ($n_D^{20}$=1.4808)

(79) 4,4-difluoro-3-methyl-3-butenyl 6-tert-butoxynicotinate ($n_D^{20}$=1.4803)

(80) 4,4-difluoro-3-methyl-3-butenyl 6-pentyloxynicotinate ($n_D^{20}$=1.4855)

(81) 4,4-difluoro-3-methyl-3-butenyl 6-cyclopentyloxy-nicotinate ($n_D^{20}$=1.5032)

(82) 4,4-difluoro-3-methyl-3-butenyl 6-hexyloxynicotinate ($n_D^{20}$=1.4839)

(83) 4,4-difluoro-3-methyl-3-butenyl 6-cyclohexyloxy-nicotinate ($n_D^{20}$=1.5023)

(84) 4,4-difluoro-3-methyl-3-butenyl 6-heptyloxynicotinate ($n_D^{20}$=1.4825)

(85) 4,4-difluoro-3-methyl-3-butenyl 6-decyloxynicotinate ($n_D^{20}$=1.4834)

(86) 4,4-difluoro-3-methyl-3-butenyl 6-(2-butynyloxy) nicotinate ($n_D^{20}$=1.5072)

(87) 4,4-difluoro-3-methyl-3-butenyl 6-(5-hexenyloxy)-nicotinate ($n_D^{20}$=1.4923)

(88) 4,4-difluoro-3-methyl-3-butenyl 6-(2,2,2-trifluoro-ethoxy)nicotinate ($n_D^{20}$=1.4510)

(89) 4,4-difluoro-3-methyl-3-butenyl 6-(2-phenoxyethoxy)-nicotinate ($n_D^{20}$=1.5315)

(90) 4,4-difluoro-3-methyl-3-butenyl 6-(butylthio)nicotinate ($n_D^{20}$=1.5244)

(91) 4,4-difluoro-3-methyl-3-butenyl 6-(hexylthio)nicotinate ($n_D^{20}$=1.5093)

(92) 4,4-difluoro-3-methyl-3-butenyl 6-(N-methyl-N-phenyl-amino)nicotinate ($n_D^{20}$=not measurable)

$^1$H-NMR ($CDCl_3$, TMS) δ ppm: 1.65 (3H, t), 2.37-2.43 (2H, m), 3.53 (3H, s), 4.31 (2H, t), 6.40 (1H, d), 7.22-7.33 (3H, m), 7.45 (2H, t), 7.83 (1H, dd), 8.86 (1H, d)

(93) 4,4-difluoro-3-methyl-3-butenyl 4-methyl-2-phenyl-pyrimidine-5-carboxylate (m.p.=32 to 34° C.)

(94) 6,6-difluoro-5-methyl-5-hexenyl 4-methyl-2-phenyl-pyrimidine-5-carboxylate ($n_D^{20}$=1.5455)

(95) 4,4-difluoro-3-methyl-3-butenyl 2-isopropyl-4-methyl-pyrimidine-5-carboxylate ($n_D^{20}$=1.4773)

(96) 4,4-difluoro-3-methyl-3-butenyl 2-cyclopropyl-4-methyl-pyrimidine-5-carboxylate ($n_D^{20}$=1.5031)

(97) 6,6-difluoro-5-methyl-5-hexenyl 2-cyclopropyl-4-methyl-pyrimidine-5-carboxylate ($n_D^{20}$=1.4975)

(98) 4,4-difluoro-3-methyl-3-butenyl 2-butyl-4-methyl-pyrimidine-5-carboxylate ($n_D^{20}$=1.4790)

(99) 4,4-difluoro-3-methyl-3-butenyl 2-tert-butyl-4-methyl-pyrimidine-5-carboxylate ($n_D^{20}$=1.4755)

(100) 6,6-difluoro-5-methyl-5-hexenyl 2-tert-butyl-4-methyl-pyrimidine-5-carboxylate-5-carboxylate ($n_D^{20}$=1.4735)

(101) 4,4-difluoro-3-methyl-3-butenyl 4-methyl-2-pentyl-pyrimidine-5-carboxylate ($n_D^{20}$=1.4787)

(102) 4,4-difluoro-3-methyl-3-butenyl 2-hexyl-4-methyl-pyrimidine-5-carboxylate ($n_D^{20}$=1.4780)

(103) 4,4-difluoro-3-methyl-3-butenyl 2-heptyl-4-methyl-pyrimidine-5-carboxylate ($n_D^{20}$=1.4767)

(104) 4,4-difluoro-3-methyl-3-butenyl 4-methyl-2-propoxy-pyrimidine-5-carboxylate ($n_D^{20}$=1.4850)

(105) 4,4-difluoro-3-methyl-3-butenyl 2-butoxy-4-methyl-pyrimidine-5-carboxylate ($n_D^{20}$=1.4857)

(106) 4,4-difluoro-3-methyl-3-butenyl 4-methyl-2-pentyloxy-pyrimidine-5-carboxylate ($n_D^{20}$=not measurable)

$^1$H-NMR ($CDCl_3$, TMS) δ ppm: 0.92 (3H, t), 1.32-1.51 (4H, m), 1.64 (3H, t), 1.78-1.87 (2H, m), 2.40-2.47(2H, m), 2.76 (3H, s), 4.35-4.44 (4H, m), 8.96 (1H, s)

(107) 4,4-difluoro-3-methyl-3-butenyl 2-hexyloxy-4-methyl-pyrimidine-5-carboxylate ($n_D^{20}$=not measurable)

$^1$H-NMR ($CDCl_3$, TMS) δ ppm: 0.90 (3H, t), 1.24-1.53 (6H, m), 1.66 (3H, t), 1.77-1.87 (2H, m), 2.41-2.47 (2H, m), 2.76 (3H, s), 4.35-4.44 (4H, m), 8.96 (1H, s)

(108) 4,4-difluoro-3-methyl-3-butenyl 4-methyl-2-octyloxy-pyrimidine-5-carboxylate ($n_D^{20}$=1.4795)

(109) 4,4-difluoro-3-methyl-3-butenyl 4-methyl-2-phenoxy-pyrimidine-5-carboxylate ($n_D^{20}$=1.5351)

(110) 4,4-difluoro-3-methyl-3-butenyl 4-methyl-2-(methylthio)pyrimidine-5-carboxylate ($n_D^{20}$=1.5312)

(111) 4,4-difluoro-3-methyl-3-butenyl 2-methanesulfonyl-4-methylpyrimidine-5-carboxylate ($n_D^{20}$=not measurable)

$^1$H-NMR ($CDCl_3$, TMS) δ ppm: 1.67 (3H, t), 2.46-2.50 (2H, m), 2.95 (3H, s), 3.39 (3H, s), 4.47 (2H, t), 9.25 (1H, s)

(112) 4,4-difluoro-3-methyl-3-butenyl 4-methyl-2-(propylthio)pyrimidine-5-carboxylate ($n_D^{20}$=1.5242)

(113) 4,4-difluoro-3-methyl-3-butenyl 2-butylthio-4-methylpyrimidine-5-carboxylate ($n_D^{20}$=1.5191)

(114) 4,4-difluoro-3-methyl-3-butenyl 4-methyl-2-(pentylthio)pyrimidine-5-carboxylate ($n_D^{20}$=1.5165)

(115) 4,4-difluoro-3-methyl-3-butenyl 2-hexylthio-4-methylpyrimidine-5-carboxylate ($n_D^{20}$=1.5137)

(116) 4,4-difluoro-3-methyl-3-butenyl 2-heptylthio-4-methylpyrimidine-5-carboxylate ($n_D^{20}$=1.5060)

(117) 4,4-difluoro-3-methyl-3-butenyl 4-methyl-2-(phenylthio)pyrimidine-5-carboxylate ($n_D^{20}$=1.5660)

(118) 4,4-difluoro-3-methyl-3-butenyl 4-methyl-2-(N-phenylamino)pyrimidine-5-carboxylate (m.p.=102 to 103° C.)

(119) 4,4-difluoro-3-methyl-3-butenyl 4-methyl-2-(N-methyl-N-phenylamino)pyrimidine-5-carboxylate ($n_D^{20}$=not measurable)

$^1$H-NMR ($CDCl_3$, TMS) δ ppm: 1.63(3H, t), 2.37-2.42 (2H, m), 2.66 (3H, s), 3.59 (3H, s), 4.31 (2H, t), 7.25-7.33 (3H, m), 7.40-7.45 (2H, m), 8.79 (1H, s)

(120) 4,4-difluoro-3-methyl-3-butenyl 2-(N-ethyl-N-phenylamino)-4-methylpyrimidine-5-carboxylate ($n_D^{20}$=1.5586)

(121)4,4-difluoro-3-methyl-3-butenyl 4-methyl-2-(N-phenyl-N-propylamino)pyrimidine-5-carboxylate ($n_D^{20}$=1.5522)

(122) 4,4-difluoro-3-methyl-3-butenyl 4-methyl-2-(N-phenyl-N-2-propenylamino)pyrimidine-5-carboxylate ($n_D^{20}$=1.5630)

(123) 4,4-difluoro-3-methyl-3-butenyl 4-methyl-2-(N-phenyl-N-2-propynylamino)pyrimidine-5-carboxylate ($n_D^{20}$=1.5633)

(124) 4,4-difluoro-3-methyl-3-butenyl 2-(N,N-dipropylamino)-4-methylpyrimidine-5-carboxylate ($n_D^{20}$=1.5098)

(125) 4,4-difluoro-3-methyl-3-butenyl 2-(N,N-dibutylamino)-4-methylpyrimidine-5-carboxylate ($n_D^{20}$=1.5011)

(126) 4,4-difluoro-3-methyl-3-butenyl 5-phenylthiophene-2-carboxylate (m.p.=38 to 39° C.)

(127) 4,4-difluoro-3-methyl-3-butenyl 5-(2-methyl-5-trifluoromethyl-2H-3-pyrazolyl)thiophene-2-carboxylate (m.p.=59 to 60° C.)

(128) 4,4-difluoro-3-methyl-3-butenyl 2-methyl-1,5-diphenyl-1H-pyrrole-3-carboxylate (m.p.=82 to 84° C.)

(129) 6,6-difluoro-5-methyl-5-hexenyl 2-phenylthiazole-4-carboxylate ($n_D^{20}$=1.5508)

(130) 6,6-difluoro-5-methyl-5-hexenyl 2-(4-chlorophenyl)-4-methylthiazole-5-carboxylate (m.p.=50 to 51° C.)

(131) 6,6-difluoro-5-methyl-5-hexenyl 4-methyl-2-phenoxy-thiazole-5-carboxylate ($n_D^{20}$=1.5291)

(132) 6,6-difluoro-5-methyl-5-hexenyl 2-phenylthiazole-5-carboxylate ($n_D^{20}$=1.5601)

(133) 6,6-difluoro-5-methyl-5-hexenyl 2-(3-chlorophenyl)-4-methylthiazole-5-carboxylate ($n_D^{20}$=1.5613)

(134) 4,4-difluoro-3-methyl-3-butenyl 4-methyl-2-(4-nitrophenyl)thiazole-5-carboxylate (m.p.=89 to 90° C.)

(135) 4,4-difluoro-3-methyl-3-butenyl 2-(4-aminophenyl)-4-methylthiazole-5-carboxylate (m.p.=73 to 76° C.)

(136) 4,4-difluoro-3-methyl-3-butenyl 2-(4-N,N-dimethylaminophenyl)-4-methylthiazole-5-carboxylate (m.p.=69 to 72° C.)

(137) 4,4-difluoro-3-methyl-3-butenyl 2-(4-acetylaminophenyl)-4-methylthiazole-5-carboxylate (m.p.=161 to 163° C.)

(138) 4,4-difluoro-3-methyl-3-butenyl 2-(4-diacetylaminophenyl)-4-methylthiazole-5-carboxylate (m.p.=60 to 62° C.)

(139) 4,4-difluoro-3-methyl-3-butenyl 4-methyl-2-(phenylthio)thiazole-5-carboxylate (m.p.=52 to 53° C.)

(140) 4,4-difluoro-3-methyl-3-butenyl 2-benzenesulfinyl-4-methylthiazole-5-carboxylate (m.p.=87 to 89° C.)

(141) 4,4-difluoro-3-methyl-3-butenyl 2-benzenesulfonyl-4-methylthiazole-5-carboxylate (m.p.=102 to 103° C.)

(142) 4,4-difluoro-3-methyl-3-butenyl 4-methyl-2-(4-trifluoromethylphenyl)thiazole-5-carboxylate (m.p.=53 to 54° C.)

(143) 6,6-difluoro-5-methyl-5-hexenyl 2-(2-methoxyphenyl)-4-methylthiazole-5-carboxylate (m.p.=63 to 64° C.)

(144) 6,6-difluoro-5-methyl-5-hexenyl 2-(3-methoxyphenyl)-4-methylthiazole-5-carboxylate ($n_D^{20}$=1.5601)

(145) 6,6-difluoro-5-methyl-5-hexenyl 2-(4-methoxyphenyl)-4-methylthiazole-5-carboxylate ($n_D^{20}$=1.5722)

(146) 4,4-difluoro-3-methyl-3-butenyl 2-benzyl-4-methylthiazole-5-carboxylate ($n_D^{20}$=1.5360)

(147) 6,6-difluoro-5-methyl-5-hexenyl 2-benzyl-4-methylthiazole-5-carboxylate ($n_D^{20}$=1.5274)

(148) 4,4-difluoro-3-methyl-3-butenyl 2,4-dimethylthiazole-5-carboxylate ($n_D^{20}$=1.4910)

(149) 6,6-difluoro-5-methyl-5-hexenyl 2,4-dimethylthiazole-5-carboxylate ($n_D^{20}$=1.4884)

(150) 4,4-difluoro-3-methyl-3-butenyl 2-ethyl-4-methylthiazole-5-carboxylate ($n_D^{20}$=1.4904)

(151) 6,6-difluoro-5-methyl-5-hexenyl 2-ethyl-4-methylthiazole-5-carboxylate ($n_D^{20}$=1.4845)

(152) 4,4-difluoro-3-methyl-3-butenyl 4-methyl-2-propylthiazole-5-carboxylate ($n_D^{20}$=1.4872)

(153) 6,6-difluoro-5-methyl-5-hexenyl 4-methyl-2-propyl-20=thiazole-5-carboxylate ($n_D^{20}$=1.4859)

(154) 4,4-difluoro-3-methyl-3-butenyl 2-isopropyl-4-methylthiazole-5-carboxylate ($n_D^{20}$=1.4876)

(155) 6,6-difluoro-5-methyl-5-hexenyl 2-isopropyl-4-methylthiazole-5-carboxylate ($n_D^{20}$=1.4855)

(156) 4,4-difluoro-3-methyl-3-butenyl 2-cyclopropyl-4-methylthiazole-5-carboxylate ($n_D^{20}$=1.5119)

(157) 6,6-difluoro-5-methyl-5-hexenyl 2-cyclopropyl-4-methylthiazole-5-carboxylate ($n_D^{20}$=1.5055)

(158) 4,4-difluoro-3-methyl-3-butenyl 2-butyl-4-methylthiazole-5-carboxylate ($n_D^{20}$=1.4875)

(159) 6,6-difluoro-5-methyl-5-hexenyl 2-butyl-4-methylthiazole-5-carboxylate ($n_D^{20}$=1.4852)

(160) 4,4-difluoro-3-methyl-3-butenyl 2-tert-butyl-4-methylthiazole-5-carboxylate ($n_D^{20}$=1.4851)

(161) 6,6-difluoro-5-methyl-5-hexenyl 2-tert-butyl-4-methylthiazole-5-carboxylate ($n_D^{20}$=1.4824)

(162) 4,4-difluoro-3-methyl-3-butenyl 2-isobutyl-4-methylthiazole-5-carboxylate ($n_D^{20}$=1.4851)

(163) 4,4-difluoro-3-methyl-3-butenyl 4-methyl-2-pentylthiazole-5-carboxylate ($n_D^{20}$=1.4853)

(164) 6,6-difluoro-5-methyl-5-hexenyl 4-methyl-2-pentylthiazole-5-carboxylate ($n_D^{20}$=1.4840)

(165) 4,4-difluoro-3-methyl-3-butenyl 2-(1-ethylpropyl)-4-methylthiazole-5-carboxylate ($n_D^{20}$=1.4850)

(166) 6,6-difluoro-5-methyl-5-hexenyl 2-(1-ethylpropyl)-4-methylthiazole-5-carboxylate ($n_D^{20}$=1.4847)

(167) 4,4-difluoro-3-methyl-3-butenyl 2-cyclopentyl-4-methylthiazole-5-carboxylate ($n_D^{20}$=1.5067)

(168) 4,4-difluoro-3-methyl-3-butenyl 2-hexyl-4-methylthiazole-5-carboxylate ($n_D^{20}$=1.4855)

(169) 4,4-difluoro-3-methyl-3-butenyl 2-cyclohexyl-4-methylthiazole-5-carboxylate ($n_D^{20}$=1.5067)

(170) 4,4-difluoro-3-methyl-3-butenyl 2-ethoxy-4-methylthiazole-5-carboxylate ($n_D^{20}$=1.4919)

(171) 6,6-difluoro-5-methyl-5-hexenyl 2-ethoxy-4-methylthiazole-5-carboxylate ($n_D^{20}$=1.4861)

(172) 4,4-difluoro-3-methyl-3-butenyl 4-methyl-2-(N-phenylamino)thiazole-5-carboxylate (m.p.=67 to 68° C.)

(173) 4,4-difluoro-3-methyl-3-butenyl 4-methyl-2-(N-methyl-N-phenylamino)thiazole-5-carboxylate ($n_D^{20}$=1.5739)

(174) 4,4-difluoro-3-methyl-3-butenyl 2-(N-ethyl-N-phenylamino)-4-methylthiazole-5-carboxylate ($n_D^{20}$=1.5595)

(175) 4,4-difluoro-3-methyl-3-butenyl 4-methyl-2-(N-phenyl-N-propylamino)thiazole-5-carboxylate ($n_D^{20}$=1.5566)

(176) 4,4-difluoro-3-methyl-3-butenyl 4-methyl-2-(N-phenyl-N-2-propenylamino)thiazole-5-carboxylate ($n_D^{20}$=1.5661)

(177) 4,4-difluoro-3-methyl-3-butenyl 4-methyl-2-(N-phenyl-N-2-propynylamino)thiazole-5-carboxylate ($n_D^{20}$=not measurable)

$^1$H-NMR ($CDCl_3$, TMS) δ ppm: 1.58 (3H, t), 2.27-2.33 (3H, m), 2.59 (3H, s), 4.21 (2H, t), 4.74 (2H, d), 7.38-7.51 (5H, m)

(178) 4,4-difluoro-3-methyl-3-butenyl 2-[N-(2-chlorophenyl)-amino]-4-methylthiazole-5-carboxylate (m.p.=78 to 80° C.)

(179) 4,4-difluoro-3-methyl-3-butenyl 2-[N-(4-methoxyphenyl)-amino]-4-methylthiazole-5-carboxylate (m.p.=86 to 88° C.)

(180) 4,4-difluoro-3-methyl-3-butenyl 2-[N-(4-methoxyphenyl)-N-methylamino]-4-methylthiazole-5-carboxylate ($n_D^{20}$=1.5722)

(181) 4,4-difluoro-3-methyl-3-butenyl 2-[N-isopropyl-N-(4-methoxyphenyl)amino]-4-methylthiazole-5-carboxylate ($n_D^{20}$=1.5722)

(182) 4,4-difluoro-3-methyl-3-butenyl 2-[N-methanesulfonyl-N-(4-methoxyphenyl)amino]-4-methylthiazole-5-carboxylate ($n_D^{20}$=not measurable)

(183) 4,4-difluoro-3-methyl-3-butenyl 4-methyl-2-(N-4-tolyl-amino)thiazole-5-carboxylate (m.p.=96 to 97° C.)

(184) 4,4-difluoro-3-methyl-3-butenyl 4-methyl-2-(N-methyl-4-tolylamino)thiazole-5-carboxylate ($n_D^{20}$=1.5659)

(185) 4,4-difluoro-3-methyl-3-butenyl 2-(N-ethyl-N-4-tolylamino)-4-methylthiazole-5-carboxylate ($n_D^{20}$=1.5605)

(186) 4,4-difluoro-3-methyl-3-butenyl 2-(N-tert-butoxy-carbonyl-N-4-tolylamino)-4-methylthiazole-5-carboxylate (m.p.=112 to 113° C.)

(187) 4,4-difluoro-3-methyl-3-butenyl 2-[3,3-dimethyl-1-(4-tolyl)ureido]-4-methylthiazole-5-carboxylate ($n_D^{20}$=1.5592)

(188) 4,4-difluoro-3-methyl-3-butenyl 4-methyl-2 [N-(3-trifluoromethylphenyl)amino]thiazole-5-carboxylate (m.p.=91 to 93° C.)

(189) 4,4-difluoro-3-methyl-3-butenyl 4-methyl-2-[N-methyl-N-(3-trifluoromethylphenyl)amino]thiazole-5-carboxylate ($n_D^{20}$=1.5396)

(190) 4,4-difluoro-3-methyl-3-butenyl 2-phenylthiazole-5-carboxylate (m.p.=47 to 49° C.)

(191) 4,4-difluoro-3-methyl-3-butenyl 2-phenylthiazole-4-carboxylate ($n_D^{20}$=1.5611)

(192) 4,4-difluoro-3-methyl-3-butenyl 2-(N-phenylamino)-thiazole-4-carboxylate (m.p.=103 to 104° C.)

(193) 4,4-difluoro-3-methyl-3-butenyl 2-(N-methyl-N-phenylamino)thiazole-4-carboxylate ($n_D^{20}$=1.5612)

(194) 4,4-difluoro-3-methyl-3-butenyl 1-methyl-5-phenyl-1H-pyrazole-3-carboxylate ($n_D^{20}$=1.5353)

(195) 4,4-difluoro-3-methyl-3-butenyl 4-chloro-1-methyl-5-phenyl-1H-pyrazole-3-carboxylate ($n_D^{20}$=1.5427)

(196) 4,4-difluoro-3-methyl-3-butenyl 3-methyl-1-phenyl-1H-pyrazole-4-carboxylate ($n_D^{20}$=1.5353)

(197) 4,4-difluoro-3-methyl-3-butenyl 1-benzyl-3-methyl-1H-pyrazole-4-carboxylate ($n_D^{20}$=1.5177)

(198) 4,4-difluoro-3-methyl-3-butenyl 3-methyl-1-propyl-1H-pyrazole-4-carboxylate ($n_D^{20}$=1.4726)

(199) 4,4-difluoro-3-methyl-3-butenyl 1-butyl-3-methyl-1H-pyrazole-4-carboxylate ($n_D^{20}$=1.4701)

(200) 4,4-difluoro-3-methyl-3-butenyl 5-methyl-1-phenyl-1H-pyrazole-4-carboxylate ($n_D^{20}$=1.5253)

(201) 6,6-difluoro-5-methyl-5-hexenyl 5-methyl-1-phenyl-1H-pyrazole-4-carboxylate ($n_D^{20}$=1.5232)

(202) 4,4-difluoro-3-methyl-3-butenyl 1-benzyl-5-methyl-1H-pyrazole-4-carboxylate ($n_D^{20}$=1.5130)

(203) 4,4-difluoro-3-methyl-3-butenyl 1-butyl-5-methyl-1H-pyrazole-4-carboxylate ($n_D^{20}$=1.4679)

(204) 4,4-difluoro-3-methyl-3-butenyl 2-methyl-5-phenyl-2H-pyrazole-3-carboxylate ($n_D^{20}$=1.5383)

(205) 4,4-difluoro-3-methyl-3-butenyl 4-chloro-2-methyl-5-phenyl-2H-pyrazole-3-carboxylate ($n_D^{20}$=1.5487)

(206) 4,4-difluoro-3-methyl-3-butenyl 2-methyl-5-propyl-2H-pyrazole-3-carboxylate ($n_D^{20}$=1.4622)

(207) 4,4-difluoro-3-methyl-3-butenyl 5-butyl-2-methyl-2H-pyrazole-3-carboxylate ($n_D^{20}$=1.4701)

(208) 4,4-difluoro-3-methyl-3-butenyl 2-methyl-5-pentyl-2H-pyrazole-3-carboxylate ($n_D^{20}$=1.4692)

(209) 4,4-difluoro-3-methyl-3-butenyl quinoxaline-6-carboxylate (m.p.=42 to 44° C.)

(210) 4,4-difluoro-3-methyl-3-butenyl benzo[b]thiophene-3-carboxylate ($n_D^{20}$=1.5549)

(211) 4,4-difluoro-3-methyl-3-butenyl 4-methyl-2-(1-pyrrolidinyl)pyrimidine-5-carboxylate (m.p.=48 to 49° C.)

(212) 4,4-difluoro-3-methyl-3-butenyl 4-methyl-2-(1-piperidinyl)pyrimidine-5-carboxylate (m.p.=63 to 64° C.)

(213) 4,4-difluoro-3-methyl-3-butenyl 2-(N-hexyl-N-methyl-amino)-4-methylpyrimidine-5-carboxylate ($n_D^{20}$=1.5069)

(214) 4,4-difluoro-3-methyl-3-butenyl 2-(N-butyl-N-methyl-amino)-4-methylpyrimidine-5-carboxylate ($n_D^{20}$=1.5116)

(215) 4,4-difluoro-3-methyl-3-butenyl 2-(N-hydroxy-N-methyl-amino)-4-methylpyrimidine-5-carboxylate (m.p.=96 to 97° C.)

(216) 4,4-difluoro-3-methyl-3-butenyl 2-(N-butoxy-N-methyl-amino)-4-methylpyrimidine-5-carboxylate ($n_D^{20}$=1.4968)

(217) 4,4-difluoro-3-methyl-3-butenyl 2-phenylpyrimidine-5-carboxylate (m.p.=76 to 77° C.)

(218) 4,4-difluoro-3-methyl-3-butenyl 2-benzyl-4-methyl-pyrimidine-5-carboxylate ($n_D^{20}$=1.5280)

(219) 4,4-difluoro-3-methyl-3-butenyl 4-ethyl-2-phenyl-pyrimidine-5-carboxylate ($n_D^{20}$=10.5515)

(220) 4,4-difluoro-3-methyl-3-butenyl 2-[N-(2-chlorophenyl)-N-methylamino]-4-methylthiazole-5-carboxylate ($n_D^{20}$=1.5765)

(221) 4,4-difluoro-3-methyl-3-butenyl 2-(4-chloro-phenyl) amino]-4-methylthiazole-5-carboxylate (m.p.=110 to 112° C.)

(222) 4,4-difluoro-3-methyl-3-butenyl 2-[N-(4-chlorophenyl)-N-methylamino]-4-methylthiazole-5-carboxylate (m.p.=54 to 56° C.)

(223) 4,4-difluoro-3-methyl-3-butenyl 2-methyl-6-phenyl-pyrimidine-4-carboxylate (m.p.=64 to 67° C.)

(224) 4,4-difluoro-3-methyl-3-butenyl 2-(N-benzyl-N-methylamino)-4-methylpyrimidine-5-carboxylate ($n_D^{20}$=1.5537)

(225) 4,4-difluoro-3-methyl-3-butenyl-4-methyl-2-(N-methyl-N-2-propynylamino)pyrimidine-5-carboxylate ($n_D^{20}$=1.5264)

(226) 4,4-difluoro-3-methyl-3-butenyl 2-(N-ethyl-N-methylamino)-4-methylpyrimidine-5-carboxylate ($n_D^{20}$=1.5174)

(227) 4,4-difluoro-3-methyl-3-butenyl 4-methyl-2-(N-methyl-N-propylamino)pyrimidine-5-carboxylate ($n_D^{20}$=1.5100)

(228) 4,4-difluoro-3-methyl-3-butenyl 2-(N-isopropyl-N-methylamino)-4-methylpyrimidine-5-carboxylate ($n_D^{20}$=1.5197)

(229) 4,4-difluoro-3-methyl-3-butenyl 4-methyl-2-(N-methyl-N-pentylamino)pyrimidine-5-carboxylate ($n_D^{20}$=1.5052)

(230) 4,4-difluoro-3-methyl-3-butenyl 2-dimethylamino-4-methylpyrimidine-5-carboxylate (m.p.=37 to 38° C.)

(231) 4,4-difluoro-3-methyl-3-butenyl 2-methoxyamino-4-methylpyrimidine-5-carboxylate (m.p.=62 to 64° C.)

(232) 4,4-difluoro-3-methyl-3-butenyl 2-(N-methoxy-N-methylamino)-4-methylpyrimidine-5-carboxylate ($n_D^{20}$=1.5124)

(233) 4,4-difluoro-3-methyl-3-butenyl 2-methoxycarbonylnicotinate ($n_D^{20}$=1.4832)

(234) 4,4-difluoro-3-methyl-3-butenyl 3-phenylcarbamoylpyridine-2-carboxylate (m.p.=79 to 81° C.)

(235) 4,4-difluoro-3-methyl-3-butenyl 2-phenylcarbamoylnicotinate (m.p.=69 to 72° C.)

(236) 4,4-difluoro-3-methyl-3-butenyl 2-(N,N-diethyl-carbamoyl)nicotinate ($n_D^{20}$=1.4962)

(237) 4,4-difluoro-3-methyl-3-butenyl 2-benzoylnicotinate ($n_D^{20}$=1.5351)

(238) 6,6-difluoro-5-methyl-5-hexenyl 1-oxynicotinate ($n_D^{20}$=not measurable)

$^1$H-NMR ($CDCl_3$, TMS) δ ppm: 1.49-1.59 (5H, m), 1.72-1.81 (2H, m), 2.01-2.07 (2H, m), 4.37 (2H, t), 7.39 (1H, t), 7.88 (1H, d), 8.37 (1H, s), 8.80 (1H, s)

(239) 4,4-difluoro-3-methyl-3-butenyl 2-[4-(4-chlorobenzoyl-amino)phenyl]-4-methylthiazole-5-carboxylate (m.p.=189 to 191° C.)

(240) 4,4-difluoro-3-methyl-3-butenyl 1-(4,4-difluoro-3-methyl-3-butenyl)-4-nitro-1H-pyrazole-3-carboxylate ($n_D^{20}$=not measurable)

$^1$H-NMR ($CDCl_3$, TMS) δ ppm: 1.58 (3H, t), 1.64 (3H, t), 2.43-2.47 (2H, m), 2.57-2.62 (2H, m), 4.25 (2H, t), 4.45 (2H, t), 8.12 (1H, s)

(241) 4,4-difluoro-3-methyl-3-butenyl 2-(4,4-difluoro-3-methyl-3-butenyl)-4-nitro-2H-pyrazole-3-carboxylate ($n_D^{20}$=1.4748)

(242) 4,4-difluoro-3-methyl-3-butenyl 2-methyl-2,4,5,6-tetrahydrocyclopentapyrazole-3-carboxylate ($n_D^{20}$=1.4915)

(243) 4,4-difluoro-3-methyl-3-butenyl 2-(4-chlorophenyl)-4-methylpyrimidine-5-carboxylate (m.p.=72 to 73° C.)

(244) 4,4-difluoro-3-methyl-3-butenyl 4-methyl-2-(4-trifluoromethylphenyl)pyrimidine-5-carboxylate (m.p.=57 to 59° C.)

(245) 4,4-difluoro-3-methyl-3-butenyl 2-(4-methoxyphenyl)-4-methylpyrimidine-5-carboxylate (m.p.=66 to 68° C.)

(246) 4,4-difluoro-3-methyl-3-butenyl 4-methyl-2-(4-methyl-phenyl)pyrimidine-5-carboxylate (m.p.=60 to 62° C.)

(247) 6,6-difluoro-5-methyl-5-hexenyl 2-ethoxy-4-methyl-pyrimidine-5-carboxylate ($n_D^{20}$=1.4825)

(248) 6,6-difluoro-5-methyl-5-hexenyl 4-methyl-2-propoxy-pyrimidine-5-carboxylate ($n_D^{20}$=1.4812)

(249) 6,6-difluoro-5-methyl-5-hexenyl 2-butoxy-4-methyl-pyrimidine-5-carboxylate ($n_D^{20}$=1.4807)

(250) 4,4-difluoro-3-methyl-3-butenyl 2-cyclopentyloxy-4-methylpyrimidine-5-carboxylate ($n_D^{20}$=1.5028)

(251) 4,4-difluoro-3-methyl-3-butenyl 2-cyclohexyloxy-4-methylpyrimidine-5-carboxylate ($n_D^{20}$=1.5041)

(252) 4,4-difluoro-3-methyl-3-butenyl 2-(2-methoxy-ethoxy)-4-methylpyrimidine-5-carboxylate ($n_D^{20}$=1.4858)

(253) 4,4-difluoro-3-methyl-3-butenyl 2-cyclopropyl-methoxy-4-methylpyrimidine-5-carboxylate ($n_D^{20}$=1.4954)

(254) 4,4-difluoro-3-methyl-3-butenyl 2-(4-chlorobutoxy)-4-methylpyrimidine-5-carboxylate ($n_D^{20}$=1.4911)

(255) 4,4-difluoro-3-methyl-3-butenyl 4-methyl-2-(3-pyridyloxy)pyrimidine-5-carboxylate ($n_D^{20}$=1.5317)

(256) 4,4-difluoro-3-methyl-3-butenyl 4-methyl-2-(6-methyl-2-pyridyloxy)pyrimidine-5-carboxylate (m.p.=102 to 104° C.)

(257) 6,6-difluoro-5-methyl-5-hexenyl 4-methyl-2-(methylthio)pyrimidine-5-carboxylate ($n_D^{20}$=1.5153)

(258) 6,6-difluoro-5-methyl-5-hexenyl 2-(N,N-diethylamino)-4-methylpyrimidine-5-carboxylate ($n_D^{20}$=1.5079)

(259) 4,4-difluoro-3-methyl-3-butenyl 2-(N-acetyl-N-methylamino)-4-methylpyrimidine-5-carboxylate ($n_D^{20}$=1.5162)

(260) 6,6-difluoro-5-methyl-5-hexenyl 2-(N,N-dimethylamino)-4-methylpyrimidine-5-carboxylate ($n_D^{20}$=1.5130)

(261) 4,4-difluoro-3-methyl-3-butenyl 2-(N-butylamino)-4-methylpyrimidine-5-carboxylate (m.p.=42 to 43° C.)

(262) 4,4-difluoro-3-methyl-3-butenyl 2-(N-butyl-N-methoxy-amino)-4-methylpyrimidine-5-carboxylate ($n_D^{20}$=1.4981)

(263) 4,4-difluoro-3-methyl-3-butenyl 2-(N-butyl-N-trifluoro-acetylamino)-4-methylpyrimidine-5-carboxylate ($n_D^{20}$=1.4729)

(264) 4,4-difluoro-3-methyl-3-butenyl 2-(N-cyclohexylamino)-4-methylpyrimidine-5-carboxylate (m.p.=59 to 61° C.)

(265) 4,4-difluoro-3-methyl-3-butenyl 2-(N-cyclohexyl-N-methylamino)-4-methylpyrimidine-5-carboxylate (m.p.=46 to 47° C.)

(266) 6,6-difluoro-5-methyl-5-hexenyl 2-(N-methoxy-N-methylamino)-4-methylpyrimidine-5-carboxylate ($n_D^{20}$=not measurable)

$^1$H-NMR ($CDCl_3$, TMS) δ ppm: 1.51-1.59 (5H, m), 1.69-1.78 (2H, m), 2.01-2.06 (2H, m), 2.72(3H, s), 3.47 (3H, s), 3.85 (3H, s), 4.29 (2H, t), 8.92 (1H, s)

(267) 4,4-difluoro-3-methyl-3-butenyl 2-(N-benzoyl-N-methylamino)-4-methylpyrimidine-5-carboxylate ($n_D^{20}$=1.5479)

(268) 6,6-difluoro-5-methyl-5-hexenyl 2-cyano-4-methyl-pyrimidine-5-carboxylate ($n_D^{20}$=1.4869)

(269) 4,4-difluoro-3-methyl-3-butenyl 4-methyl-2-phthalimidopyrimidine-5-carboxylate ($n_D^{20}$=not measurable)

$^1$H-NMR ($CDCl_3$, TMS) δ ppm: 1.68(3H, t), 2.45-2.51 (2H, m), 2.93 (3H, s), 4.45 (2H, t), 7.82-7.85 (2H, m), 7.99-8.02 (2H, m), 9.29 (1H, s)

(270) 6,6-difluoro-5-methyl-5-hexenyl 2-methanesulfinyl-4-methylpyrimidine-5-carboxylate ($n_D^{20}$=not measurable)

$^1$H-NMR ($CDCl_3$, TMS) δ ppm: 1.51-1.61 (5H, m), 1.74-1.84 (2H, m), 2.02-2.09 (2H, m), 2.94 (3H, s), 2.98 (3H, s), 4.40 (2H, t), 9.23 (1H, s)

(271) 6,6-difluoro-5-methyl-5-hexenyl 2-methanesulfonyl-4-methylpyrimidine-5-carboxylate ($n_D^{20}$=not measurable)

$^1$H-NMR ($CDCl_3$, TMS) δ ppm: 1.51-1.61 (5H, m), 1.75-1.84(2H, m), 2.02-2.09 (2H, m), 2.96 (3H, s), 3.39 (3H, s), 4.42 (2H, t), 9.26 (1H, s)

(272) 4,4-difluoro-3-methyl-3-butenyl 2-butoxy-4-trifluoromethylpyrimidine-5-carboxylate ($n_D^{20}$=1.4520)

(273) 4,4-difluoro-3-methyl-3-butenyl 4-methoxymethylpyrimidine-5-carboxylate ($n_D^{20}$=1.4766)

(274) 4,4-difluoro-3-methyl-3-butenyl 6-methyl-2-phenyl-pyrimidine-4-carboxylate ($n_D^{20}$=1.5431)

(275) 4,4-difluoro-3-methyl-3-butenyl 2-butoxy-6-methyl-pyrimidine-4-carboxylate ($n_D^{20}$=1.4757)

(276) 4,4-difluoro-3-methyl-3-butenyl 6-butoxy-2-methyl-pyrimidine-4-carboxylate ($n_D^{20}$=1.4705)

(277) 4,4-difluoro-3-methyl-3-butenyl 4-(N,N-dimethylamino)-6-(3-trifluoromethylphenoxy)pyrimidine-2-carboxylate (m.p.=37 to 39° C.)

(278) 4,4-difluoro-3-methyl-3-butenyl 4-methyl-6-phenyl-pyrimidine-2-carboxylate ($n_D^{20}$=1.5466)

(279) 4,4-difluoro-3-methyl-3-butenyl 1H-pyrrole-2-carboxylate ($n_D^{20}$=1.4853)

(280) 4,4-difluoro-3-methyl-3-butenyl 1-(2-propenyl)-1H-pyrrole-2-carboxylate ($n_D^{20}$=1.4872)

(281) 4,4-difluoro-3-methyl-3-butenyl 1-cyclopropylmethyl-1H-pyrrole-2-carboxylate ($n_D^{20}$=1.4920)

(282) 4,4-difluoro-3-methyl-3-butenyl 1-cyanomethyl-1H-pyrrole-2-carboxylate ($n_D^{20}$=1.4628)

(283) 4,4-difluoro-3-methyl-3-butenyl 3-trifluoroacetyl-1H-pyrrole-2-carboxylate (m.p.=51 to 54° C.)

(284) 4,4-difluoro-3-methyl-3-butenyl 4-trifluoroacetyl-1H-pyrrole-2-carboxylate (m.p.=67 to 70° C.)

(285) 4,4-difluoro-3-methyl-3-butenyl 1-(3-butynyl)-1H-pyrrole-2-carboxylate ($n_D^{20}$=1.4867)

Next, production methods for intermediate compounds shown by [A], [B] and [C] are explained.

An intermediate compound shown by the general formula [A] can be produced in accordance with the production method shown below.

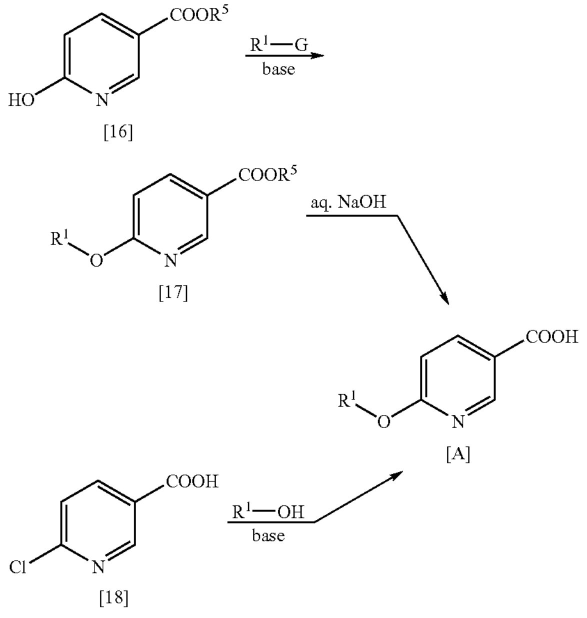

[16] [17] [A] [18]

(wherein $R^1$ and G represent the same meaning described above. $R^5$ represents a methyl group or an ethyl group. A base includes similar one to that, for example, used in the production method 2.) A compound [18] can be available as a commercial product. A compound [16] can be synthesized by the method described in, for example, "J. Chem. Soc.", page 1379 (1908).

Next, examples of production methods for intermediate compounds shown by [A] are explained.

Intermediate Production Example 1

Production of the Intermediate Compound A-2

To 30 ml of N,N-dimethylformamide, 1.00 g (6.4 mmol) of 6-chloronicotinic acid and 1.72 g (20 mmol) of cyclopentanol were dissolved, followed by adding 0.80 g (20 mmol) of 60% sodium hydride, stirring at room temperature for 1 hour and heating under refluxing for 3 hours. The reaction liquid was then poured in 100 ml of ice water and acetic acid was added to make pH 5. The crystal precipitated was filtered, washed with cold water and hexane, and dried to obtain 1.06 g (yield: 80%) of 6-cyclopentyloxynicotinic acid.

$^1$H-NMR ($CDCl_3$, TMS) δ ppm: 1.60-2.05 (8H, m), 5.47-5.53 (1H, m), 6.73 (1H, d), 8.17 (1H, dd), 8.91 (1H, d)

Intermediate Production Example 2

Production of the Intermediate Compound A-3

To 30 ml of N,N-dimethylformamide, 1.00 g (6.4 mmol) of 6-chloronicotinic acid and 2.00 g (20 mmol) of cyclohexanol were dissolved, followed by adding 0.80 g (20 mmol) of 60% sodium hydride, stirring at room temperature for 1 hour and heating under refluxing for 3 hours. The reaction liquid was then poured in 100 ml of ice water, and acetic acid was added to make pH 5. The crystal precipitated was filtered, washed with cold water and hexane, and dried to obtain 1.30 g (yield: 92%) of 6-cyclohexyloxynicotinic acid.

$^1$H-NMR ($CDCl_3$, TMS) δ ppm: 1.26-1.62 (6H, m), 1.77-1.83 (2H, m), 1.99-2.05 (2H, m), 5.11-5.19 (1H, m), 6.73 (1H, d), 8.17 (1H, dd), 8.88 (1H, d)

Intermediate Production Example 3

Production of the Intermediate Compound A-6

To 70 ml of N,N-dimethylformamide, 3.00 g (19 mmol) of 6-chloronicotinic acid and 2.00 g (29 mmol) of 2-butyne-1-ol were dissolved, followed by adding 1.80 g (45 mmol) of 60% sodium hydride, stirring at room temperature for 1 hour and stirring at 140° C. for 3 hours. The reaction liquid was then poured in 150 ml of ice water, and acetic acid was added to make pH 5, followed by adding 50 ml of a saturated saline solution. The crystal precipitated was filtered, washed with cold water and hexane and dried to obtain 0.96 g (yield: 26%) of 6-(2-butynyloxy)nicotinic acid.

$^1$H-NMR ($CDCl_3$, TMS) δ ppm: 1.89 (3H, t), 5.02 (2H, q), 6.85 (1H, d), 8.21 (1H, dd), 8.91 (1H, d)

Next, some specific examples of intermediate compounds shown by the general formula [A] are shown below with compound numbers thereof.

A-1) 6-cyclobutyloxynicotinic acid

A-2) 6-cyclopentyloxynicotinic acid

A-3) 6-cyclohexyloxynicotinic acid

A-4) 6-cycloheptyloxynicotinic acid

A-5) 6-(2-propynyloxy)nicotinic acid

A-6) 6-(2-butynyloxy)nicotinic acid

A-7) 6-(2-pentynyloxy)nicotinic acid

Next, an intermediate compound shown by the general formula [B] can be produced in accordance with the production method shown below.

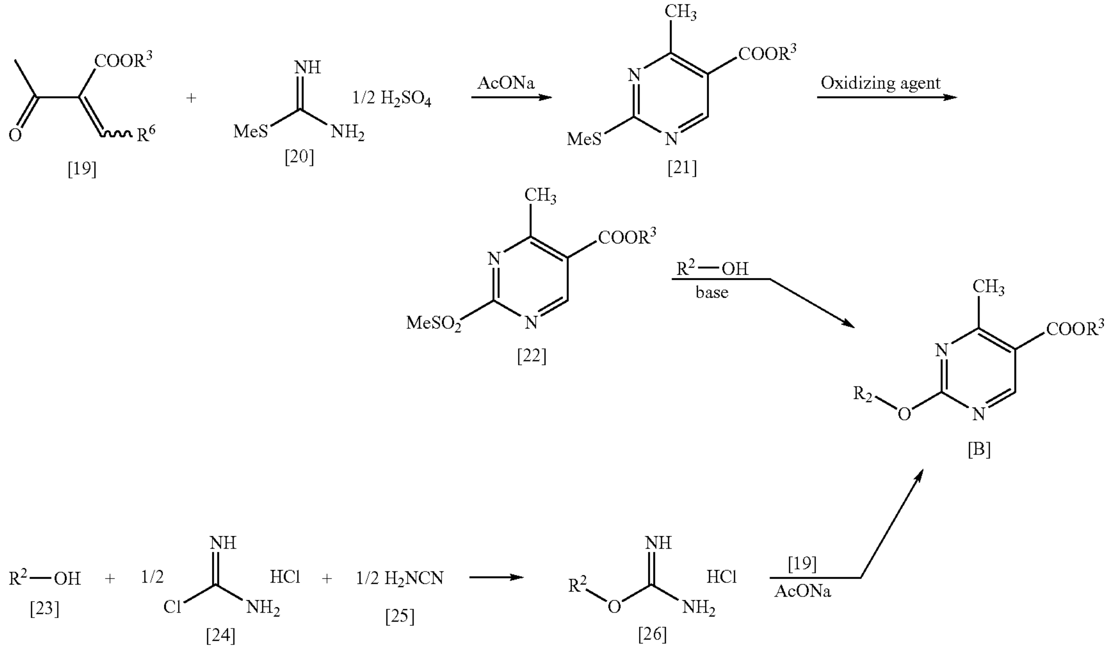

[19] [20] [21] [22] [B] [23] [24] [25] [26]

(wherein $R^2$ and $R^3$ represent the same meaning described above. $R^6$ represents a methoxy group, an ethoxy group or a dimethylamino group. An oxidizing agent includes similar one to that used in Production method 9. Abase includes a similar one, for example, used in the production method 2.) Compounds [20], [23] and [25] can be available as commercial products. A compound [19] can be synthesized by the method described in, for example, "J. Org. Chem.", page 140 (1984). A compound [24] can be synthesized by the method described in, for example, "Chem. Ber.", page 3016 (1961).

Next, Production Examples of intermediate compounds shown by [B] are shown.

Intermediate Production Example 4

Production of the Intermediate Compound B-4

(1) To 100 ml of N,N-dimethylformamide, 18.6 g (100 mmol) of ethyl 2-acetyl-3-ethoxyacrylate, 13.9 g (50 mmol) of sulfuric acid methylisothiourea and 8.2 g (100 mmol) of sodium acetate were suspended, followed by stirring at 80° C. for 4 hours. The reaction liquid was cooled and then poured in ice water. The crystal precipitated was filtered, washed with water and dried to obtain 18.6 g (yield: 88%) of ethyl 4-methyl-2-(methylthio)pyrimidine-5-carboxylate.

$^1$H-NMR ($CDCl_3$, TMS) δ ppm: 1.40 (3H, t), 2.60 (3H, s), 2.77 (3H, s), 4.38 (2H, q), 8.94 (1H, s)

(2) To 80 ml of acetic acid, 21.2 g (100 mmol) of ethyl 4-methyl-2-(methylthio)pyrimidine-5-carboxylate and 1.65 g (5.0 mmol) of sodium tungstate dihydrate were suspended, followed by slow drop-wise addition of 21.0 g (210 mmol) of a 34.5% hydrogen peroxide aqueous solution, while maintaining temperature at about 30° C. After the end of drop-wise addition, the solution was stirred at 30° C. for 30 minutes. The reaction liquid was dissolved in 300 ml of ethyl acetate, and the organic layer was washed with water, a saturated aqueous solution of sodium hydrogencarbonate and a saturated saline solution in this order, followed by adding 300 ml of hexane, drying over anhydrous magnesium sulfate, adding "Florisil" and filtering. The solution was concentrated at 40° C. under reduced pressure to obtain 10.0 g (yield: 41%) of ethyl 2-methanesulfonyl-4-methylpyrimidine-5-carboxylate.

$^1$H-NMR ($CDCl_3$, TMS) δ ppm: 1.45 (3H, t), 2.96 (3H, s), 3.39 (3H, s), 4.47 (2H, q), 9.27 (1H, s)

(3) To 13.4 g (105 mmol) of butanol was dissolved 12.8 g (52 mmol) of ethyl 2-methanesulfonyl-4-methylpyrimidine-5-carboxylate, followed by drop-wisely adding 5.82 g (58 mmol) of triethylamine under ice-cooling. After completing the drop-wise addition, the solution was stirred at room temperature for 15 hours. The reaction liquid was concentrated, and then added with 500 ml of diisopropyl ether, followed by filtering with celite. The filtrate was washed with water and a saturated saline solution in this order, followed by drying over anhydrous magnesium sulfate, adding "Florisil" and filtering. The solution was concentrated under reduced pressure to obtain 7.60 g (yield: 68%) of ethyl 2-butoxy-4-methylpyrimidine-5-carboxylate.

$^1$H-NMR ($CDCl_3$, TMS) δ ppm: 0.97 (3H, t), 1.40 (3H, t), 1.44-1.57 (2H, m), 1.76-1.85 (2H, m), 2.77 (3H, s), 4.37 (2H, q), 4.42 (2H, t), 8.98 (1H, s)

Intermediate Production Example 5

Production of the Intermediate Compound B-3

In accordance with the method described in Intermediate Production Example 4, methyl 2-butoxy-4-methylpyrimidine-5-carboxylate was obtained.

$^1$H-NMR ($CDCl_3$, TMS) δ ppm: 0.97 (3H, t), 1.44-1.57 (2H, m), 1.76-1.85 (2H, m), 2.77 (3H, s), 3.91 (3H, s),4.42 (2H, t), 8.98 (1H, s)

Intermediate Production Example 6

Production of the Intermediate Compound B-4

To 222 g (3.0 mol) of butanol, 21.0 g (0.50 mol) of cyanamide and 57.5 g (0.50 mol) of carbamimidoyl chloride hydrochloric acid salt were dissolved, followed by stirring at 60° C. for 1 hour. The reaction liquid was concentrated to obtain 2-butylisourea hydrochloric acid salt. To 500 ml of N,N-dimethylformamide, 2-butylisourea hydrochloric acid salt obtained, 186 g (1.0 mol) of ethyl 2-acetyl-3-ethoxy-acrylate and 82.0 g (1.0 mol) of sodium acetate were suspended, followed by stirring at 100° C. for 4 hours. The reaction liquid was cooled and then poured in ice-water, and extracted with diisopropyl ether. The organic layer was washed with water and a saturated saline solution in this order, followed by drying over anhydrous magnesium sulfate, adding "Florisil" and filtering. The solution was concentrated under reduced pressure to obtain 192 g (yield: 81%) of ethyl 2-butoxy-4-methylpyrimidine-5-carboxylate.

Next, some specific examples of intermediate compounds shown by the general formula [B] are shown below with compound numbers thereof.

B-1) ethyl 2-ethoxy-4-methylpyrimidine-5-carboxylate

B-2) ethyl 4-methyl-2-propoxypyrimidine-5-carboxylate

B-3) methyl 2-butoxy-4-methylpyrimidine-5-carboxylate

B-4) ethyl 2-butoxy-4-methylpyrimidine-5-carboxylate

B-5) benzyl 2-butoxy-4-methylpyrimidine-5-carboxylate

B-6) ethyl 4-methyl-2-pentyloxypyrimidine-5-carboxylate

B-7) ethyl 2-hexyloxy-4-methylpyrimidine-5-carboxylate

B-8) ethyl 2-cyclopentyloxy-4-methylpyrimidine-5-carboxylate

B-9) ethyl 2-cyclohexyloxy-4-methylpyrimidine-5-carboxylate

B-10) ethyl 2-(4-chlorobutoxy)-4-methylpyrimidine-5-carboxylate

B-11) ethyl 2-(2-methoxyethoxy)-4-methylpyrimidine-5-carboxylate

B-12) ethyl 4-methyl-2-propenyloxypyrimidine-5-carboxylate

B-13) ethyl 2-(3,3-dichloro-2-propenyloxy)-4-methylpyrimidine-5-carboxylate

B-14) ethyl 2-(2-butynyloxy)-4-methylpyrimidine-5-carboxylate

B-15) ethyl 2-cyclopropylmethoxy-4-methylpyrimidine-5-carboxylate

B-16) ethyl 4-methyl-2-phenoxypyrimidine-5-carboxylate

B-17) ethyl 2-benzyloxy-4-methylpyrimidine-5-carboxylate

B-18) ethyl 4-methyl-2-(3-pyridyloxy)pyrimidine-5-carboxylate

Next, an intermediate compound shown by the general formula [C] can be produced in accordance with the production method shown below.

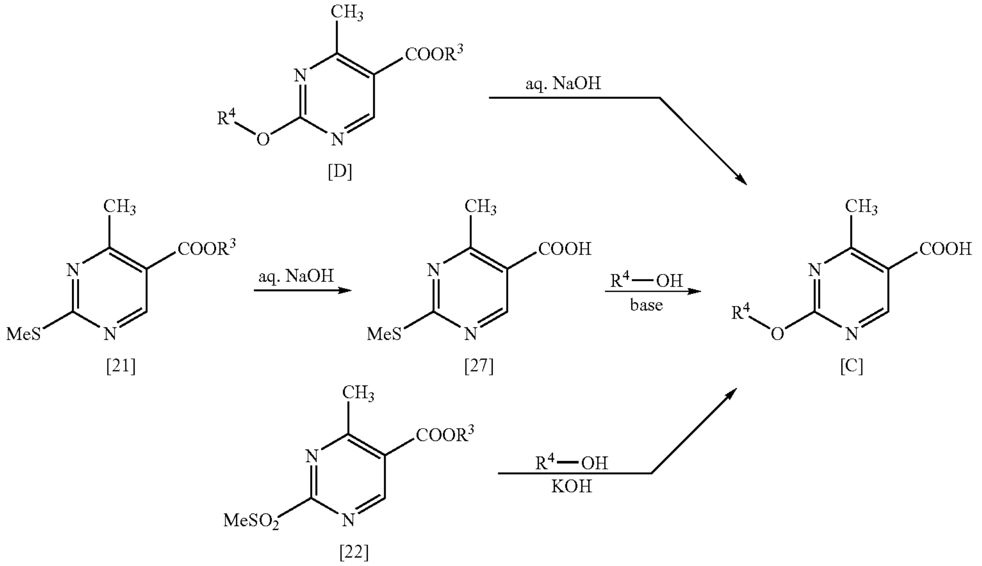

[D] [21] [27] [C] [22]

(wherein $R^3$ and $R^4$ represent the same meaning described above. A base includes the similar one, for example, used in the production method 2.) A compound [D] can be produced in accordance with the production method for an intermediate compounds shown by the general formula [B].

Next, Production Examples of intermediate compounds shown by [C] are shown.

Intermediate Production Example 7

Production of the Intermediate Compound C-4

To 50 ml of acetone, 10.0 g (42 mmol) of ethyl 2-butoxy-4-methylpyrimidine-5-carboxylate was dissolved, followed by adding 50 ml of water, then adding drop-wise 13.4 g (84 mmol) of a 25% sodium hydroxide aqueous solution, and stirring at room temperature for 1 hour. The reaction liquid was concentrated at 40° C. under reduced pressure to remove acetone, and 10% hydrochloric acid was added to make acidic. The crystal precipitated was filtered, washed with water and dried to obtain 8.00 g (yield: 91%) of 2-butoxy-4-methylpyrimidine-5-carboxylic acid.

$^1$H-NMR ($CDCl_3$, TMS) δ ppm: 0.97 (3H, t), 1.44-1.56 (2H, m), 1.75-1.85(2H, m), 2.77 (3H, s), 4.41 (2H, t), 9.00 (1H, s)

Intermediate Production Example 8

Production of the Intermediate Compound C-6

(1) To 180 ml of ethanol, 18.6 g (88 mmol) of ethyl 4-methyl-(2-methylthio) pyrimidine-5-carboxylate was dissolved, followed by the adding drop-wise, under ice cooling, 28.2 g (176 mmol) of a 25% sodium hydroxide aqueous solution. After the end of the drop-wise addition, the solution was stirred at room temperature for 2 hours. Ethanol was removed and the residue was dissolved in 200 ml of water, followed by adding 10% hydrochloric acid to make acidic. The crystal precipitated was filtered, washed with water and dried to obtain 15.6 g (yield: 96%) of 4-methyl-(2-methylthio)pyrimidine-5-carboxylic acid.

$^1$H-NMR ($CDCl_3$, TMS) δ ppm: 2.60 (3H, s), 2.77 (3H, s), 8.97 (1H, s)

(2) To 10 ml of N,N-dimethylformamide, 1.00 g (5.4 mmol) of 4-methyl-(2-methylthio)pyrimidine-5-carboxylic acid and 1.10 g (11 mmol) of hexanol were dissolved, followed by adding, under ice-cooling, 0.60 g (15 mmol) of 60% sodium hydride. After foaming ceased, the solution was stirred at 70° C. for 2 hours. To the reaction liquid 30 ml of water was added, and the water layer was washed with diisopropyl ether, followed by adding 10% hydrochloric acid to make acidic. The crystal precipitated was filtered, washed with water and dried to obtain 1.10 g (yield: 85%) of 2-hexyloxy-4-methylpyrimidine-5-carboxylic acid.

$^1$H-NMR ($CDCl_3$, TMS) δ ppm: 0.90 (3H, t), 1.28-1.42 (4H, m), 1.46-1.52(2H, m), 1.79-1.87 (2H, m), 2.82 (3H, s),4.45 (2H, t), 9.11 (1H, s)

Intermediate Production Example 9

Production of the Intermediate Compound C-9

To 16 ml of N,N-dimethylformamide, 3.00 g (16 mmol) of 4-methyl-(2-methylthio)pyrimidine-5-carboxylic acid and 2.10 g (24 mmol) of cyclopentanol were dissolved, followed by adding 1.30 g (33 mmol) of 60% sodium hydride under ice-cooling. After foaming ceased, the solution was stirred at 70° C. for 6 hours. To the reaction liquid, 60 ml of water was added, and the water layer was washed with a mixed solvent of diisopropyl ether and hexane (1:1), followed by adding 10% hydrochloric acid to make acidic, and extracting with ethyl acetate. The organic layer was washed with water and a saturated saline solution in this order and dried over anhydrous magnesium sulfate. The solution was concentrated under reduce pressure to obtain 2.90 g (yield: 80%) of 2-cyclopentyloxy-4-methylpyrimidine-5-carboxylic acid.

$^1$H-NMR ($CDCl_3$, TMS) δ ppm: 1.61-2.05 (8H, m), 2.80 (3H, s), 5.50-5.55 (1H, m), 9.09 (1H, s)

By the similar procedure, intermediate compounds C-3, C-5, C-8 and C-10 were synthesized.

Intermediate Production Example 10

Production of the Intermediate Compound C-4

To 1.5 ml of butanol, 0.72 g (11 mmol) of 85.5% potassium hydroxide powder was suspended, followed by drop-wise adding, under ice-cooling, a 1.5 ml of butanol solution dissolving with 1.22 g (5.0 mmol) of ethyl 2-methansulfonyl-4-methylpyrimidine-5-carboxylate. After the end of the drop-wise addition, the solution was stirred at room temperature for 3 hours. To the reaction liquid, 50 ml of water was added, and the water layer was washed with diisopropyl ether, followed by adding 10% hydrochloric acid to make acidic, and extracting with ethyl acetate. The organic layer was washed with water and a saturated saline solution in this order, and dried over anhydrous magnesium sulfate. The solution was concentrated under reduced pressure to obtain 0.87 g (yield: 83%) of 2-butoxy-4-methylpyrimidine-5-carboxylic acid.

Next, some specific examples of intermediate compounds shown by the general formula [C] are shown below with compound numbers.

C-1) 2-methoxy-4-methylpyrimidine-5-carboxylic acid

C-2) 2-ethoxy-4-methylpyrimidine-5-carboxylic acid

C-3) 4-methyl-2-propoxypyrimidine-5-carboxylic acid

C-4) 2-butoxy-4-methylpyrimidine-5-carboxylic acid

C-5) 4-methyl-2-pentyloxypyrimidine-5-carboxylic acid

C-6) 2-hexyloxy-4-methylpyrimidine-5-carboxylic acid

C-7) 2-heptyloxy-4-methylpyrimidine-5-carboxylic acid

C-8) 4-methyl-2-octyloxypyrimidine-5-carboxylic acid

C-9) 2-cyclopentyloxy-4-methylpyrimidine-5-carboxylic acid

C-10) 2-cyclohexyloxy-4-methylpyrimidine-5-carboxylic acid

C-11) 2-(4-chlorobutoxy)-4-methylpyrimidine-5-carboxylic acid

C-12) 2-(2-methoxyethoxy)-4-methylpyrimidine-5-carboxylic acid

C-13) 4-methyl-2-propenyloxypyrimidine-5-carboxylic acid

C-14) 2-(3,3-dichloro-2-propenyloxy)-4-methylpyrimidine-5-carboxy lic acid

C-15) 2-(2-butynyloxy)-4-methylpyrimidine-5-carboxylic acid

C-16) 2-cyclopropylmethoxy-4-methylpyrimidine-5-carboxylic acid

C-17) 4-methyl-2-phenoxypyrimidine-5-carboxylic acid

C-18) 2-benzyloxy-4-methylpyrimidine-5-carboxylic acid

C-19) 4-methyl-2-(3-pyridyloxy)pyrimidine-5-carboxylic acid

Next, Production Examples of an intermediate compound shown by the general formula [2] are shown below.

Intermediate Production Example 11

Production of the Intermediate Compound 1

(1) To 400 ml of tetrahydrofuran in a reactor, 15.0 g (0.17 mol) of 3-oxo-1-butanol and 26.3 g (0.19 mol) of benzoyl chloride were dissolved, followed by drop-wise adding 20.6 g (0.20 mol) of triethylamine under ice-cooling. After the end of drop-wise addition, the reaction liquid was stirred at room temperature for 3 hours. Hydrochloric acid salt of triethylamine was filtered, followed by adding water to the filtrate and extracting with ethyl acetate. The organic layer was washed with water, a saturated aqueous solution of sodium carbonate, water and a saturated saline solution in this order, followed by drying over anhydrous magnesium sulfate and concentrating under reduced pressure. The residue was purified with silica gel column chromatography (ethyl acetate:hexane=1:5 to 1:3) to obtain 31.5 g (yield: 96%) of 3-oxobutylbenzoate.

$^1$H-NMR ($CDCl_3$, TMS) δ ppm: 2.24 (3H, s), 2.91 (2H, t), 4.59 (2H, t), 7.44 (2H, t), 7.56 (1H, t), 8.01 (2H, d)

(2) Reaction was carried out under nitrogen atmosphere. To 400 ml of tetrahydrofuran, 46.2 g (0.22 mol) of dibromodifluoromethane was dissolved, followed by drop-wise adding 70.2 g (0.43 mol) of tris (dimethylamino)phosphine at −10° C. After the end of the drop-wise addition, the reaction liquid was stirred at room temperature for 1 hour, and 150 ml tetrahydrofuran solution dissolving with 19.2 g (0.10 mol) of 3-oxobutylbenzoate was further added drop-wise at −20° C. After the end of the drop-wise addition, the reaction liquid was stirred at room temperature overnight. To this mixture, diethyl ether was added, followed by washing with dilute hydrochloric acid, a saturated aqueous solution of sodium hydrogencarbonate and a saturated saline solution in this order, followed by drying over anhydrous magnesium sulfate, and concentrating under reduced pressure. The residue was purified by silica gel column chromatography (diisopropyl ether:hexane=1:8) to obtain 16.4 g (yield: 72%) of 4,4-difluoro-3-methyl-3-butenyl benzoate.

$^1$H-NMR ($CDCl_3$, TMS) δ ppm: 1.67 (3H, t), 2.42-2.47 (2H, m), 4.38 (2H, t), 7.45 (2H, t), 7.57 (1H, t), 8.03 (2H, d)

(3) To a mixture consisting of 16.1 g (71 mmol) of 4,4-difluoro-3-methyl-3-butenyl benzoate, 30 ml of water and 100 ml of methanol, 7.4 g (93 mmol) of a 50% sodium hydroxide aqueous solution was added, followed by stirring at 60° C. for 3 hours. The reaction liquid was then cooled to room temperature, followed by adding water and extracting with diethyl ether. The organic layer was washed with an aqueous solution of sodium hydroxide, water and a saturated saline solution in this order, followed by drying over anhydrous magnesium sulfate and concentrating under reduced pressure to obtain 7.5 g (yield: 86%) of 4,4-difluoro-3-methyl-3-butenol.

$^1$H-NMR ($CDCl_3$, TMS) δ ppm: 1.38 (1H, t), 1.61 (3H, t), 2.21-2.27 (2H, m), 3.71 (2H, q)

(4) To 100 ml of tetrahydrofuran, 4.45 g (36 mmol) of 4,4-difluoro-3-methyl-3-butenol and 4.59 g (40 mmol) of methanesulfonyl chloride were dissolved, followed by drop-wisely adding 4.42 g (44 mmol) of triethylamine under ice-cooling. After the end of the drop-wise addition, the reaction liquid was stirred at room temperature for 1 hour. Hydrochloric acid salt of triethylamine was filtered, followed by adding water to the filtrate and extracting with ethyl acetate. The organic layer was washed with water and a saturated saline solution in this order, followed by drying over anhydrous magnesium sulfate and concentrating under reduced pressure to obtain 7.20 g (yield: 99%) of 4,4-difluoro-3-methyl-3-butenyl methanesulfonate.

$^1$H-NMR ($CDCl_3$, TMS) δ ppm: 1.64 (3H, t), 2.40-2.46 (2H, m), 3.02 (3H, s), 4.27 (2H, t)

Intermediate Production Example 12

Production of the Intermediate Compound 5

(1) To 110 ml of tetrahydrofuran, 53 g (0.30 mol) of methyl 6,6-difluoro-5-methyl-5-hexenoate was dissolved, followed by adding 23 g (0.61 mmol) of sodium borohydride, heating the mixture under refluxing and slowly drop-wisely adding 50 ml of methanol. After the end of the drop-wise addition, the reaction liquid was stirred under refluxing for 1 hour, followed by cooling to room temperature, adding water and extracting with diethyl ether. The organic layer was washed with water, dilute hydrochloric acid and a saturated saline solution in this order, followed by drying over anhydrous magnesium sulfate, and concentrating under reduced pressure to obtain 36.5 g (yield: 82%) of 6,6-difluoro-5-methyl-5-hexenol.

$^1$H-NMR ($CDCl_3$, TMS) δ ppm: 1.43-1.61(7H, m), 1.98-2.03 (2H, m), 3.66 (2H, t)

(2) To 100 ml of tetrahydrofuran, 5.00 g (33 mmol) of methyl 6,6-difluoro-5-methyl-5-hexenol and 4.20 g (37 mmol) of methanesulfonyl chloride were dissolved, followed by drop-wisely adding 4.40 g (44 mmol) of triethylamine under ice-cooling. After the end of the drop-wise addition, the reaction liquid was stirred at room temperature for 1 hour. Hydrochloric acid salt of triethylamine was filtered, followed by adding water to the filtrate and extracting with ethyl acetate. The organic layer was washed with water and a saturated saline solution in this order, followed by drying over anhydrous magnesium sulfate and concentrating under reduced pressure to obtain 7.50 g (yield: 99%) of 6,6-difluoro-5-methyl-5-hexenyl methanesulfonate.

$^1$H-NMR ($CDCl_3$, TMS) δ ppm: 1.50-1.60 (5H, m), 1.70-1.79 (2H, m), 1.99-2.05(2H, m), 3.01 (3H, s), 4.24 (2H, t)

Intermediate Production Example 13

Production of the Intermediate Compound 7

(1) 7,7-Difluoro-6-methyl-6-heptenol was obtained in accordance with the method described in Intermediate Production Example 12-(1).

$^1$H-NMR ($CDCl_3$, TMS) δ ppm: 1.29-1.48(5H, m), 1.52-1.63 (5H, m), 1.94-2.00(2H, m), 3.65 (2H, q)

(2) 7,7-Difluoro-6-methyl-6-heptenyl methanesulfonate was obtained in accordance with the method described in Intermediate Production Example 12-(2).

$^1$H-NMR ($CDCl_3$, TMS) δ ppm: 1.35-1.48 (4H, m), 1.55 (3H, t), 1.72-1.81 (2H, m), 1.95-2.01 (2H, m), 3.01 (3H, s), 4.23 (2H, t)

Intermediate Production Example 14

Production of the Intermediate Compound 9

(1) 8,8-Difluoro-7-methyl-7-octenol was obtained in accordance with the method described in Intermediate Production Example 12-(1).

$^1$H-NMR ($CDCl_3$, TMS) δ ppm: 1.24-1.45 (7H, m), 1.53-1.62 (5H, m), 1.93-1.98 (2H, m), 3.65 (2H, t)

(2) 8,8-Difluoro-7-methyl-7-octenyl methanesulfonate was obtained in accordance with the method described in Intermediate Production Example 12-(2).

$^1$H-NMR ($CDCl_3$, TMS) δ ppm: 1.28-1.47 (6H, m), 1.55 (3H, t), 1.71-1.80 (2H, m), 1.92-1.98 (2H, m), 3.01 (3H, s), 4.23 (2H, t)

Next, some specific examples of intermediate compounds shown by the general formula [2] are shown below with compound numbers thereof.

1) 4,4-difluoro-3-methyl-3-butenyl methanesulfonate 2) 4,4-difluoro-3-methyl-3-butenyl ethanesulfonate 3) 5,5-difluoro-4-methyl-4-pentenyl methanesulfonate 4) 5,5-difluoro-4-methyl-4-pentenyl ethanesulfonate 5) 6,6-difluoro-5-methyl-5-hexenyl methanesulfonate 6) 6,6-difluoro-5-methyl-5-hexenyl ethanesulfonate 7) 7,7-difluoro-6-methyl-6-heptenyl methanesulfonate 8) 7,7-difluoro-6-methyl-6-heptenyl ethanesulfonate 9) 8,8-difluoro-7-methyl-7-octenyl methanesulfonate 10) 8,8-difluoro-7-methyl-7-octenyl ethanesulfonate 11) 10,10-difluoro-9-methyl-9-decenyl methanesulfonate 12) 10,10-difluoro-9-methyl-9-decenyl ethanesulfonate Next, Production Examples of an intermediate compound shown by the general formula [3] are shown below.

Intermediate Production Example 15

Production of the Intermediate Compound 13

(1) To 80 ml of N,N-dimethylformamide, 25 g (0.19 mol) of 5-oxohexanoic acid and 43 g (0.31 mol) of potassium carbonate were dissolved and heated at 50° C., followed by drop-wisely adding 41 g (0.29 mol) of methyl iodide and stirring at the same temperature for 2 hours. To this mixture, 150 ml of water was added, followed by extracting with diethyl ether (200 ml×4). The organic layer was washed with a saturated saline solution, followed by drying over anhydrous magnesium sulfate and concentrating under reduced pressure to obtain 24.9 g (yield: 90%) of methyl 5-oxohexanoate.

$^1$H-NMR ($CDCl_3$, TMS) δ ppm: 1.85-1.94 (2H, m), 2.15 (3H, s), 2.35 (2H, t), 2.51 (2H, t), 3.67 (3H, s)

(2) Reaction was carried out under nitrogen atmosphere. To 650 ml of tetrahydrofuran, 80 g (0.38 mol) of dibromodifluoromethane was dissolved, followed by drop-wisely adding 121 g (0.74 mol) of tris(dimethylamino)phosphine at −10° C. After the end of the drop-wise addition, the reaction liquid was stirred at room temperature for 1 hour, followed by further drop-wisely adding 24.9 g (0.17 mol) of methyl 5-oxohexanoate dissolved in 250 ml of tetrahydrofuran, at −20° C. After the end of the drop-wise addition, the reaction liquid was stirred at room temperature overnight. To this mixture, diethyl ether was added, followed by washing with dilute hydrochloric acid, a saturated aqueous solution of sodium hydrogencarbonate and a saturated saline solution in this order, followed by drying over anhydrous magnesium sulfate and concentrating under reduced pressure. The residue was purified by silica gel column chromatography (diethyl ether:hexane=1:4) to obtain 27 g (yield: 88%) of methyl 6,6-difluoro-5-methyl-5-hexenoate.

$^1$H-NMR ($CDCl_3$, TMS) δ ppm: 1.56 (3H, t), 1.69-1.79 (2H, m), 1.98-2.04 (2H, m), 2.30 (2H, t), 3.68 (3H, s)

Intermediate Production Example 16

Production of the Intermediate Compound 15

Methyl 7,7-difluoro-6-methyl-6-heptenoate was obtained in accordance with the method described in Intermediate Production Example 15.

$^1$H-NMR ($CDCl_3$, TMS) δ ppm: 1.38-1.48 (2H, m), 1.55 (3H, t), 1.56-1.66 (2H, m), 1.95-2.01 (2H, m), 2.33 (2H, t), 3.67 (3H, s)

Intermediate Production Example 17

Production of the Intermediate Compound 17

Methyl 8,8-difluoro-7-methyl-7-octenoate was obtained in accordance with the method described in Intermediate Production Example 15.

$^1$H-NMR ($CDCl_3$, TMS) δ ppm: 1.26-1.46 (4H, m), 1.54 (3H, t), 1.59-1.69 (2H, m), 1.93-1.99 (2H, m), 2.31 (2H, t), 3.67 (3H, s)

Next, some specific examples of intermediate compounds shown by the general formula [3] are shown below with compound numbers thereof.

13) methyl 6,6-difluoro-5-methyl-5-hexenoate 14) ethyl 6,6-difluoro-5-methyl-5-hexenoate 15) methyl 7,7-difluoro-6-methyl-6-heptenoate 16) ethyl 7,7-difluoro-6-methyl-6-heptenoate 17) methyl 8,8-difluoro-7-methyl-7-octenoate 18) ethyl 8,8-difluoro-7-methyl-7-octenoate 19) methyl 10,10-difluoro-9-methyl-9-decenoate 20) ethyl 10,10-difluoro-9-methyl-9-decenoate Next, Production Examples of an intermediate compound shown by the general formula [4] are shown below.

Intermediate Production Example 18

Production of the Intermediate Compound 25

To 100 ml of N,N-dimethylformamide, 4.56 g (20 mmol) of 6,6-difluoro-5-methyl-5-hexenyl methanesulfonate and 4.70 g (26 mmol) of sodium dimethyldithiocarbamate dihydrate were dissolved, followed by stirring at 100° C. for 3 hours. The reaction liquid was poured into water and extracted with ethyl acetate. The organic layer was washed with water and a saturated saline solution in this order, followed by drying over anhydrous magnesium sulfate and concentrating under reduced pressure. The residue was purified by silica gel column chromatography (ethyl acetate: hexane=1:10) to obtain 2.60 g (yield: 51%) of 6,6-difluoro-5-methyl-5-hexenyl N,N-dimethyldithiocarbamate.

$^1$H-NMR ($CDCl_3$, TMS) δ ppm: 1.48-1.58 (5H, m), 1.64-1.74 (2H, m), 1.97-2.04 (2H, m), 3.29 (2H, t), 3.37 (3H, s), 3.56 (3H, s)

Intermediate Production Example 19

Production of the Intermediate Compound 26

6,6-Difluoro-5-methyl-5-hexenyl N,N-diethyldithio-carbamate was obtained in accordance with the method described in Intermediate Production Example 18.

$^1$H-NMR ($CDCl_3$, TMS) δ ppm: 1.25-1.31 (6H, m), 1.48-1.58 (5H, m), 1.64-1.74 (2H, m), 1.97-2.03 (2H, m), 3.29 (2H, t), 3.75 (2H, q), 4.04 (2H, q)

Next, some specific examples of intermediate compounds shown by the general formula [4] are shown below with compound numbers thereof.

21) 4,4-difluoro-3-methyl-3-butenyl N,N-dimethyldithiocarbamate 22) 4,4-difluoro-3-methyl-3-butenyl N,N-diethyldithio-carbamate 23) 5,5-difluoro-4-methyl-4-pentenyl N,N-dimethyldithiocarbamate 24) 5,5-difluoro-4-methyl-4-pentenyl N,N-diethyldithiocarbamate 25) 6,6-difluoro-5-methyl-5-hexenyl N,N-dimethyldithiocarbamate 26) 6,6-difluoro-5-methyl-3-hexenyl N,N-diethyldithio-carbamate 27) 7,7-difluoro-6-methyl-6-heptenyl N,N-dimethyldithiocarbamate 28) 7,7-difluoro-6-methyl-6-heptenyl N,N-diethyldithiocarbamate 29) 8,8-difluoro-7-methyl-7-octenyl N,N-dimethyldithiocarbamate 30) 8,8-difluoro-7-methyl-7-octenyl N,N-diethyldithio-carbamate 31) 10,10-difluoro-9-methyl-9-octenyl N,N-dimethyldithiocarbamate 32) 10,10-difluoro-9-methyl-9-octenyl N,N-diethyldithiocarbamate In using a compound of the present invention as an effective ingredient for a pest control agent, a compound of the present invention may be used as it is, but it can be transformed into various types of formulations such as emulsion, suspension, powder formulation, granule, tablet, wettable powder, water soluble powder, liquid drug, flowable type pesticide, granule type wettable powder, aerosol, paste, oil solution, opacifier, smoking agent, or the like, by compounding a carrier, a surfactant and other auxiliary agents generally used in a preparation as a pesticide auxiliary agent. Compounding ratio of these agents is, in general, 0.1 to 90 parts by weight as an effective ingredient and 10 to 99.9 parts by weight as a pesticide auxiliary agent.

A carrier used in preparation here is classified into a solid carrier and a liquid carrier. A solid carrier includes, for example, powders derived from animals or plants such as starch, activated carbon, soybean powder, wheat flour, wood flour, fish meal and dried milk, and inorganic powders such as talc, kaolin, bentonite, calcium carbonate, zeolite, diatomaceous earth, white carbon, clay, alumina, ammonium sulfate and urea. A liquid carrier includes, for example, water; alcohols such as isopropyl alcohol and ethylene glycol; ketones such as cyclohexanone and methyl ethyl ketone; ethers such as dioxane and tetrahydrofuran; aliphatic hydrocarbons such as kerosene and gas oil; aromatic hydrocarbons such as xylene, trimethylbenzene, tetramethylbenzene, methylnaphthalene and solvent naphtha; halogenated hydrocarbons such as chlorobenzene; amides such as dimethylacetamide; esters such as glycerin esters of aliphatic acids; nitriles such as acetonitrile; and sulfur containing compounds such as dimethylsulfoxide.

A surfactant includes, for example, metal alkylbenzenesulfonates, metal dinaphthylmethanesulfonates, alcohol sulfate salts, alkylarylsulfonate salts, ligninsulfonate salts, polyoxyethylene glycol ethers, polyoxyethylene alkylaryl ethers, polyoxyethylene solbitanmonoalkylates and silicone based surfactants.

Other auxiliary agent which can be used includes adhesives or thickeners such as carboxymethyl cellulose, gum Arabic, sodium alginate, guar gum, tragacanth gum, polyvinylalcohol or the like; defoaming agents such as metal soap; property improving agents such as aliphatic acids, alkylphosphate salts, silicone and paraffin; colorants; and the like.

In practical use of these preparation, they may be used as they are or by diluting with a diluent such as water or the like to a specific concentration. Various preparations containing a compound of the present invention or diluted form thereof may be applied by generally adopted processes, that is, spraying (for example, atomization, misting, dusting, granule spraying, water surface scattering and application in a box), soil application (for example and mixing, irrigation), surface application (for example, coating, powder spraying and covering), dipping, poison bait, smoking, or the like. It can also be fed by mixing the above-described effective ingredient into feed for domestic animals to inhibit generation and growth of vermin, in particular, noxious insects in the excreta. It may also be applicable by small amount of spraying in ultra-high concentration. In this method, 100% of active ingredient can be included. Compounding ratio of an effective ingredient is suitably selected as appropriate, but 0.1 to 20% (by weight) is suitable for powder and granule preparation, and 1 to 80% (by weight) is suitable for emulsion preparation and wettable powder.

The pest control agent of the present invention is used, in general, in a concentration of an active ingredient of 0.1 to 5,000 ppm, when the agent is used in diluted state with a diluent. In the case when the agent is applied without dilution, an amount of the preparation to be applied for unit area is, but not limited to, 0.1 to 5,000 g per hectare as an active ingredient compound.

It is not to be argued that the compound of the present invention demonstrate sufficient effectiveness by itself, but it can be used by mixing with or together with other fertilizers or agricultural chemicals such as insecticides, acaricides, nematicides, fungicides, antiviral agents, attractants, herbicides and plant growth regulators, and such way of use may provide further beneficial effects.

Typical examples of insecticides, fungicides and acaricides which can be used by mixing with a compound of the present invention are shown as follows.

For example, organo-phosphoric and carbamate insecticides:

For Example, Organo-phosphoric and carbamate insecticides: Fenthion, Fenitrothion, Diazinon, Chlorpyrifos, Oxydeprofos, Vamidothion, Phenthoate, Dimethoate, Formothion, Malathion, Trichlorfon, Thiometon, Phosmet, Dichlorvos, Acephate, EPBP, Methyl-parathion, Oxydemeton-methyl, Ethion, Dioxabenzofos, Cyanophos, Isoxathion, Pyridaphention, Phosalone, Methidation, Sulprofos, Chlorfenvinphos, Tetrachlorvinphos, Dimethylvinphos, Propaphos, Isofenphos, Disulfoton, Profenofos, Pyraclofos, Monocrotophos, Azinphos-methyl, Aldicarb, Methomyl, Thiodicarb, Carbofuran, Carbosulfan, Benfuracarb, Furathiocarb, Propoxur, Fenobucarb, Metolcarb, Isoprocarb, Carbaryl, Pirimicarb, Ethiofencarb, Dichlofenthion, Pirimiphos-methyl, Quinalphos, Chlorpyrifos-methyl, Prothiofos, NALED, EPN, XMC, Bendiocarb, Oxamyl, Alanycarb, Chlorethoxyfos, etc.

Pyrethroid Insecticides: Permetrin, Cypermethrin, Deltamethrin, Fenvalerate, Fenpropathrin, Pyrethrins, Allethrin, Tetramethrin, Resmethrin, Dimethrin, Proparthrin, Phenothrin, Protorin, Fluvalinate, Cyfluthrin, Cyhalothrin, Flucythrinate, Etofenprox, Cycloprotorin, Tralomethrin, Silafluofen, Tefluthrin, Bienthrin, Acrinathrin etc.

Acylurea and other insecticides: Diflubenzuron, Chlorfluazuron, Hexaflumuron, Triflumuron, Teflubenzuron, Flufenoxuron, Flucycloxuron, Buprofezin, Pyriproxyfen, Lufenuron, Cyromazine, Methoprene, Endosulfan, Diafenthiuron, Imidacloprid, Acetamiprid, Nitenpyram, Clotianidin, Dinotefuran, Thiamethoxiam, Thiacloprid, Pymetrozine, Fipronil, Nicotine-sulfate, Rotenone, Metaldehyde, Pyridalyl, Chromafenozide, Spinosad, Machine Oil, Microbial Pesticide such as BT or Insect Phathogenic Virus, Fenoxycarb, Cartap, Thiocycolam, Bensul Tap, Tebufenozide, Chlorfenapyr, Emamectin, Benzoate, Acetaprid, Nitenpyram, Sodium-oleate, Rapessed Oil, etc.

Nematocides: Fenamiphos, Fosthiazate, Ethoprophos, Methyl-isothiocynate, 1,3 Dichloropropene, DCIP, Chloropicrin, D-D, MITC, Metam-sodium, Dazomet, Oxamyl etc.

Acaricides: Chlorobenzilate, Bromopropylate, Dicofol, Amitraz, Propargite, Benzomate, Hexythiazox, Fenbutatinoxide, Polynactins, Chinomethionat, Chlorfenson, Tetradifon, Abamectin, Milbemectin, Clofentezine, Phenothiocarb, Dienochlor, Etoxazole, Bifenazate, Acequinocyl, Halfenprox, etc.

Fungicides: Thiophanate-methyl, Benomyl, Carbendazim, Thiabendazole, Folpet, Thiuram, Ziram, Zineb, Maneb, Polycarbamate, Iprobenfos, Edifenphos, Fthalide, Probenazole, Isoprothiolane, Chlorothalonil, Captan, Polyoxins, Blastciden-S, Kasugamycin, Streptomycin, Validamycin, Tricyclazole, Pyroquilon, Phenazine-oxide, Mepronil, Flutolanil, Pencycuron, Iprodione, Hymexazole, Metalaxyl, Triflumizole, Triforine, Triadimefon, Bitertanol, Fenarimol, Propiconazole, Cymoxanil, Prochloraz, Pefurazoate, Hexaconazole, Myclobutanil, Diclomezine, Tecloftalam, Propineb, Dithianon, Fosetyl, Vinclozolin, Procymidone, Oxadixyl, Guazatine, Propamocarb, Fluazinam, Oxolinicacid, Hymexazol, Mepanipyrim, etc.

The compound of the present invention demonstrate an superior prevention/extermination effect against the pest insects including, for example, Hemiptera, Lepidoptera, Coleoptera, Diptera, Hymenoptera, Orthoptera, Isoptera, Thysnoptera, *Tetranychus* and plant parasitic Nematodes. The following insects can be shown as examples of such pest insect.

Hemiptera pests including, for example, Pentatomidae (Heteroptera) such as *Riptortus clavatus, Nezara viridula, Lygus* sp., *Blissus leucopterus* and *Stephanitis nashi*; Cicadalloidea such as *Nephotettix cincticeps, Empoasca* sp., *Erythroneura* sp. and *Circulifer* sp.; Fulgoroidea such as *Nilaparvata lugens, Sogatella furcifera* and *Laodelphax striatellus*; Psylloidea such as *Psylla* sp.; Aleyroidea such as *Bemisisa tabaci* and *Trialeurodes vaporariorum*; Aphidoidea such as *Viteus vitifolii, Myzus persicae, Aphis pomi, Aphis gossypii, Aphis fabae, Rhopalosiphum psedobrassicas, Aulacorthum solani* and *Schizaphis graminum*; Coccoidea such as *Pseudococcus comstocki, Ceroplastes rubens, Comstockaspis perniciosa* and *Unaspis yanonensis;*

Lepidoptera pests including, for example, Tortricidae such as *Homona magnanima, Adoxophyes orana, Sparganothis pilleriana, Grapholitha molesta, Leguminivora glycinivorella, Laspeyresia pomonella, Eucosma* sp. and *Lobesia botrana*; Cochylidae such as *Eupoecillia ambiguella;* Psychidae such as *Bambalina* sp.; Tineidae such as *Nemapogon granellus* and *Tinea translucens*; Lyonetiidae such as *Lyonetia prunifoliella*; Gracillaridae such as *Phyllonorycter rigoniella*; Phyllocnistidae such as *Phyllocnistis citrella*; Yponomeutidae such as *Plutella xylostella* and *Prays citri*; Sesiidae such as *Paranthrene regalis, Synanthedon* sp.; Gelechiidae such as *Pectinophora gossypiella, Phthorimaea operculella* and *Stomopteryx* sp.; Carposinidae such as *Carposina niponensis*; Limacodidae such as *Monema flavescens*; Pyralidae such as *Chilo suppressalis, Cnaphalocrocis medinalis, Ostrinia nubilalis, Ostrinia furnacalis, Hellula undalis, Galleria mellonella, Elasmopalpus lignosellus* and *Loxostege sticticalis*; Pieridae such as *Pieris rapae*; Geometridae such as *Ascotis selenaria*; Lasiocampidae such as *Malacosoma neustria*; Sphingidae such as *Manduca Sexta*; Lymantriidae such as *Euproctis pseudoconspersa* and *Lymantria dispar*; Arctiidae such as *Hyphantria cunea*; Noctuidae such as *Heliothis virescenes, Helicoverpa zea, Spodoptera exigua, Helicoverpa armigera, Spodoptera litura, Mamestra brassicae, Agrotis ipsiron, Pseudaletia separata* and *Trichoplusia ni;*

Coleoptera pests including, for example, Scarabaeidae such as *Anomala cuprea, Popillia japonica, Anomala rufocuprea* and *Eutheola rugiceps*; Elateridae such as *Agriotes* sp. and *Condodeus* sp.; Coccinellidae such as *Epilachna vigintioctopunctata* and *Epilachna varivestis*; Tenebrionidae such as *Tribolium castaneum*; Cerambycidae such as *Anoplophora malasiaca* and *Monochamus alternatus*; Bruchidae such as *Acanthoscelides obtectus* and *Callosobruchus chinensis*; Chrysomelidae such as *Leptinotarsa decemlineata, Diabrotica* sp., *Oulema oryzae, Chaetocnema concinna, Phaedon cochlearias, Oulema melanopus* and *Dicladispa armigera*; Apionidae such as *Apion godmani*; Curculinidae such as *Lissorhoptrus oryzophilus* and *Anthonomus grandis*; Rhynchophoridae such as *Sitophilus zeamais*, Scolytidae, Dermestidae and Anobiidae;

Diptera pests including, for example, *Tipra ano, Tanytarsus oryzae, Orseolia oryzae, Ceratitis capitata, Hydrellia griseola, Drosophila suzukii, Oscinella frit, Chlorops oryzae, Ophiomyia phaseoli, Liriomyza trifolii, Pegomya hyoscyami, Hylemia platura, Atherigona soccata, Musca domestica, Gastrophilus* sp., *Stomoxys* sp., *Aedes aegypti, Culex pipiens, Anopheles slnensis* and *Culex tritaeniorhynchus;*

Hymenoptera pests including, for example, *Cephus* sp., *Harmolita* sp., *Athalia* sp., *Vespa* sp. and Fire ants;

Orthoptera pests including, for example, *Blatella germanica, Periplaneta americana, Gryllotalpa africana, Locusta migratoria migratoriodes* and *Melanoplus sanguinipes;*

Isoptera pests including, for example, *Reticulitermes speratus* and *Coptotermes formosanus;*

Thysnoptera pests including, for example, *Scirtothrips dorsalis, Thrips palmi, Heliothrips haemorrhoidalis, Frankliniella occidentalis* and *Haplothrips aculeatus;*

Tetranychus pests including, for example, *Tetranychus urticae, Tetranychus kanzawai, Panonychus citri, Panonychus ulmi, Eotetranychus carpini, Eotetranychus banksi, Phyllocoptruta oleivora, Polyphagotarsonemus latus, Brevipalpus* sp., *Rhizoglyphus robini* and *Tyrophagus putrescentiae;*

Plant parasitic Nematodes including, for example, *Meloidogyne incognita, Pratylenchus* sp., *Heterodera glycines, Aphelenchoides besseyi* and *Bursaphelenchus xylophilus;*

Other noxious animals, awkward animals, sanitary pests and parasitic insects including, for example, Gastropoda such as *Pomacea canaliculata, Incilaria* sp. and *Achatina fulica*; Isopoda such as *Armadillidium* sp., woodlouse and centipede; Psocus such as *Liposcelis* sp.; Lepisma such as *Ctenolepisma* sp.; flea such as *Pulex* sp. and *Ctenocephalides* sp.; *Mallophaga* such as *Trichodectes* sp.; chinch such as *Cimex* sp.; animal parasitic tics such as *Boophilus microplus* and *Haemaphysalis longicornis*.

Further, the compound of the present invention is effective against the pest insects which show resistance to organo-phosphoric compounds, carbamate compounds, synthetic pyrethroid compounds, acylurea compounds, and other conventional insecticides.

Next, detailed preparation methods for typical preparations are now explained. Types and compounding ratio of a compound and auxiliary agents should not be limited to these, and wide range of alteration is possible. In the following explanation, % represents % by weight.

Preparation Example 1

Emulsion

Were homogeneously dissolved 30% of the compound (33), 20% of cyclohexane, 11% of polyoxyethylene alkylaryl ether, 4% of calcium alkylbenzenesulfonate and 35% of methylnaphthalene to obtain emulsion.

Preparation Example 2

Wettable Powder

Were homogeneously mixed and crashed 10% of the compound (33), 0.5% of sodium salt of naphthalenesulfonic acid/formalin condensate, 0.5% of polyoxyethylene alkylaryl ether, 24% of diatomaceous earth and 65% of clay to obtain wettable powder.

Preparation Example 3

Powder

Were homogeneously mixed and crashed 2% of the compound (33), 5% of diatomaceous earth and 93% of clay to obtain powder.

Preparation Example 4

Granule

Were homogeneously mixed and crashed 50% of the compound (33), 2% of sodium salt of laurylsulfate, 5% of sodium ligninsulfonate, 2% of calboxymethyl cellulose and 86% of clay. To 100 parts by weight of this mixture, 20 parts by weight of water was added, followed by mixing and pelletizing using an extruder to make pellets with a size of 14 to 32 mesh and drying to obtain granule.

Next, effects shown by the pest control agent containing a compound of the present invention as an effective ingredient are described by way of Test Examples.

Test Example 1

Insecticidal test for *Nilaparvata lugenis*

The wettable powder prepared according to the above Preparation Example 2 was diluted with water to a concentration of 500 ppm as a concentration of active ingredient. After soaking the germinated rice paddy in the test solution, the paddy was transferred into a 60 ml volume of plastic cup. Ten (10) heads of 4-instar larvae of *Nilaparvata lugenis* were inoculated on the paddy and capped, then left at the constant temperature of 25° C. After 6 days from the inoculation, the number of surviving insects was counted, and mortality rate of the insect was calculated according to the following formula 1.

$$\text{mortality rate (\%)}=[(10-\text{number of surviving insect in the test field})/10]\times 100 \quad (1)$$

In this test, representative compounds having the insecticidal effect with 90% or higher of mortality include compound No. 1, 2, 8, 9, 10, 11, 15, 16, 21, 22, 23, 25, 26, 28, 32, 33, 34, 38, 39, 40, 41, 43, 44, 45, 47, 48, 49, 50, 129, 132, 169, 234, 242, 276, 278, 281 and 282.

Test Example 2

Prevention/extermination Test Against *Tetranychus urticae*

The wettable powder prepared according to the above Preparation Example 2 was diluted with water to a concentration of 500 ppm as a concentration of active ingredient. Soybean seedlings which had previously been inoculated with the imago of *Tetranychus urticae* were soaked in the test solution, then air dried. The treated soybean seedlings were left at the constant temperature of 25° C. After 13 days from the treatment, the number of surviving mites was counted, and the prevention/extermination titer was calculated according to the formula 2 below.

In this test, representative compounds having the acaricidal effect with more than 90 of preventive titer include compound No. 7, 12, 13, 16, 27, 31, 32, 33, 35, 37, 42, 185, 194 and 203. Further, these compounds did not show any adverse effect on the soybean seedling.

Test Example 3

Prevention/Extermination Test Against *Tetranychus urticae*

The wettable powder prepared according to the above Preparation Example 2 was diluted with water to a concentration of 0.8 ppm as a concentration of active ingredient. The same experiment as in Test Example 2 was carried out, and the prevention/extermination titer was calculated according to the formula 2.

In this test, representative compounds having the acaricidal effect with more than 90 of prevention/extermination titer include compound No. 63, 93, 77, 81, 105, 169, 190, 196 and 208. Further, these compounds did not show any adverse effect on the soybean seedling.

$$\text{prevention/extermination titer}=[1-(\text{number of imago before treatment in the untreated field/number of imago before treatment in the treated field})\times(\text{number of imago at the observation day in the treated field/number of imago at the observation day in the untreated field})]\times 100 \quad (2)$$

Test Example 4

Prevention/Extermination Test Against *Meloidogyne incognita*

Meloidogyne incognita contaminated soil was placed in a small plastic pot, and was treated by mixing with diluted wettable powder prepared according to the above Preparation Example 2, at a dosage of 1,500 g as active ingredient per 10 ares. Seven (7) days later, the soil was mixed and left for additional 24 hrs, then 5 grains of cucumber seed were seeded in the soil. Fourteen (14) days after seeding, levels of nodules generated on the cucumber root were examined according to the judgment criteria 1, and nodule index was calculated according to the formula 3 below.

In this test, representative compounds which had the inhibitory effect on the nodule formation with the nodule index of 10 or less include compound No. 81, 247 and 249.

Criteria 1

Plenty: numerous nodules are detected all over the rhizome.

Medium: medium level of nodule formation is detected.

Minor: a few nodules are detected.

Rare: nodules are undetectable at a glance, but a small number of nodules are detected by careful inspection.

None: undetected $$\text{nodule index}=\{[(1\times A)+(2\times B)+(3\times C)+(4\times D)]/(4\times N)\}\times 100 \quad (3)$$

wherein, A is a number of root judged as rare, B is a number of root judged as minor, C is a number of root judged as medium, D is a number of root judged as plenty, and N is the total number of root inspected.

Test Example 5

Oral Acute Toxicity Test

Oral acute toxicity test was conducted according to the method described in the guideline in "Guideline for the Preparation of Test Report on the Toxicity Studies", published by the Ministry of Agriculture, Forestry and Fisheries of Japan. Experimental animals, 3 each of male and female of 7 weeks aged ddy mouse (Slc:ddy), were obtained from SLC Japan Inc. The compounds of the present invention and the reference substances were suspended in 0.5% sodium carboxymethyl cellulose or corn oil to give a 30 (mg/kg) equivalent amount for a dosage of 10 ml per 1 kg of body weight. The suspensions were inoculated using a sonde directly into the stomach of test animals which were fasted for 3 hours before inoculation. The test animals were fasted for additional 3 hours after inoculation, and the mortality of the inoculated animal was investigated for 7 days. The results are shown in Table 38. In this table, 0/3 means none of 3 recipient animals died, 1/3 means one out of 3 recipient animals died, 2/3 means 2 out of 3 recipient animals died, 3/3 means all 3 recipient animals died.

TABLE 38

| Compound No. of the present invention | Test result | |
|---|---|---|
| | Male | Female |
| 1 | 0/3 | 0/3 |
| 3 | 0/3 | 0/3 |
| 18 | 0/3 | 0/3 |
| 29 | 0/3 | 0/3 |
| 63 | 0/3 | 0/3 |
| 77 | 0/3 | 0/3 |
| 81 | 0/3 | 0/3 |
| 93 | 0/3 | 0/3 |
| 105 | 0/3 | 0/3 |
| 119 | 0/3 | 0/3 |
| Reference compound A | 3/3 | 3/3 |
| Reference compound B | 3/3 | 3/3 |
| Reference compound C | 3/3 | 3/3 |
| Reference compound D | 3/3 | 3/3 |

In the above-table:

Reference compound A: 6,6-difluoro-5-hexenyl 6-chloronicotinate (the compound described in JP-A-2000-038379);

Reference compound B: 4,4-difluoro-3-butenyl 2-butoxy-4-methylpyrimidine-5-carboxylate Reference compound C: 4,4-difluoro-3-butenyl 4-methyl-2-phenylpyrimidine-5-carboxylate Reference compound D: 6,6-difluoro-5-hexenyl benzo[b]thiophen-2-carboxylate

INDUSTRIAL APPLICABILITY

A compounds of the present invention has high safety for crop plants. Also, a compound of the present invention demonstrate an superior prevention/extermination effect against a wide variety of pest insects such as Hemiptera, Lepidoptera, Coleoptera, Diptera, Hymenoptera, Orthoptera, Isoptera, Thysnoptera, *Tetranychus* and plant parasitic Nematodes. Further, a compound of the present invention has not only an ability to control insecticide-resistant noxious organisms, but also high safety for mammals and natural enemies of the pest insects.

What is claimed is:

1. A difluoroalkene derivative having the general formula [1] or a pharmacologically acceptable salt thereof:

[1]

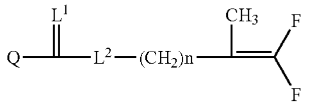

wherein $L^1$ and $L^2$ are the same or different and each represents an oxygen atom or a sulfur atom;

n represents an integer of 2 to 8;

Q may be substituted with same or different 1 to 4 substituents group X;

Q represents a hetero ring shown by:

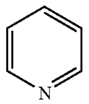

X represents a hydroxyl group, a halogen atom, an alkyl group with 1 to 12 carbon atoms which may be mono-substituted with any group selected from substituents group α, an alkoxy group with 1 to 12 carbon atoms which may be mono-substituted with any group selected from substituents group α, an alkylthio group with 1 to 12 carbon atoms which may be mono-substituted with any group selected from substituents group α, an alkylsulfinyl group with 1 to 12 carbon atoms which may be mono-substituted with any group selected from substituents group α, an alkylsulfonyl group with 1 to 12 carbon atoms which may be mono-substituted with any group selected from substituents group α, an acyl group with 1 to 6 carbon atoms which may be mono-substituted with any group selected from substituents group α, an alkoxycarbonyl group with 2 to 6 carbon atoms which may be mono-substituted with any group selected from substituents group α, an acylamino group with 1 to 6 carbon atoms which may be mono-substituted with any group selected from substituents group α (a nitrogen atom of said group may be substituted with an alkyl group with 1 to 6 carbon atoms), an alkylsulfonylamino group with 1 to 6 carbon atoms which may be mono-substituted with any group selected from substituents group α (a nitrogen atom of said group may be substituted with an alkyl group with 1 to 6 carbon atoms), a haloalkyl group with 1 to 4 carbon atoms, an alkoxyalkyl group with 2 to 6 carbon atoms, an alkenyl group with 2 to 6 carbon atoms, a haloalkenyl group with 2 to 7 carbon atoms, an alkynyl group with 2 to 6 carbon atoms which may be mono-substituted with any group selected from substituents group α, a cycloalkyl group with 3 to 6 carbon atoms, a cycloalkylalkyl group with 4 to 7 carbon atoms (said group may be substituted with a halogen atom or an alkyl group), a haloalkoxy group with 1 to 6 carbon atoms, an alkoxyalkyloxy group with 2 to 6 carbon atoms, an alkenyloxy group with 3 to 8 carbon atoms, a haloalkenyloxy group with 3 to 8 carbon atoms, an alkynyloxy group with 3 to 6 carbon atoms, a cycloalkyloxy group with 3 to 7 carbon atoms, a cycloalkylalkyloxy group with 4 to 7 carbon atoms (said group may be substituted with a halogen atom or an alkyl group), an acyloxy group with 1 to 6 carbon atoms, a haloalkylcarbonyl group with 2 to 5 carbon atoms, a cyano group, a carbamoyl group (a nitrogen atom of said group may be substituted with the same or different alkyl group having 1 to 4 carbon atoms), a phenyl group which may be substituted with any 1 to 4 groups selected from substituents group β, a phenoxy group which may be substituted with any 1 to 4 groups selected from substituents group β, a phenylthio group which may be substituted with any 1 to 4 groups selected from substituents group β, a phenylsulfinyl group which may be substituted with any 1 to 4 groups selected from substituents group β, a phenylsulfonyl group which may be substituted with any 1 to 4 groups selected from substituents group β, a phenylamino group which may be substituted with any 1 to 4 groups selected from substituents group β [a nitrogen atom of said group may be substituted with an alkyl group having 1 to 4 carbon atoms, an alkenyl group having 2 to 4 carbon atoms, an alkynyl group having 3 to 4 carbon atoms, an acyl group having 1 to 4 carbon atoms, an alkoxycarbonyl group having 2 to 4 carbon atoms, a carbamoyl group (a nitrogen atom of said group may be substituted with the same or different alkyl group having 1 to 4 carbon atoms), or an alkylsulfonyl group having 1 to 4 carbon atoms], a pyridyl group which may be substituted with any 1 to 4 groups selected from substituents group β, a thienyl group which may be substituted with any 1 to 3 groups selected from substituents group β, a pyrazolyl group which may be substituted with any 1 to 3 groups selected from substituents group β, a pyridyloxy group which may be substituted with any 1 to 4 groups selected from substituents group β, a phenylcarbamoyl group which may be substituted with any 1 to 4 groups selected from substituents group β (a nitrogen atom of said group may be substituted with an alkyl group having 1 to 4 carbon atoms), a benzoyl group which may be substituted with any 1 to 4 groups selected from substituents group β, a benzoylamino group which may be substituted with any 1 to 4 groups selected from substituents group β (a nitrogen atom of said group may be substituted with an alkyl group having 1 to 4 carbon atoms), a phenylsulfonylamino group which may be substituted with any 1 to 4 groups selected from substituents group β (a nitrogen atom of said group may be substituted with an alkyl group having 1 to 4 carbon atoms), a phthalimide group which may be substituted with any 1 to 4 groups selected from substituents group β, a nitro group, an amino group, an alkylamino group with 1 to 12 carbon atoms which may be mono-substituted with any group selected from substituents group α (a nitrogen atom of said group may be substituted with alkyl group having 1 to 6 carbon atoms which may be mono-substituted with any group selected from substituents group β, an alkenyl group having 2 to 4 carbon atoms, an alkynyl group having 3 to 4 carbon atoms or a hydroxyl group), an cycloalkylamino group with 3 to 6 carbon atoms (a nitrogen atom of said group may be substituted with an alkyl group having 1 to 6 carbon atoms, an alkenyl group having 2 to 4 carbon atoms, an alkynyl group having 3 to 4 carbon atoms, an acyl group having 1 to 4 carbon atoms, an alkoxycarbonyl group having 2 to 4 carbon atoms or an alkylsulfonyl group having 1 to 4 carbon atoms), an alkoxyamino group with 1 to 12 carbon atoms which may be mono-substituted with any group selected from substituents group α (a nitrogen atom of said group may be substituted with an alkyl group having 1 to 10 carbon atoms which may be mono-substituted with any group selected from substituents group α, an alkenyl group having 2 to 4 carbon atoms, an alkynyl group having 3 to 4 carbon atoms, an acyl group having 1 to 4 carbon atoms, an alkoxycarbonyl group having 2 to 4 carbon atoms or an alkylsulfonyl group having 1 to 4 carbon atoms), a pyrrolidinyl group, a piperidinyl group, a haloalkylcarbonylamino group having 2 to 5 carbon atoms (a nitrogen atom of said group may be substituted with an alkyl group having 1 to 6 carbon atoms) or a haloalkylsulfonylamino group having 1 to 4 carbon atoms (a nitrogen atom of said group may be substituted with an alkyl group having 1 to 6 carbon atoms);

a substituents group X may form a 5- to 8-membered ring which may be substituted with 1 to 4 halogen atoms, by bonding two adjacent alkyl groups, alkoxy groups, an alkyl group and an alkoxy group, an alkyl group and an alkylthio group, an alkyl group and an alkylsulfonyl group, an alkyl group and a monoalkylamino group or an alkyl group and a dialkylamino group;

[Substituents Group α]

Substituents group α include a phenyl group which may be substituted with any 1 to 4 groups selected from substituents group β, a phenoxy group which may be substituted with any 1 to 4 groups selected from substituents group β, a benzyloxy group which may be substituted with any 1 to 4 groups selected from substituents group β, a pyridyl group which may be substituted with any 1 to 4 groups selected from substituents group β, a pyridyloxy group which may be substituted with any 1 to 4 groups selected from substituents group β, a benzoyloxy group which may be substituted with any 1 to 4 groups selected from substituents group β, a benzoylamino group which may be substituted with any 1 to 4 groups selected from substituents group β (a nitrogen atom of said group may be substituted with an alkyl group having 1 to 4 carbon atoms), a phenylsulfonylamino group which may be substituted with any 1 to 4 groups selected from substituents group β (a nitrogen atom of said group may be substituted with an alkyl group having 1 to 4 carbon atoms), a phenylcarbamoyl group which may be substituted with any 1 to 4 groups selected from substituents group β (a nitrogen atom of said group may be substituted with an alkyl group having 1 to 4 carbon atoms) and a benzyloxycarbonyl group which may be substituted with any 1 to 4 groups selected from substituents group β or a cyano group;

[Substituents Group β]

Substituents group β include a hydroxyl group, a halogen atom, an alkyl group with 1 to 6 carbon atoms, a haloalkyl group with 1 to 4 carbon atoms, an alkoxy group with 1 to 6 carbon atoms, a haloalkoxy group with 1 to 4 carbon atoms, a methylenedioxy group, an alkylthio group with 1 to 6 carbon atoms, an alkylsulfinyl group with 1 to 6 carbon atoms, an alkylsulfonyl group with 1 to 6 carbon atoms, a cyano group, a carbamoyl group (a nitrogen atom of said group may be substituted with an alkyl group having 1 to 4 carbon atoms), a nitro group, an amino group, a phenyl group which may be substituted with any 1 to 4 groups selected from substituents group γ, a phenoxy group which may be substituted with any 1 to 4 groups selected from substituents group γ, a benzyloxy group which may be substituted with any 1 to 4 groups selected from substituents group γ, a pyridyl group which may be substituted with any 1 to 4 groups selected from substituents group γ, a pyridyloxy group which may be substituted with any 1 to 4 groups selected from substituents group γ, a benzoylamino group which may be substituted with any 1 to 4 groups selected from substituents group γ (a nitrogen atom of said group may be substituted with an alkyl group having 1 to 4 carbon atoms), a phenylsulfonylamino group which may be substituted with any 1 to 4 groups selected from substituents group γ (a nitrogen atom of said group may be substituted with an alkyl group having 1 to 4 carbon atoms), a phenylcarbamoyl group which may be substituted with any 1 to 4 groups selected from substituents group γ (a nitrogen atom of said group may be substituted with an alkyl group having 1 to 4 carbon atoms), an alkylamino group with 1 to 4 carbon atoms, a dialkylamino group with 1 to 4 carbon atoms (a dialkyl group of said group may be the same or different), an acylamino group with 1 to 6 carbon atoms (a nitrogen atom of said group may be substituted with an alkyl group having 1 to 4 carbon atoms or an acyl group having 1 to 4 carbon atoms), a haloalkylcarbonylamino group with 1 to 5 carbon atoms (a nitrogen atom of said group may be substituted with an alkyl group having 1 to 4 carbon atoms), an alkylsulfonylamino group with 1 to 6 carbon atoms (a nitrogen atom of said group may be substituted with an alkyl group having 1 to 4 carbon atoms) or a haloalkylsulfonylamino group with 1 to 4 carbon atoms (a nitrogen atom of said group may be substituted with an alkyl group having 1 to 4 carbon atoms);

[Substituents Group γ]

Substituents group γ include a hydroxyl group, a halogen atom, an alkyl group with 1 to 6 carbon atoms, an haloalkyl group with 1 to 4 carbon atoms, an alkoxy group with 1 to 6 carbon atoms, a haloalkoxy group with 1 to 4 carbon atoms, a methylenedioxy group, a cyano group, a nitro group, an amino group, an acylamino group with 1 to 6 carbon atoms (a nitrogen atom of said group may be substituted with an alkyl group having 1 to 4 carbon atoms), a haloalkylcarbonylamino group with 1 to 5 carbon atoms (a nitrogen atom of said group may be substituted with an alkyl group having 1 to 4 carbon atoms), an alkylsulfonylamino group with 1 to 6 carbon atoms (a nitrogen atom of said group may be substituted with an alkyl group having 1 to 4 carbon atoms) or a haloalkylsulfonylamino group with 1 to 4 carbon atoms (a nitrogen atom of said group may be substituted with an alkyl group having 1 to 4 carbon atoms).

2. The difluoroalkene derivative or the pharmacologically acceptable salt thereof according to claim 1, wherein $L^1$ and $L^2$ each is an oxygen atom and n is an integer of 2 to 4.

3. The difluoroalkene derivative or the pharmacologically acceptable salt thereof according to claim 1, wherein $L^1$ and $L^2$ each is an oxygen atom and n is an integer of 2 to 4;

wherein Q may be substituted with 1 to 3 the same or different substituents group X;

X is a halogen atom, an alkyl group having 1 to 6 carbon atoms, an alkoxy group having 1 to 6 carbon atoms, an alkylthio group having 1 to 6 carbon atoms, a haloalkoxy group having 1 to 6 carbon atoms, an alkenyloxy group having 3 to 6 carbon atoms, a haloalkenyloxy group having 3 to 6 carbon atoms, an alkynyloxy group having 3 to 6 carbon atoms, a cycloalkyl group having 3 to 6 carbon atoms, a cycloalkyloxy group having 3 to 7 carbon atoms, a phenyl group (said group may be substituted with a haloalkyl group having 1 to 4 carbon atoms), a benzyl group, a phenoxy group, a phenylthio group, a phenylamino group (a nitrogen atom of said group may be substituted with an alkyl group having 1 to 4 carbon atoms or an alkynyl group having 3 to 4 carbon atoms), an alkylamino group having 1 to 6 carbon atoms (a nitrogen atom of said group may be substituted with an alkyl group having 1 to 6 carbon atoms or an alkynyl group having 3 to 4 carbon atoms, an acyl group having 1 to 5 carbon atoms or a haloalkylcarbonyl group having 2 to 5 carbon atoms), a cycloalkylamino group having 3 to 6 carbon atoms (a nitrogen atom of said group may be substituted with an alkyl group having 1 to 6 carbon atoms), an alkoxyamino group having 1 to 6 carbon atoms (a nitrogen atom of said group may be substituted with an alkyl group having 1 to 6 carbon atoms), a benzylamino group (a nitrogen atom of said group may be substituted with an alkyl group having 1 to 6 carbon atoms), a pyrrolidinyl group and a piperidinyl group.

4. The difluoroalkene derivative or the pharmacologically acceptable salt thereof according to claim 1, wherein $L^1$ and $L^2$ each is an oxygen atom and n is an integer of 2 to 4;

wherein Q may be substituted with 1 to 3 the same or different substituents group X;

X is an alkyl group having 1 to 6 carbon atoms, an alkoxy group having 1 to 6 carbon atoms, an alkylthio group having 1 to 6 carbon atoms, an alkenyloxy group having 3 to 6 carbon atoms, a haloalkenyloxy group having 3 to 6 carbon atoms, an alkynyloxy group having 3 to 6 carbon atoms, a cycloalkyloxy group having 3 to 7 carbon atoms, a phenyl group, a phenoxy group, a phenylthio group and a phenylamino group (a nitrogen atom of said group may be substituted with an alkyl group having 1 to 4 carbon atoms).

5. A pest control agent containing, as an effective ingredient, the difluoroalkene derivative having the general formula [1] or the pharmacologically acceptable salt thereof according to claim 1.

* * * * *